(12) United States Patent
Singh et al.

(10) Patent No.: US 7,566,732 B2
(45) Date of Patent: Jul. 28, 2009

(54) RHODANINE COMPOSITIONS FOR USE AS ANTIVIRAL AGENTS

(75) Inventors: Rajinder Singh, Belmont, CA (US); Usha Ramesh, Cupertino, CA (US); Sarkiz D. Issakani, Redwood City, CA (US); Gary Charles Look, Santa Clara, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 766 days.

(21) Appl. No.: 10/975,761

(22) Filed: Oct. 28, 2004

(65) Prior Publication Data

US 2009/0137644 A1    May 28, 2009

Related U.S. Application Data

(60) Provisional application No. 60/526,726, filed on Dec. 3, 2003, provisional application No. 60/514,951, filed on Oct. 28, 2003.

(51) Int. Cl.
*A61K 31/425* (2006.01)
*C07D 413/00* (2006.01)
*C07D 401/00* (2006.01)
*C07D 403/00* (2006.01)
*C07D 417/00* (2006.01)
*C07D 419/00* (2006.01)
*C07D 235/04* (2006.01)

(52) U.S. Cl. .................. 514/369; 544/82; 544/284; 548/305.1

(58) Field of Classification Search .................. None
See application file for complete search history.

(56) References Cited

U.S. PATENT DOCUMENTS

| 4,376,777 | A | 3/1983 | Kawamatsu et al. |
| 2003/0027798 | A1 | 2/2003 | Druzgala et al. |
| 2004/0214872 | A1* | 10/2004 | Suto et al. .................. 514/369 |

FOREIGN PATENT DOCUMENTS

| FR | 2858324 A | 2/2005 |
| GB | 2386892 A | 10/2003 |
| GB | 2387172 A | 10/2003 |
| WO | WO 00/10573 A | 3/2000 |
| WO | WO 01/77091 A | 10/2001 |
| WO | WO 01/81328 A | 11/2001 |
| WO | WO 2004/024061 A | 3/2004 |

OTHER PUBLICATIONS

Chizhevskaya et al. Abstract of Chizhevskaya et al., Vesti Akademii Navuk BSSR, 1970, vol. 6, pp. 78-81.*
Sohda, T. et al., "Antiulcer activity of 5-benzyhlthiazolidine-2,4-dione derivatives", Chemical and Pharmaceutical Bulletin, Pharmaceutical Society of Japan, Tokyo, JP, vol. 31, No. 2, Feb. 1983, pp. 560-569, XP002193484, ISSN: 0009-2363; examples 19, 35; table II example 40; tabel III.
Giles, R.G. et al., "Regiospecific Reduction of 5-Benzylidene-2, 4-thiazolidinediones and 4-Oxo-2-thiazolidinethiones using Lithium Borohydride in Pyridine and Tetrahydrofuran" Tetrahedron, Elsevier Science Publishers, Amsterdam, NL, vol. 56, No. 26, Jun. 2000, pp. 4531-4537, XP004202146, ISSN: 0040-4020, examples a,b,c,f,1; table 1.
Sutihnen, Jussi et al., "Effects of rosiglitazone on gene expression in subcutaneous adipose tissue in highly active antiretroviral therapy-associated lipodystrophy", American Journal of Physiology, 286(6, PT. 1), E941-E949 CODEN: AJPHAP; ISSN: p. E941, col. 1, Jan. 2004.
Obushak, N.D. et al., "Synthesis of heterocycles based on products of aniohnarylation of unstuarted compounds. II. Method of prepration of 2,5-disubstituted 4-thiazolidinones", Russian Journal of Organic Chemistry (Translation of Zhurnal Organicheskoi Khimii), 34(2), 239-244 Coden: RJOCEQ; ISSN: 1070-4280, 1998, XP008047401, examples XIa, b, c, d, f, g; table 2.
Kassab, Nazmi A. E. L., et al., "Reactions with 5-Substituted 2-thiazolidine-4-thiones. IV" Journal Fuer Praktische Chemie (Leipzig), 316(2), 209-14 Coden: JPCEAP; ISSN: 0021-8383, 1974, XP008047365 p. 14; examples 6a, 6d.
Sing W. T. et al., "Arylalkylidene Rhodanine with Bulky and Hydrophobic Functional Gorup as Selective HCV NS3 Protease Inhibitor", Bioorganic & Medicinal Chemistry Letters, Oxford, GB, vol. 11, No. 2, Jan. 2001, pp. 91-94, XP004314823, ISSN: 0960-894X, examples 2a, 2b, 2f-2h; table 1.
Awasthi, L.P. et al., "Antimicrobial activity of 3-methyl-5-furfurylidene-2-thioxo-4-thiazolidones" Folia Microbiologica (Prague, Czech Republic), 28(1), 41-5 CODEN; Fomiaz; ISSN: 0015-5632, 1983, XP008046916, p. 41, p. 42, paragraph 4, table 1.
Krutosikova, A. et al., "Furan derivatives XXIV. Synthesis of substituted 5-(5-phenjyl-2-furfurylidene)rhodanines" Sbornik Prac Chemickej Fakulty Svst, Volume Date 1969-1970 55-8 CODEN: SCFSAL: ISSN: 0520-7339, 1971, XP008046923, p. 56; table 1.
Hardy, R.W. et al., "Hepatitis C virus RNA Synthesis in a cell-free system isolated from replicon-containing hepatoma cells", Journal of Virology, The American Society for Microbiology, US, vol. 77, No. 3, Feb. 2003, pp. 2029;2037, XP008046926, ISSN: 0022-538X, figure 7, p. 2029, col. 1-col. 2.
Chapman R. L. et al., "Small molecule modulators of HIV ref/rev response element interaction identified by random screening", Antiviral Research, Elsevier Science BV., Amstgerdam, NL, vol. 54, No. 3, 2002, pp. 149-162, XP008046900, ISSN: 0166-3542, figure 2; example 2, table 2, table 1.
Spiegel P C, et al., "Disruption of Protein-Memrain Binding and Identification of Small-Molecule Inhibitors of Coagulation Factor VIII", Chemistry and Biology, Current Biology, London GB, vol. 11, No. 10, Oct. 2004, pp. 1413-1422, XP004601875, ISSN: 1074-5521; figure 3; examples 3,4.

* cited by examiner

*Primary Examiner*—Sreeni Padmanabhan
*Assistant Examiner*—Samira Jean-Louis
(74) *Attorney, Agent, or Firm*—McDonnell Boehnen Hulbert & Berghoff LLP

(57) ABSTRACT

This invention describes compounds and pharmaceutical compositions useful as inhibitors of ubiquitination. The compounds and compositions of the invention are useful as inhibitors of the biochemical pathways of organisms in which ubiquitination is involved. In particular, the compounds and compositions are useful for treating diseases caused by viruses such as poxviruses and retroviruses. The invention further provides for methods of treating smallpox, Herpes virus and HIV infection in patients using the compounds and compositions of the invention.

3 Claims, No Drawings

RHODANINE COMPOSITIONS FOR USE AS ANTIVIRAL AGENTS

CROSS REFERENCE TO RELATED APPLICATIONS

This application claims priority from U.S. Provisional Application Ser. No. 60/514,951, filed Oct. 28, 2003, and U.S. Provisional Application Ser. No. 60/526,726, filed Dec. 3, 2003, both of which are incorporated herein by reference in their entirety.

BACKGROUND OF THE INVENTION

1. Field of the Invention

The present invention relates generally to the field of antiviral compounds, particularly compounds that act by inhibiting the ubiquitin ligase activity of a poxvirus p28 protein.

2. Summary of the Related Art

Smallpox is a serious, highly contagious, and frequently a fatal infectious disease for which there is no specific and effective treatment. The primary method of prevention is by vaccination. Two clinical forms of smallpox have been described: variola minor and variola major. The variola major form of smallpox is the most common and severe form. There are four types of variola major smallpox, namely, ordinary (the most frequent); modified (mild and occurring in previously vaccinated persons); flat; and hemorrhagic. Overall, variola major has a case-fatality rate of about 30%.

The most virulent form of smallpox, hemorrhagic smallpox, destroys the linings of the throat, stomach, intestines, rectum, and vagina. It causes black, unclofted blood to ooze from the mouth and other body orifices. Because hemorrhagic smallpox has a much shorter incubation period than other forms of smallpox, it is likely not to be initially recognized as smallpox when first presented to medical care. As such, most victims die prior to a correct diagnosis, often before they are quarantined. Smallpox vaccination provides little protection against hemorrhagic smallpox as hemorrhagic smallpox causes the death of 94% of vaccinated patients and 99% of unvaccinated patients.

Because variola viruses, particularly smallpox, are so fatal, their inclusions in biological weapons or so called "weapons of mass destruction" are currently thought to be a great public threat. Accordingly, there is an urgent need for methods and compositions for treating and preventing infection with variola viruses, especially smallpox.

Despite intense research, the primary treatments and preventions methods for smallpox are either ineffective or impractical in the event of an outbreak from a virulent strain of smallpox. The primary therapeutic tools for the control and eradication of smallpox include a live virus vaccine to prevent disease, and a vaccinia immune globulin (VIG) to treat dissiminated infections. The smallpox vaccine (live vaccinia virus) has many side-effects including adverse reactions, scarring, ocular autoinoculation, increased incidence of myocardial infarction, and dissemination in immunocompromised persons. Cell culture derived vaccines are being developed; however, these vaccines are also live viruses and pose many of the same drawbacks that plague the current vaccine. Accordingly, the public at large, the healthcare community, and the military have been resistant to smallpox vaccinations because the risks of side-effects appear to outweigh the advantages. Further, as discussed above, current vaccination methods are practically ineffective against hemorrhagic smallpox or its derivatives which are forms that would most likely be used in biological weapons.

The existing vaccinia immune globulin products are derived from human donors who have been vaccinated with vaccinia virus (the vaccine for smallpox). As with all human products, VIG must be tested exhaustively for blood borne human pathogens such as human immunodeficiency virus and hepatitis B. Therefore, VIG suffers from several drawbacks including the necessity for using human volunteers, i.e. the use of a live virus as an immunogen which could cause infectious lesions that scar healthy individuals and severe disseminated life-threatening infection in immunocompromised individuals. Despite continuous screening of the donor population to assure consistency which is very expensive, product lots can vary significantly between batches and geographic regions.

Accordingly, the primary treatment for smallpox infection is impractical in most situations. In addition, since vaccinia virus is an ineffective vaccine for hemorrhagic smallpox, it is unlikely vaccinia immune globulin products will be effective against hemorrhagic smallpox.

Research into the biology of smallpox is intensive. For example, the genome of variola virus has been sequenced, and it is about 185 kbp in length and is predicted to contain over 200 proteins. Many of the proteins involved in transcription and DNA replication as well as about 30 proteins that form the core and membrane components of the virus particles have been identified. Other viral proteins have been identified that are thought to interact with host components to facilitate virus dissemination, prevent apoptosis, and attenuate immune responses. However, although well over 10 years have passed since the genome of vaccinia virus was sequenced, the biochemical functions of most viral proteins, in particular, p28, which has been shown to be required for viral pathogenesis, remain elusive. As such, despite great effort, the development of anti-viral assays and the discovery of effective drugs to combat smallpox infection have been letargic.

Accordingly, despite great effort and the continuous threat of a serious hemorrhagic smallpox outbreak, an effective, practical therapy (including prevention and treatment) for smallpox, is currently unavailable. Accordingly, there is a great need for new assays to discover drugs for the treatment of smallpox as well as a great need for new smallpox therapies, particularly those that may be deployed rapidly, safely and in great number. This invention describes compounds, compositions and methods that satisfy these needs and others.

Literature of Interest

Literature of interest includes Afonso et al, J. Virology 74: 3815-3831, 2000; Brick et al, J. General Virology 81: 1087-1097, 2000; Senkevich et al, Virology 198: 118-128, 1994; Senkevich et al, J. Virology 69: 4103-4111 1995; Antoine et al, Virology 244:365-96, 1998; Upton et al, Virus Genes 20:159-64, 2000; Perkus et al, Virology 180:406-10, 1991; McCraith et al, Proc Natl Acad Sci 97:4879-84, 2000; Goebel, et al, 1990 Virology 179, 247-266, 517-563; Jensen et al. 1996 J. Virol. 70, 7485-7497; Takahashi et al 1994 Virology 202, 844-852; Alcami, et al, 1998 Semin. Virol. 8, 419-427; McFadden, et al, 1998 Semin. Virol. 8, 429-442 and GenBank Accession number X69198.s.

BRIEF DESCRIPTION OF THE INVENTION

The invention comprises compounds and pharmaceutical compositions of the compounds for inhibiting ubiquitination. The pharmaceutical compositions can be used in treating various conditions where ubiquitination is involved. They can also be used as research tools to study the role of ubiquitin in various natural and pathological processes.

In a first aspect, the invention provides for compounds that inhibit ubiquitination of target proteins.

In a second aspect, the invention provides for pharmaceutical compositions comprising an inhibitor of ubiquitination of the invention and a pharmaceutically acceptable carrier, excipient or diluent.

In a third aspect, the invention provides for a method for treating diseases or conditions caused by viruses comprising administering to a patient a compound or pharmaceutical composition of the invention. The invention also provides for the use of a compound or composition of the invention for the manufacture of a medicament for use in treating diseases or conditions caused by viruses.

In a fourth aspect, the invention provides for a method for treating HIV infection and related conditions. The invention also provides for the use of a compound or composition of the invention for the manufacture of a medicament for use in treating HIV infection and related conditions.

In a fifth aspect, the invention provides for a method for treating Herpes virus infection and related conditions. The invention also provides for the use of a compound or composition of the invention for the manufacture of a medicament for use in treating Herpes virus infection and related conditions.

In a sixth aspect, the invention provides for a method of using the compounds of the invention for inhibiting the side effects of vaccination. The invention also provides for the use of a compound or composition of the invention for the manufacture of a medicament for use in inhibiting the side effects of vaccination.

In a seventh aspect, the invention provides for a method of using the compounds of the invention for inhibiting smallpox infection. The invention also provides for the use of a compound or composition of the invention for the manufacture of a medicament for use in inhibiting smallpox infection.

In an eight aspect, the invention provides for a method of inhibiting poxvirus pathogenicity in infected individuals. The invention also provides for the use of a compound or composition of the invention for the manufacture of a medicament for use in inhibiting poxvirus pathogenicity in infected individuals.

The foregoing only summarizes certain aspects of the invention and is not intended to be limiting in nature. These aspects and other aspects and embodiments are described more fully below. All patent applications and publications of any sort referred to in this specification are hereby incorporated by reference in their entirety. In the event of a discrepancy between the express disclosure of this specification and a patent application or publication incorporated by reference, the express disclosure of this specification shall control.

DETAILED DESCRIPTION OF THE INVENTION

First Aspect. The first aspect of the invention comprises compounds having the formula

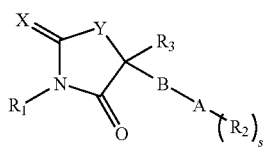

I or pharmaceutically acceptable salts thereof, wherein
A is aryl or heteroaryl;
B is $C_1$-$C_6$ alkyl or $C_2$-$C_6$ alkenyl;
X is sulfur, oxygen, $CR_4R_5$, $NR_4$, $NC(O)R_4$ or $NSO_2R_4$;
Y is sulfur, oxygen, —C($R_4$)($R_5$)—, —N($R_4$)—, —N(C(O)$R_4$)—, —N($SO_2R_4$)—, —$SO_2$—, or —SO—;
$R_1$ is —H, —$NH_2$, $C_1$-$C_6$ alkyl, $C_1$-$C_2$ alkenyl, $C_1$-$C_6$ alkyl-S—$C_1$-$C_6$ alkyl, $C_0$-$C_6$ alky-aryl, $C_0$-$C_6$ alkyl-C(O)O$R_6$, $C_0$-$C_6$ alkyl-heteroaryl, $C_0$-$C_6$ alkyl-heterocyclyl, $C_0$-$C_6$ alkyl-carbocyclyl, —NH—$SO_2$-aryl, —$C_0$-$C_6$ alkyl-C(O)N$R_6R_7$, —$C_0$-$C_6$ alkyl-C(S)N$R_6R_7$, $C_0$-$C_6$ alky-heteroaryl-aryl, —NHC(O)-aryl, $C_0$-$C_6$ alkyl-C(O)NH—$C_0$-$C_6$ alkyl-C(O)—O—$R_6$, $C_0$-$C_6$ alkyl-C(O)—NH—$C_0$-$C_6$ alkyl-aryl, $C_0$-$C_6$ alkyl-C(O)—NH—$C_0$-$C_6$ alkyl-heteroaryl, $C_0$-$C_6$ alkyl-C(O)—NH—$C_0$-$C_6$ alkyl-heterocyclyl, $C_0$-$C_6$ alkyl-C(O)—NH—$C_0$-$C_6$ alkyl-carbocyclyl, —$SO_2$—$R_6$, C(O)—$R_6$, or —C(O)—O$R_6$, wherein each one of the alkyl, aryl, heteroaryl, heterocyclic and carbocyclyl are optionally substituted with one or more $R_5$;
s is 1, 2, or 3 (when s is 2 or 3, A is substituted with 2 or 3 $R_2$ groups);
each $R_2$ is independently —H, halogen, $C_1$-$C_6$ alkyl, $C_0$-$C_6$ alky-aryl, —$NO_2$, $C_0$-$C_6$ alkyl-C(O)—O$R_6$, $C_0$-$C_6$ alkyl-heteroaryl, $C_0$-$C_6$ alkyl-heterocyclyl, $C_0$-$C_6$ alkyl-carbocyclyl, —N($R_6$)—C(O)N$R_6R_7$, —NH$SO_2$-aryl, $C_0$-$C_6$ alky-heteroaryl-aryl, or —C(O)—$R_6$, wherein each one of the aryl, heteroaryl, heterocyclic and carbocyclyl are optionally substituted with one or more $R_4$;
$R_3$ is —H, $C_1$-$C_6$ alkyl or $C_2$-$C_6$ alkenyl; or
$R_3$ and B together with the carbon atom to which they are attached form an alkenyl or a spirocyclic ring;
$R_4$ is halogen, oxo, —C(O)O$R_6$, —$NO_2$, $C_1$-$C_6$ alkyl optionally substituted with halo, —$C_1$-$C_6$ alkoxy optionally substituted with halo, —$CF_3$, —$SO_2NH_2$, or —C(O)—O$R_6$;
$R_5$ is halogen, oxo, $C_1$-$C_6$ alkoxy, $C_1$-$C_6$ alkyl, $C_0$-$C_6$ alkyl-aryl, —$NO_2$, di($C_1$-$C_6$ alkyl)amino, —$CF_3$, —OH, —$SO_2NH_2$, or —C(O)—O$R_6$; and
$R_6$ and $R_7$ are independently —H, halogen, $C_1$-$C_6$ alkoxy, $C_1$-$C_6$ alkyl, $C_2$-$C_6$ alkenyl, aryl, di($C_1$-$C_6$ alkyl)amino, —$CF_3$, —OH, or —C(O)—O$R_6$.

Certain preferred compounds of formula I are those in which s is 2 or 3.

EMBODIMENT 1

The invention also comprises compounds of formula I having the formula

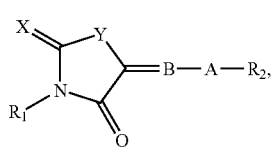

II or pharmaceutically acceptable salts thereof.

EMBODIMENT 2a

The invention further comprises compounds of formula I of the formula

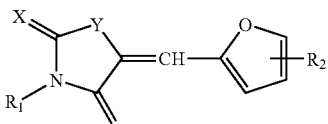

IIIa or pharmaceutically acceptable salts thereof.

EMBODIMENT 2b

The invention further comprises compounds of formula I of the formula

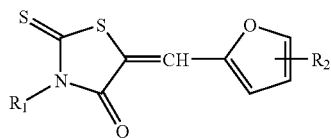

IIIb or pharmaceutically acceptable salts thereof.

EMBODIMENT 3

In a preferred embodiment of the invention the compounds of formula IIIa or IIIb are compounds wherein $R_1$ is —H, $C_1$-$C_6$ alkyl, $C_1$-$C_2$ alkenyl, $C_0$-$C_6$ alky-aryl, $C_0$-$C_6$ alkyl-C(O)O$R_6$, $C_0$-$C_6$ alkyl-heteroaryl, $C_0$-$C_6$ alkyl-heterocyclyl, $C_0$-$C_6$ alkyl-carbocyclyl or $C_0$-$C_6$ alky-heteroaryl-aryl, and $R_2$ is —H, halogen, $C_1$-$C_6$ alkyl or $C_0$-$C_6$ alky-aryl. More preferably, $R_1$ is —H, $C_1$-$C_6$ alkyl, $C_1$-$C_2$ alkenyl, $C_0$-$C_6$ alky-aryl, or $C_0$-$C_6$ alkyl-C(O)O$R_6$ and $R_2$ is $C_0$-$C_6$ alky-aryl. Even more preferably, $R_1$ is —H, allyl, phenyl or benzyl, and $R_2$ is phenyl.

EMBODIMENT 4a

The invention also provides for compounds according to formula I, of the formula

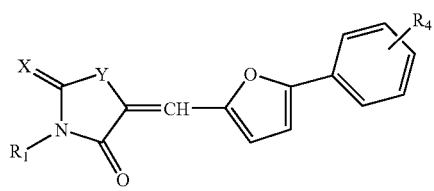

IVa or pharmaceutically acceptable salts thereof.

In a preferred embodiment of Embodiment 4a, X and Y are not both S.

EMBODIMENT 4b

The invention also provides for compounds according to formula I, of the formula

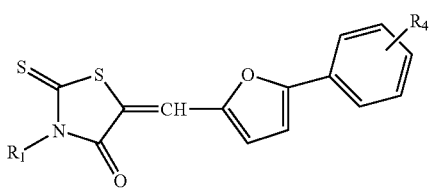

IVb, or pharmaceutically acceptable salts thereof.

EMBODIMENT 5

Preferably, the compounds of formula IVa or IVb are compounds wherein $R_1$ is —H, $C_1$-$C_6$ alkyl, $C_1$-$C_2$ alkenyl, $C_0$-$C_6$ alky-aryl, $C_0$-$C_6$ alkyl-C(O)O$R_6$, $C_0$-$C_6$ alkyl-heteroaryl, $C_0$-$C_6$ alkyl-heterocyclyl, $C_0$-$C_6$ alkyl-carbocyclyl or $C_0$-$C_6$ alky-heteroaryl-aryl, and $R_4$ is halogen, oxo, —NO$_2$, $C_1$-$C_6$ alkyl, —$C_1$-$C_6$ alkoxy, —CF$_3$, —SO$_2$NH$_2$ or —C(O)—O$R_6$. More Preferably, $R_1$ is —H, $C_1$-$C_6$ alkyl, $C_1$-$C_2$ alkenyl, $C_0$-$C_6$ alky-aryl or $C_0$-$C_6$ alkyl-C(O)O$R_6$, and $R_4$ is halogen, —NO$_2$, $C_1$-$C_6$ alkyl, —$C_1$-$C_6$ alkoxy, —CF$_3$, —SO$_2$NH$_2$ or —C(O)—O$R_6$. Even more Preferably, $R_1$ is —H, allyl, phenyl or benzyl, and $R_4$ is chloro, bromo, fluoro, —NO$_2$, —OCH$_3$, —CF$_3$ or —C(O)—OH.

EMBODIMENT 6

The invention also comprises a compound according to embodiment 1, of formula:

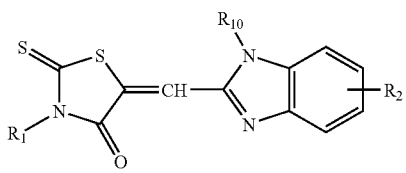

V or pharmaceutically acceptable salts thereof, wherein $R_{10}$ is —H, halogen, $C_1$-$C_6$ alkyl, $C_0$-$C_6$ alky-aryl, —NO$_2$, $C_0$-$C_6$ alkyl-C(O)—O$R_6$, $C_0$-$C_6$ alkyl-heteroaryl, $C_0$-$C_6$ alkyl-heterocyclyl, $C_0$-$C_6$ alkyl-carbocyclyl, —N($R_6$)—C(O)N$R_6R_7$, —NHSO$_2$-aryl, $C_0$-$C_6$ alky-heteroaryl-aryl, or —C(O)—$R_6$, wherein each one of the aryl, heteroaryl, heterocyclic and carbocyclyl are optionally substituted with one or more $R_4$.

EMBODIMENT 7

In certain embodiments according to embodiment 6:
a) $R_{10}$ is selected from —H and $C_1$-$C_6$-alkyl;
b) $R_1$ is (i) aryl optionally substituted with one or more $R_4$ wherein in preferred embodiments $R_1$ is substituted with a single $R_4$ selected from halo and ($C_0$-$C_6$-alkyl)($C_0$-$C_6$-alkyl)N—, more preferably fluoro, chloro, bromo, or di-ethylamino; or (ii) $C_2$-$C_6$ alkenyl, preferably CH$_2$=CH—; and/or
c) $R_2$ is —H or $C_1$-$C_6$ alkyl (preferably —CH$_3$).

EMBODIMENT 8

In certain embodiments according to embodiment 6, the compound is one of the following, or a pharmaceutically acceptable salt thereof:

306

N-[(5E)-5-(1H-benzimidazol-2-ylmethylene)-4-oxo-2-thioxo-1,3-thiazolidin-3-yl]-4-bromobenzamide

307

(5E)-5-(1H-benzimidazol-2-ylmethylene)-3-(4-fluorophenyl)-2-thioxo-1,3-thiazolidin-4-one

308

(5E)-5-(1H-benzimidazol-2-ylmethylene)-3-[4-(diethylamino)phenyl]-2-thioxo-1,3-thiazolidin-4-one

309

(5E)-3-allyl-5-[(1-methyl-1H-benzimidazol-2-yl)methylene]-2-thioxo-1,3-thiazolidin-4-one

EMBODIMENT 9

In another embodiment, the invention comprises compounds of formula I or embodiment 1 that are not also compounds of any of embodiments 2 to 8. For example, the invention comprises compounds wherein X and Y are independently sulfur, oxygen, —$CR_4R_5$, —$NR_4$, —$NC(O)R_4$, —$NSO_2R_4$, —$SO_2$, or —SO, provided that when X or Y is sulfur, the other is not sulfur.

Second Aspect. The second aspect of the invention provides for pharmaceutical compositions comprising a pharmaceutically acceptable carrier, diluent or excipient, and a compound of formula I as described in any of embodiments 7 to 9.

Third Aspect. The third aspect of the invention provides for a method of treating a patient suffering from a disease or condition caused by a virus comprising administering to the patient a compound or composition as described above, including a compound of formula I or a compound according to embodiments 1 to 9, or a composition as described in the Second Aspect of the invention. Accordingly, the compounds of the invention can be used to treat patients suffering from diseases caused by a variety of viruses that use or depend on ubiquitination. Such viruses include, but not limited to, enveloped and non-enveloped viruses such as retroviruses, poxviruses, and herpes viruses. More specifically, the viruses include, but not limited to, smallpox virus and HIV, human papillomavirus, HSV, adenovirus, Coxsackie, HCMV, KSHV, EBV, Paramyxovirus, Myxomavirus, Ebola, Retrovirus, and Rhabdovirus.

The fourth aspect of the invention provides for a method of treating HIV infection or related conditions in a cell, comprising contacting the cell with a compound or composition as described above, including a compound of formula I or a compound according to embodiments 1 to 9, or a composition as described in the Second Aspect of the invention. The compounds and compositions are also useful for inhibiting the spread of HIV. The method comprises contacting an HIV-infected cell of a cell population that also comprises uninfected cells thereby preventing the spread of HIV from the infected cell to the uninfected cell. Thus, the compounds and compositions of the invention can be used to treat patients infected with HIV and suffering from AIDS.

The fifth aspect of the invention provides for a method of treating Herpes virus infection or related conditions in an infected cell, comprising contacting the cell with a compound or composition of the invention. The compounds and compositions are also useful for inhibiting the spread of Herpes virus. The method comprises contacting a Herpes virus infected cell of a cell population that also comprises uninfected cells thereby preventing the spread of Herpes virus from the infected cell to the uninfected cell. Thus, the compounds and compositions of the invention can be used to treat patients infected with Herpes virus.

The sixth aspect of the invention provides for a method of using the compounds of the invention as inhibitors for the side effects of vaccination.

The seventh aspect of the invention provides for a method of using the compounds of the invention as inhibitors of smallpox infection.

The eight aspect of the invention provides for a method of inhibiting poxvirus pathogenicity in a cell comprising contacting the cell infected with poxvirus with inhibitors of the ubiquitin ligase activity of the poxvirus p28 polypeptide. The cells include any cell that exhibits ubiquitin ligase activity, for example, macrophages. Thus, the compounds and compositions of the invention are useful in a method for treating patients infected with poxvirus, such as smallpox virus. The method comprises administering to the patient infected with poxvirus an inhibitor of the ubiquitin ligase activity of the p28 polypeptide. Preferably, administering the inhibitors of ubiquitin ligase to the patients is done before the appearance of the clinical symptoms of poxvirus infection. A preferred route of administering the inhibitors of ubiquitination to the patients is via a pill, but any suitable route can be used.

The compounds and compositions when used in the methods of the invention are useful to treat individuals who have been infected with poxviruses delivered from biological weapons. Particularly, individuals who are members of the military or healthcare workers can be effectively treated by the methods that use the compounds and compositions of the invention.

The compounds of the invention can be used in methods for screening compounds that possess antiviral activity. Examples of methods for screening for antiviral compounds are described in U.S. patent application 60/515,279 entitled "Methods and Compositions for the Identification of Anti-Poxvirus Agents," filed Oct. 28, 2003, which is incorporated by reference in its entirety.

Table 1 below illustrates certain preferred embodiments of the first aspect of the invention. We have found that the compounds listed in Table 1 are useful as inhibitors of ubiquitinization, as described more fully below, and, accordingly, inhibitors of viruses.

TABLE 1

| Cpd | Structure | Name |
|---|---|---|
| 1 | 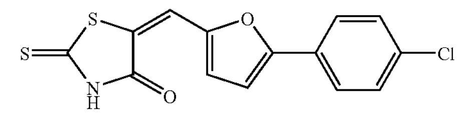  | (5E)-5-{[5-(4-chlorophenyl)-2-furyl]methylene}-2-thioxo-1,3-thiazolidin-4-one |
| 2 | 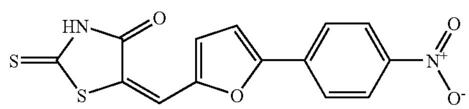  | (5E)-5-{[5-(4-nitrophenyl)-2-furyl]methylene}-2-thioxo-1,3-thiazolidin-4-one |
| 3 | 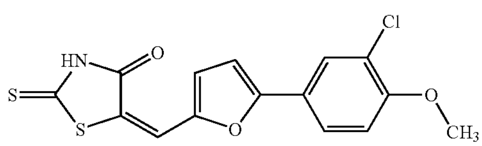  | (5E)-5-{[5-(3-chloro-4-methoxyphenyl)-2-furyl]methylene)-2-thioxo-1,3-thiazolidin-4-one |
| 4 | 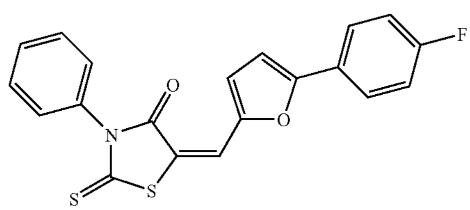  | (5E)-5-{[5-(4-fluorophenyl)-2-furyl]methylene}-3-phenyl-2-thioxo-1,3-thiazolidin-4-one |
| 5 | 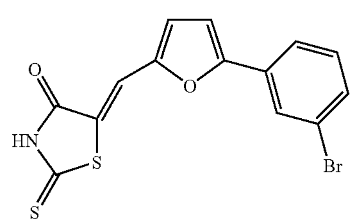  | (5Z)-5-{[5-(3-bromophenyl)-2-furyl]methylene}-2-thioxo-1,3-thiazolidin-4-one |
| 6 | 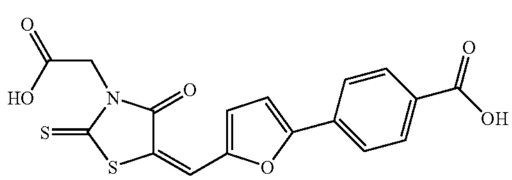  | 4-(5-{(E)-[3-(carboxymethyl)-4-oxo-2-thioxo-1,3-thiazolidin-5-ylidene]methyl}-2-furyl)benzoic acid |
| 7 | 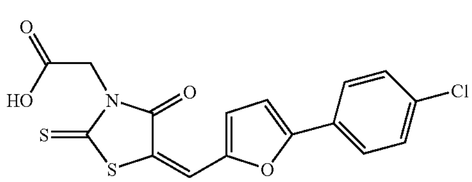  | ((5E)-5-{[5-(4-chlorophenyl)-2-furyl]methylene}-4-oxo-2-thioxo-1,3-thiazolidin-3-yl)acetic acid |

TABLE 1-continued

| Cpd | Structure | Name |
| --- | --- | --- |
| 8 | 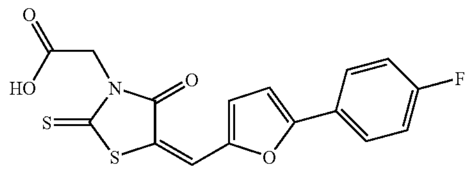 | ((5E-5-{[5-(4-fluorophenyl)-2-furyl]methylene}-4-oxo-2-thioxo-1,3-thiazolidin-3-yl)acetic acid |
| 9 | 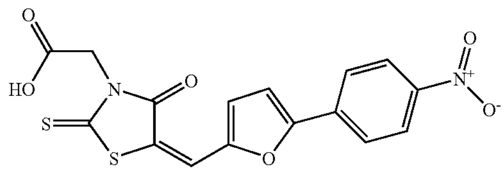 | ((5E)-5-{[5-(4-nitrophenyl)-2-furyl]methylene}-4-oxo-2-thioxo-1,3-thiazolidin-3-yl)acetic acid |
| 10 | 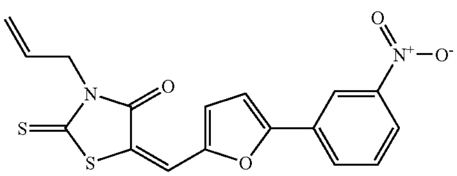 | (5E)-3-allyl-5-{[5-(3-nitrophenyl)-2-furyl]methylene}-2-thioxo-1,3-thiazolidin-4-one |
| 11 | 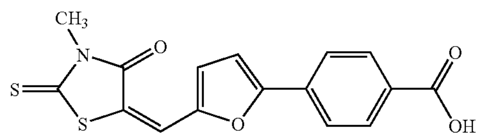 | 4-{5-[(E)-(3-methyl-4-oxo-2-thioxo-1,3-thiazolidin-5-ylidene)methyl]-2-furyl}benzoic acid |
| 12 | 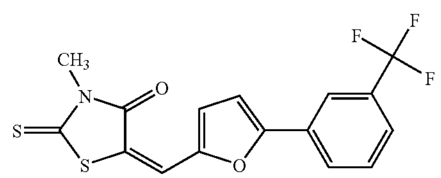 | (5E)-3-methyl-2-thioxo-5-({5-[3-(trifluoromethyl)phenyl]-2-furyl}methylene)-1,3-thiazolidin-4-one |
| 13 | 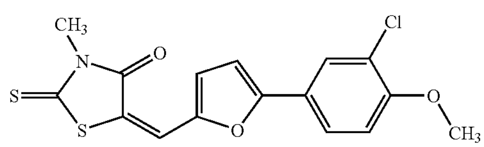 | (5E)-5-{[5-(3-chloro-4-methoxyphenyl)-2-furyl]methylene}-3-methyl-2-thioxo-1,3-thiazolidin-4-one |
| 14 | 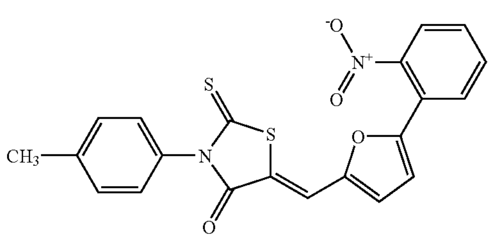 | (5Z)-3-(4-methylphenyl)-5-{[5-(2-nitrophenyl)-2-furyl]methylene}-2-thioxo-1,3-thiazolidin-4-one |
| 15 | 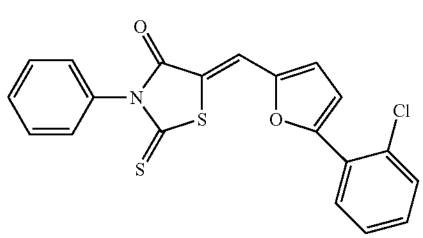 | (5Z)-5-{[5-(2-chlorophenyl)-2-furyl]methylene}-3-phenyl-2-thioxo-1,3-thiazolidin-4-one |

TABLE 1-continued

| Cpd | Structure | Name |
|---|---|---|
| 16 | 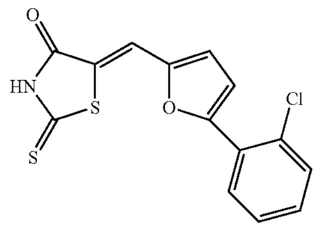 | (5Z)-5-{[5-(2-chlorophenyl)-2-furyl]methylene}-2-thioxo-1,3-thiazolidin-4-one |
| 17 | 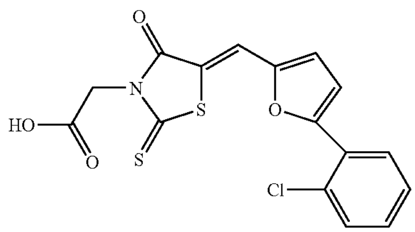 | ((5Z)-5-{[5-(2-chlorophenyl)-2-furyl]methylene}-4-oxo-2-thioxo-1,3-thiazolidin-3-yl)acetic acid |
| 18 | 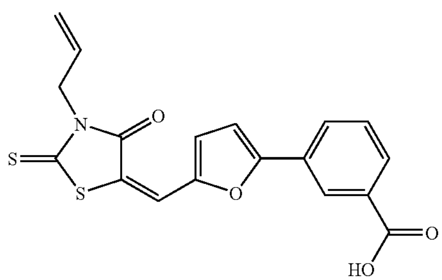 | 3-{5-[(E)-(3-allyl-4-oxo-2-thioxo-1,3-thiazolidin-5-ylidene)methyl]-2-furyl}benzoic acid |
| 19 | 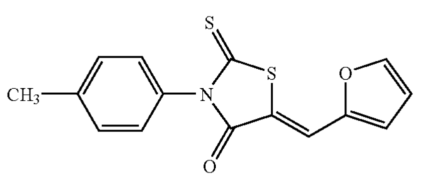 | (5Z)-5-(2-furylmethylene)-3-(4-methylphenyl)-2-thioxo-1,3-thiazolidin-4-one |
| 20 | 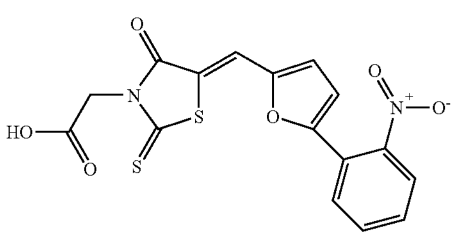 | ((5Z)-5-{[5-(2-nitrophenyl)-2-furyl]methylene}-4-oxo-2-thioxo-1,3-thiazolidin-3-yl)acetic acid |
| 21 | 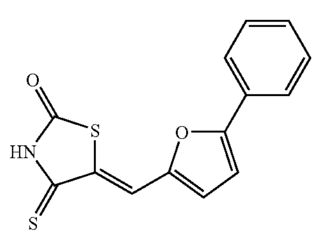 | (5Z)-5-[(5-phenyl-2-furyl)methylene]-2-thioxo-1,3-thiazolidin-4-one |
| 22 | 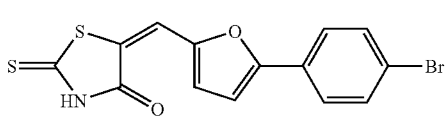 | (5E)-5-{[5-(4-bromophenyl)-2-furyl]methylene}-2-thioxo-1,3-thiazolidin-4-one |

TABLE 1-continued

| Cpd | Structure | Name |
|---|---|---|
| 23 | 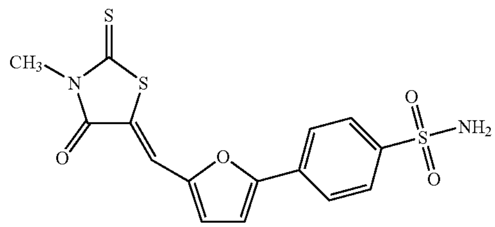 | 4-{5-[(Z)-(3-methyl-4-oxo-2-thioxo-1,3-thiazolidin-5-ylidene)methyl]-2-furyl}benzenesulfonamide |
| 24 | 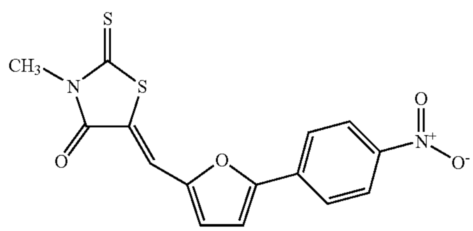 | (EZ)-3-methyl-5-{[5-(4-nitrophenyl)-2-furyl]methylene}-2-thioxo-1,3-thiazolidin-4-one |
| 25 | 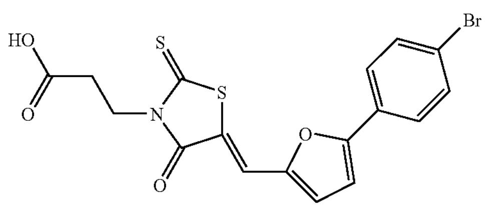 | 3-((5Z)-5-{[5-(4-bromophenyl)-2-furyl]methylene}-4-oxo-2-thioxo-1,3-thiazolidin-3-yl)propanoic acid |
| 26 | 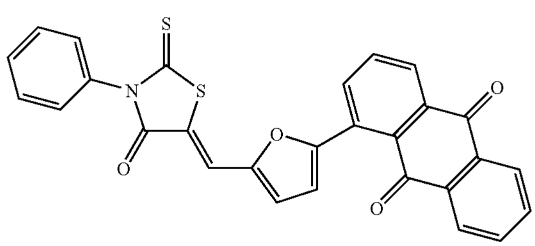 | 1-{5-[(Z)-(4-oxo-3-phenyl-2-thioxo-1,3-thiazolidin-5-ylidene)methyl]-2-furyl}anthra-9,10-quinone |
| 27 | 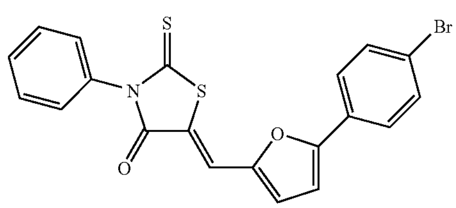 | (5Z)-5-{[5-(4-bromophenyl)-2-furyl]methylene}-3-phenyl-2-thioxo-1,3-thiazolidin-4-one |
| 28 | 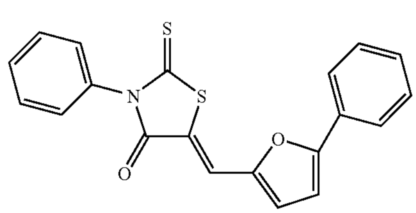 | (5Z)-3-phenyl-5-[(5-phenyl-2-furyl)methylene]-2-thioxo-1,3-thiazolidin-4-one |
| 29 | 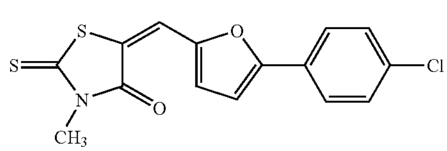 | (5E)-5-{[5-(4-chlorophenyl)-2-furyl]methylene}-3-methyl-2-thioxo-1,3-thiazolidin-4-one |

TABLE 1-continued

| Cpd | Structure | Name |
| --- | --- | --- |
| 30 | 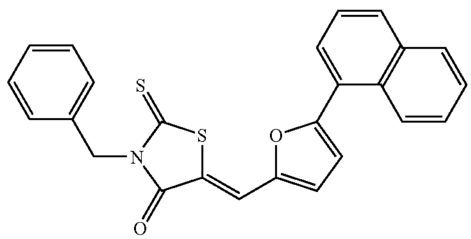 | (5Z)-3-benzyl-5-{[5-(1-naphthyl)-2-furyl]methylene}-2-thioxo-1,3-thiazolidin-4-one |
| 31 | 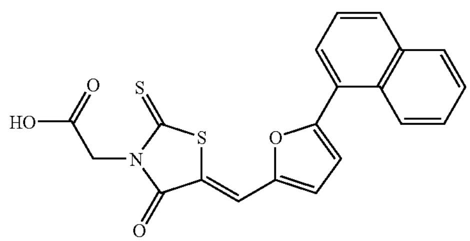 | ((5Z)-5-{[5-(1-naphthyl)-2-furyl[methylene}-4-oxo-2-thioxo-1,3-thiazolidin-3-yl)acetic acid |
| 32 | 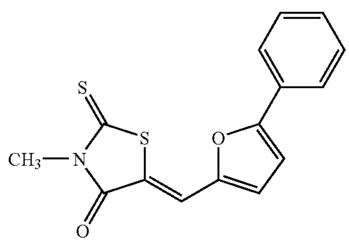 | (5Z)-3-methyl-5-[(5-phenyl-2-furyl)methylene]-2-thioxo-1,3-thiazolidin-4-one |
| 33 | 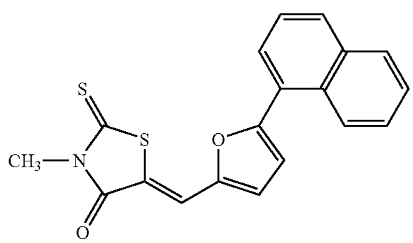 | (5Z)-3-methyl-5-{[5-(1-naphthyl)-2-furyl]methylene}-2-thioxo-1,3-thiazolidin-4-one |
| 34 | 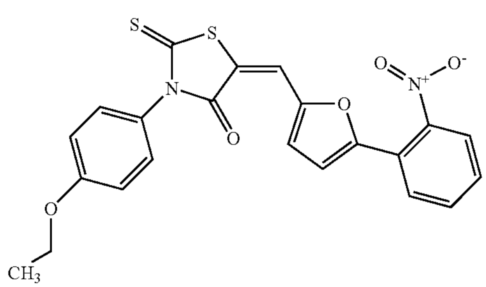 | (5E)-3-(4-ethoxyphenyl)-5-{[5-(2-nitrophenyl)-2-furyl]methylene}-2-thioxo-1,3-thiazolidin-4-one |
| 35 | 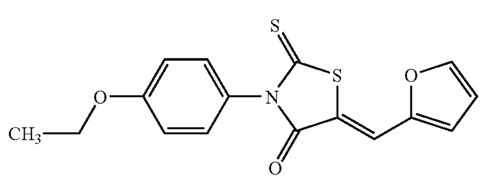 | (5Z)-3-(4-ethoxyphenyl)-5-(2-furylmethylene)-2-thioxo-1,3-thiazolidin-4-one |

TABLE 1-continued

| Cpd | Structure | Name |
|---|---|---|
| 36 | 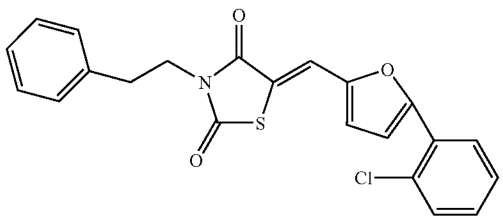 | (5Z)-5-{[5-(2-chlorophenyl)-2-furyl]methylene}-3-(2-phenylethyl)-2-thioxo-1,3-thiazolidin-4-one |
| 37 | 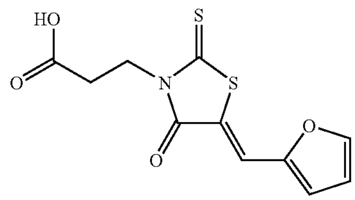 | 3-[(5Z)-5-(2-furylmethelene)-4-oxo-2-thioxo-1,3-thiazolidin-3-yl]propanoic acid |
| 38 | 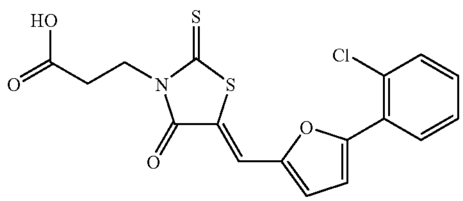 | 3-((5Z)-5-{[5-(2-chlorophenyl)-2-furyl]methylene}-4-oxo-2-thioxo-1,3-thiazolidin-3-yl)propanoic acid |
| 39 | 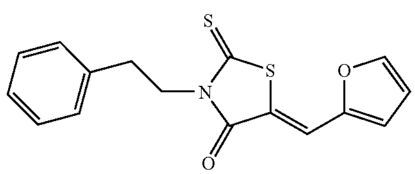 | (5Z)-5-(2-furylmethylene)-3-(2-phenylethyl)-2-thioxo-1,3-thiazolidin-4-one |
| 40 | 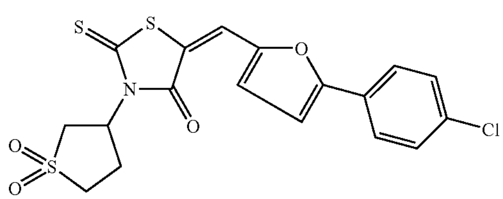 | (5E)-5-{[5-(4-chlorophenyl)-2-furyl]methylene}-3-(1,1-dioxidotetrahydro-3-thienyl)-2-thioxo-1,3-thiazolidin-4-one |
| 41 | 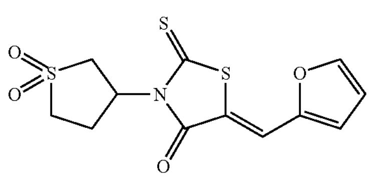 | (5Z)-3-(1,1-dioxidotetrahydro-3-thienyl)-5-(2-furylmethylene)-2-thioxo-1,3-thiazolidin-4-one |
| 42 | 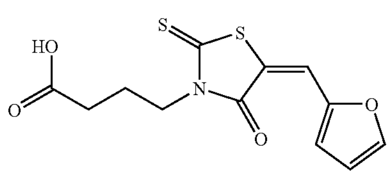 | 4-[(5E)-5-(2-furylmethylene)-4-oxo-2-thioxo-1,3-thiazolidin-3-yl]butanoic acid |
| 43 | 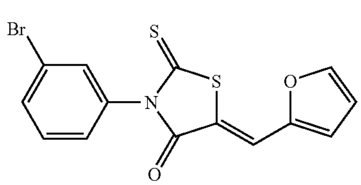 | (5Z)-3-(3-bromophenyl)-5-(2-furylmethylene)-2-thioxo-1,3-thiazolidin-4-one |

TABLE 1-continued

| Cpd | Structure | Name |
|---|---|---|
| 44 | 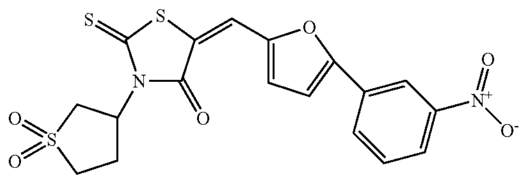 | (5E)-3-(1,1-dioxidotetrahydro-3-thienyl)-5-{[5-(3-nitrophenyl)-2-furyl]methylene}-2-thioxo-1,3-thiazolidin-4-one |
| 45 | 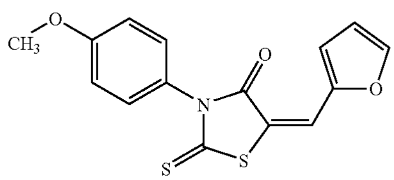 | (5E)-5-(2-furylmethylene)-3-(4-methoxyphenyl)-2-thioxo-1,3-thiazolidin-4-one |
| 46 | 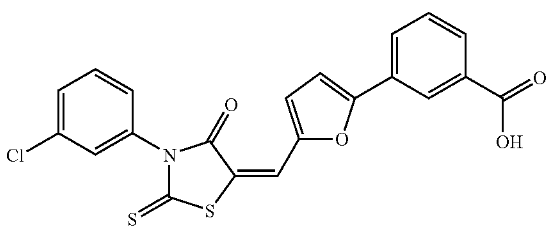 | 3-(5-{(E)-[3-(3-chlorophenyl)-4-oxo-2-thioxo-1,3-thiazolidin-5-ylidene]methyl}-2-furyl)benzoic acid |
| 47 | 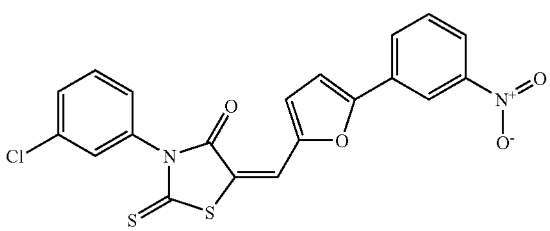 | (5E)-3-(3-chlorophenyl)-5-{[5-(3-nitrophenyl)-2-furyl]methylene}-2-thioxo-1,3-thiazolidin-4-one |
| 48 | 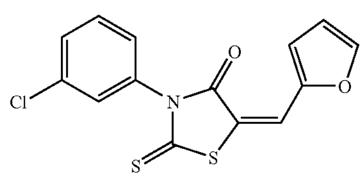 | (5E)-3-(3-chlorophenyl)-5-(2-furylmethylene)-2-thioxo-1,3-thiazolidin-4-one |
| 49 | 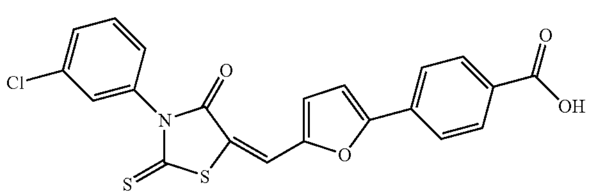 | 4-(5-{(E)-[3-(3-chlorophenyl)-4-oxo-2-thioxo-1,3-thiazolidin-5-ylidene]methyl}-2-furyl)benzoic acid |
| 50 | 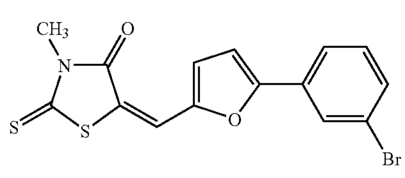 | (5E)-5-{[5-(3-bromophenyl)-2-furyl]methylene}-3-methyl-2-thioxo-1,3-thiazolidin-4-one |

TABLE 1-continued

| Cpd | Structure | Name |
|---|---|---|
| 51 | 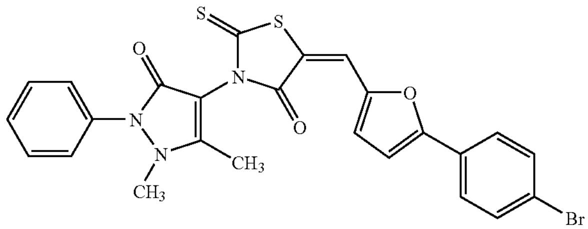 | (5E)-5-{[5-(4-bromophenyl)-2-furyl]methylene}-3-(1,5-dimethyl-3-oxo-2-phenyl-2,3-dihydro-1H-pyrazol-4-yl)-2-thioxo-1,3-thiazolidin-4-one |
| 52 | 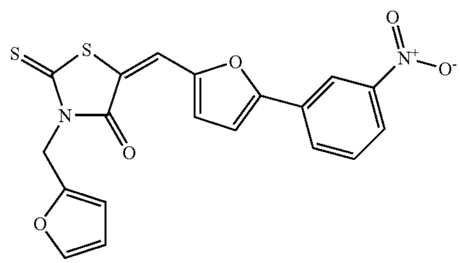 | (5E)-3-(2-furylmethyl)-5-{[5-(3-nitrophenyl)-2-furyl]methylene}-2-thioxo-1,3-thiazolidin-4-one |
| 53 | 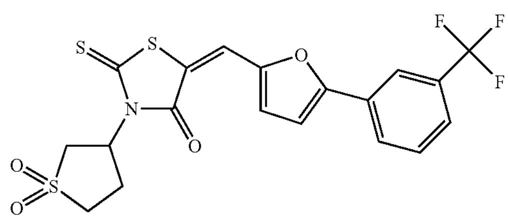 | (5E)-3-(1,1-dioxidotetrahydro-3-thienyl)-2-thioxo-5-({5-[3-(trifluoromethyl)phenyl]-2-furyl}methylene)-1,3-thiazolidin-4-one |
| 54 | 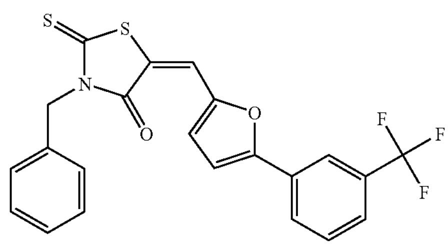 | (5E)-3-benzyl-2-thioxo-5-({5-[3-(trifluoromethyl)phenyl]-2-furyl}methylene)-1,3-thiazolidin-4-one |
| 55 | 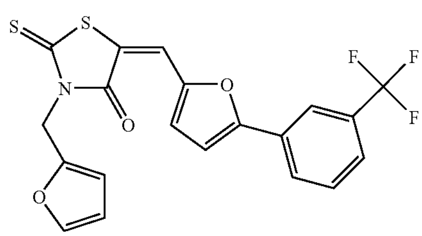 | (5E)-3-(2-furylmethyl)-2-thioxo-5-({5-[3-(trifluoromethyl)phenyl]-2-furyl}methylene)-1,3-thiazolidin-4-one |
| 56 | 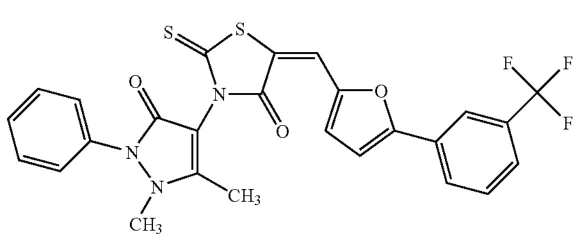 | (5E)-3-(1,5-dimethyl-3-oxo-2-phenyl-2,3-dihydro-1H-pyrazol-4-yl)-2-thioxo-5-({5-[3-(trifluoromethyl)phenyl]-2-furyl}methylene)-1,3-thiazolidin-4-one |

TABLE 1-continued

| Cpd | Structure | Name |
|---|---|---|
| 57 | 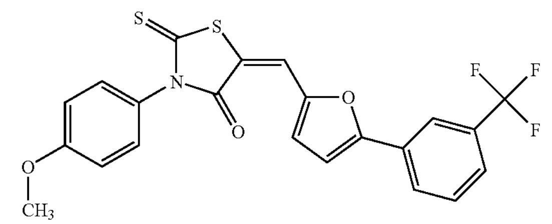 | (5E)-3-(4-methoxyphenyl)-2-thioxo-5-({5-[3-(trifluoromethyl)phenyl]-2-furyl}methylene)-1,3-thiazolidin-4-one |
| 58 | 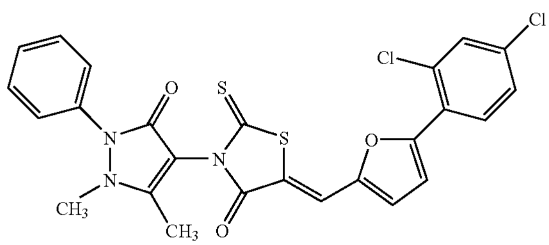 | (5Z)-5-{[5-(2,4-dichlorophenyl)-2-furyl]methylene}-3-(1,5-dimethyl-3-oxo-2-phenyl-2,3-dihydro-1H-pyrazol-4-yl)-2-thioxo-1,3-thiazolidin-4-one |
| 59 | 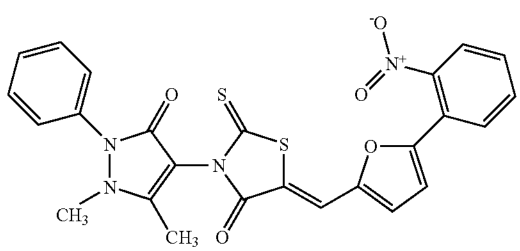 | (5Z)-3-(1,5-dimethyl-3-oxo-2-phenyl-2,3-dihydro-1H-pyrazol-4-yl)-5-{[5-(2-nitrophenyl)-2-furyl]methylene}-2-thioxo-1,3-thiazolidin-4-one |
| 60 | 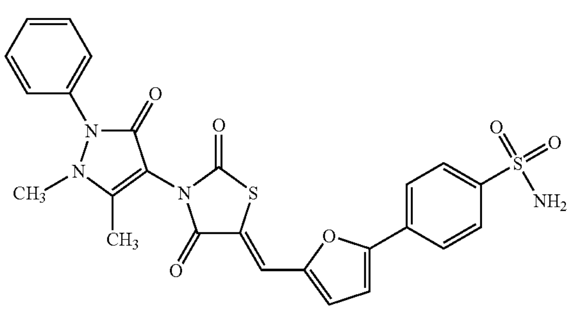 | 4-(5-{(Z)-[3-(1,5-dimethyl-3-oxo-2-phenyl-2,3-dihydro-1H-pyrazol-4-yl)-4-oxo-2-thioxo-1,3-thiazolidin-5-ylidene]methyl}-2-furyl)benzenesulfonamide |
| 61 | 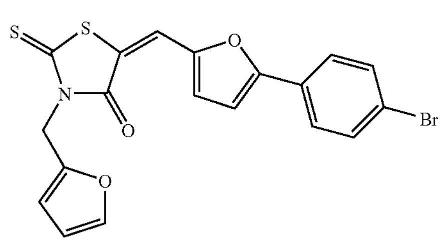 | (5E)-5-{[5-(4-bromophenyl)-2-furyl]methylene}-3-(2-furylmethyl)-2-thioxo-1,3-thiazolidin-4-one |
| 62 | 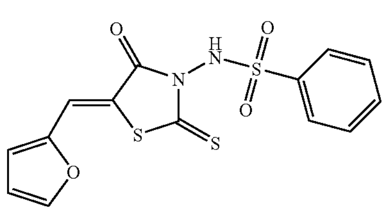 | N-[(5Z)-5-(2-furylmethylene)-4-oxo-2-thioxo-1,3-thiazolidin-3-yl]benzenesulfonamide |

TABLE 1-continued

| Cpd | Structure | Name |
|---|---|---|
| 63 | 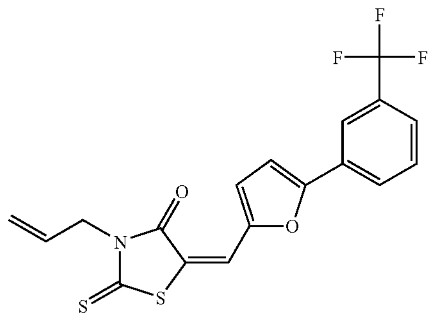 | (5E)-3-allyl-2-thioxo-5-({5-[3-(trifluoromethyl)phenyl]-2-furyl}methylene)-1,3-thiazolidin-4-one |
| 64 | 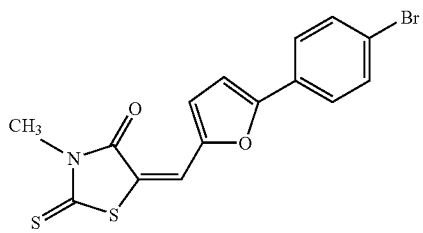 | (5E)-5-{[5-(4-bromophenyl)-2-furyl]methylene}-3-methyl-2-thioxo-1,3-thiazolidin-4-one |
| 65 | 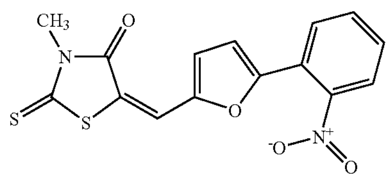 | (5E)-3-methyl-5-{[5-(2-nitrophenyl)-2-furyl]methylene}-2-thioxo-1,3-thiazolidin-4-one |
| 66 | 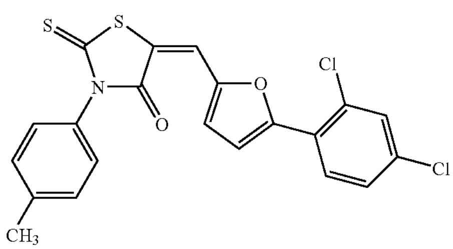 | (5E)-5-{[5-(2,4-dichlorophenyl)-2-furyl]methylene}-3-(4-methylphenyl)-2-thioxo-1,3-thiazolidin-4-one |
| 67 | 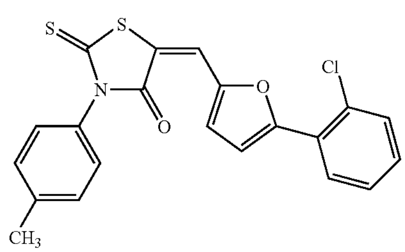 | (5E)-5-{[5-(2-chlorophenyl)-2-furyl]methylene}-3-(4-methylphenyl)-2-thioxo-1,3-thiazolidin-4-one |
| 68 | 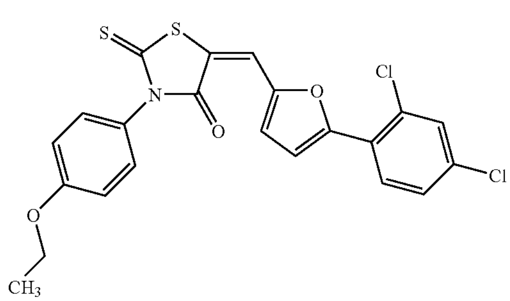 | (5E)-5-{[5-(2,4-dichlorophenyl)-2-furyl]methylene}-3-(4-ethoxyphenyl)-2-thioxo-1,3-thiazolidin-4-one |

TABLE 1-continued

| Cpd | Structure | Name |
|---|---|---|
| 69 | 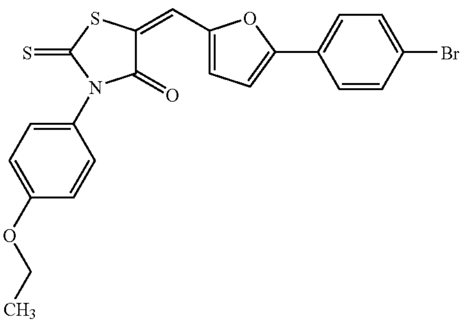 | (5E)-5-{[5-(4-bromophenyl)-2-furyl]methylene}-3-(4-ethoxyphenyl)-2-thioxo-1,3-thiazolidin-4-one |
| 70 | 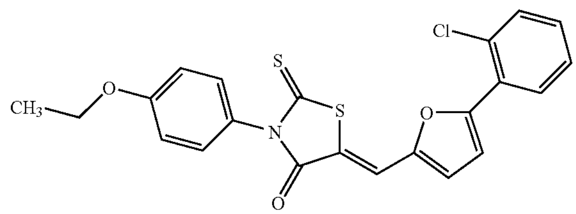 | (5Z)-5-{[5-(2-chlorophenyl)-2-furyl]methylene}-3-(4-ethoxyphenyl)-2-thioxo-1,3-thiazolidin-4-one |
| 71 | 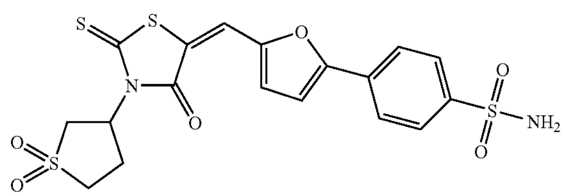 | 4-(5-{(E)-[3-(1,1-dioxidotetrahydro-3-thienyl)-4-oxo-2-thioxo-1,3-thiazolidin-5-ylidene]methyl}-2-furyl)benzenesulfonamide |
| 72 | 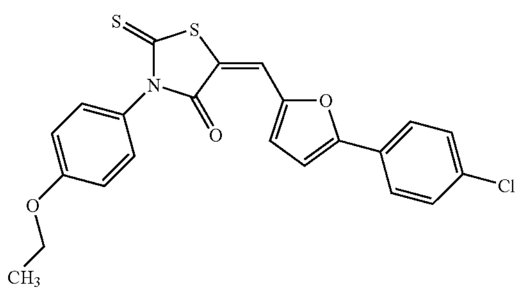 | (5E)-5-{[5-(4-chlorophenyl)-2-furyl]methylene}-3-(4-ethoxyphenyl)-2-thioxo-1,3-thiazolidin-4-one |
| 73 | 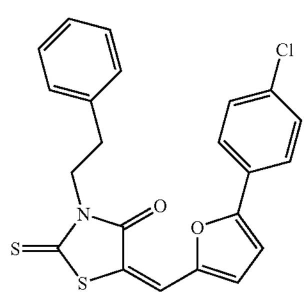 | (5E)-5-{[5-(4-chlorophenyl)-2-furyl]methylene}-3-(2-phenylethyl)-2-thioxo-1,3-thiazolidin-4-one |

TABLE 1-continued

| Cpd | Structure | Name |
|---|---|---|
| 74 | 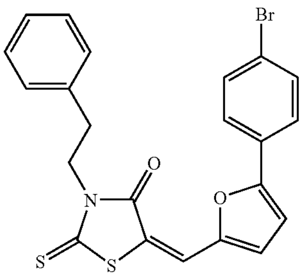 | (5E)-5-{[5-(4-bromophenyl)-2-furyl]methylene}-3-(2-phenylethyl)-2-thioxo-1,3-thiazolidin-4-one |
| 75 | 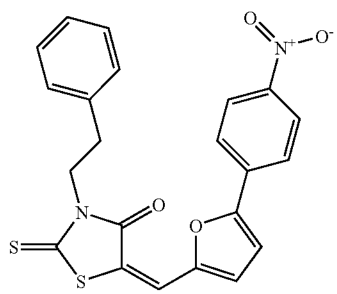 | (5E)-5-{[5-(4-nitrophenyl)-2-furyl]methylene}-3-(2-phenylethyl)-2-thioxo-1,3-thiazolidin-4-one |
| 76 | 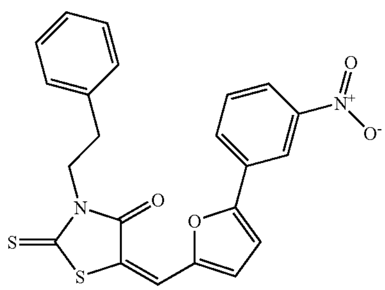 | (5E)-5-{[5-(3-nitrophenyl)-2-furyl]methylene}-3-(2-phenylethyl)-2-thioxo-1,3-thiazolidin-4-one |
| 77 | 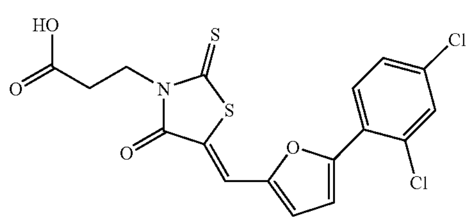 | 3-((5Z)-5-{[5-(2,4-dichlorophenyl)-2-furyl]methylene}-4-oxo-2-thioxo-1,3-thiazolidin-3-yl)propanoic acid |
| 78 | 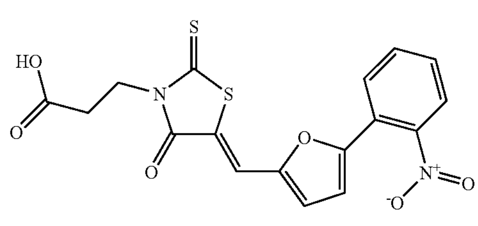 | 3-((5Z)-5-{[5-(2-nitrophenyl)-2-furyl]methylene}-4-oxo-2-thioxo-1,3-thiazolidin-3-yl)propanoic acid |
| 79 | 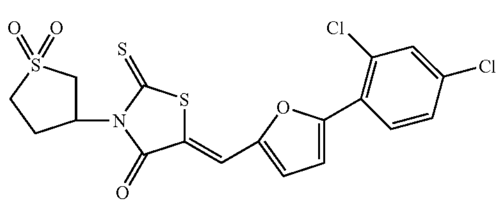 | (5Z)-5-{[5-(2,4-dichlorophenyl)-2-furyl]methylene}-3-(1,1-dioxidotetrahydro-3-thienyl)-2-thioxo-1,3-thiazolidin-4-one |

TABLE 1-continued

| Cpd | Structure | Name |
|---|---|---|
| 80 | 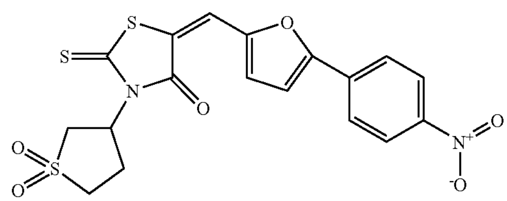 | (5E)-3-(1,1-dioxidotetrahydro-3-thienyl)-5-{[5-(4-nitrophenyl)-2-furyl]methylene}-2-thioxo-1,3-thiazolidin-4-one |
| 81 | 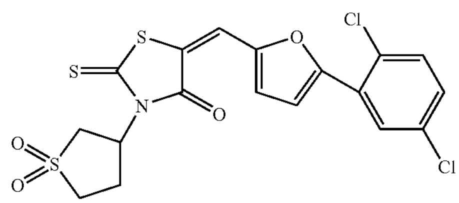 | (5E)-5-{[5-(2,5-dichlorophenyl)-2-furyl]methylene}-3-(1,1-dioxidotetrahydro-3-thienyl)-2-thioxo-1,3-thiazolidin-4-one |
| 82 | 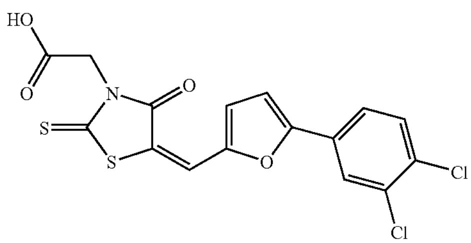 | ((5E)-5-{[5-(3,4-dichlorophenyl)-2-furyl]methylene}-4-oxo-2-thioxo-1,3-thiazolidin-3-yl)acetic acid |
| 83 | 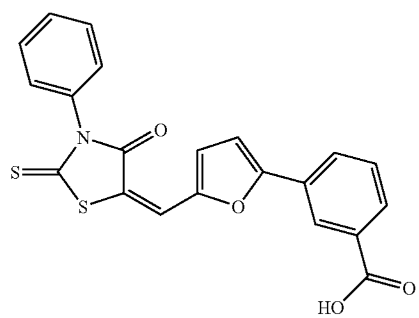 | 3-{5-[(E)-(4-oxo-3-phenyl-2-thioxo-1,3-thiazolidin-5-ylidene)methyl]-2-furyl}benzoic acid |
| 84 | 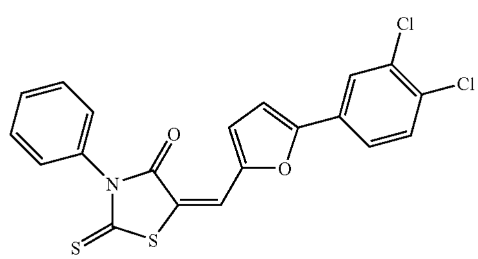 | (5E)-5-{[5-(3,4-dichlorophenyl)-2-furyl]methylene}-3-phenyl-2-thioxo-1,3-thiazolidin-4-one |
| 85 | 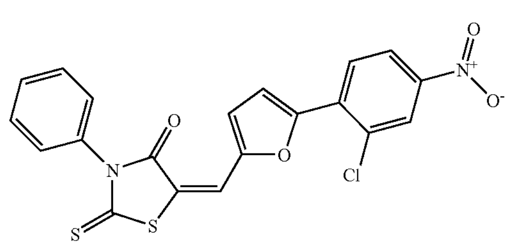 | (5E)-5-{[5-(2-chloro-4-nitrophenyl)-2-furyl]methylene}-3-phenyl-2-thioxo-1,3-thiazolidin-4-one |

TABLE 1-continued

| Cpd | Structure | Name |
|---|---|---|
| 86 | 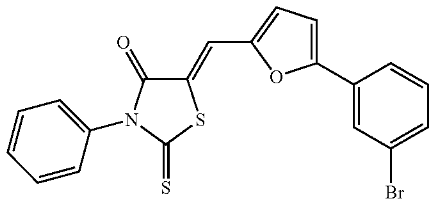 | (5Z)-5-{[5-(3-bromophenyl)-2-furyl]methylene}-3-phenyl-2-thioxo-1,3-thiazolidin-4-one |
| 87 | 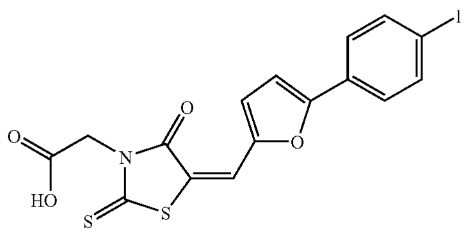 | ((5E)-5-{[5-(4-iodophenyl)-2-furyl]methylene}-4-oxo-2-thioxo-1,3-thiazolidin-3-yl)acetic acid |
| 88 | 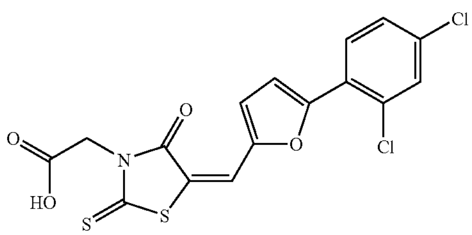 | ((5E)-5-{[5-(2,4-dichlorophenyl)-2-furyl]methylene}-4-oxo-2-thioxo-1,3-thiazolidin-3-yl)acetic acid |
| 89 | 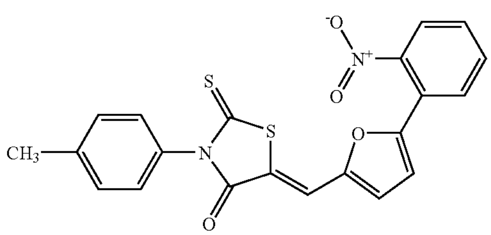 | (5Z)-3-(4-methylphenyl)-5-{[5-(2-nitrophenyl)-2-furyl]methylene}-2-thioxo-1,3-thiazolidin-4-one |
| 90 | 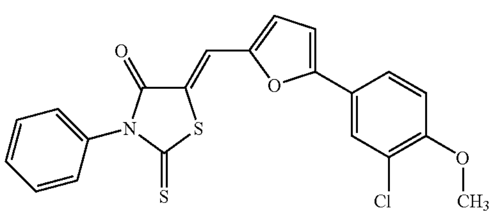 | (5Z)-5-{[5-(3-chloro-4-methoxyphenyl)-2-furyl]methylene}-3-phenyl-2-thioxo-1,3-thiazolidin-4-one |
| 91 | 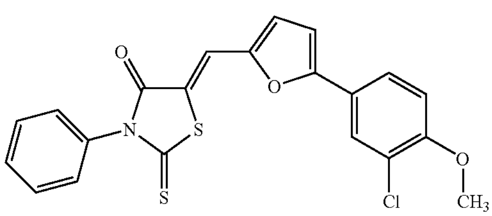 | (5Z)-5-{[5-(3-chloro-4-methoxyphenyl)-2-furyl]methylene}-3-phenyl-2-thioxo-1,3-thiazolidin-4-one |
| 92 | 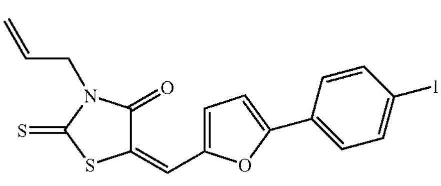 | (5E)-3-allyl-5-{[5-(4-iodophenyl)-2-furyl]methylene}-2-thioxo-1,3-thiazolidin-4-one |

TABLE 1-continued

| Cpd | Structure | Name |
|---|---|---|
| 93 | 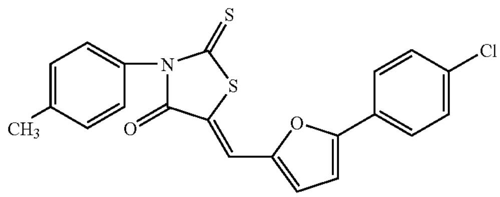 | (5Z)-5-{[5-(4-chlorophenyl)-2-furyl]methylene}-3-(4-methylphenyl)-2-thioxo-1,3-thiazolidin-4-one |
| 94 | 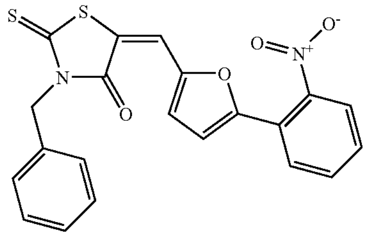 | (5E)-3-benzyl-5-{[5-(2-nitrophenyl)-2-furyl]methylene}-2-thioxo-1,3-thiazolidin-4-one |
| 95 | 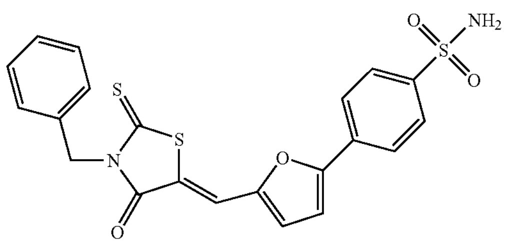 | 4-{5-[(Z)-(3-benzyl-4-oxo-2-thioxo-1,3-thiazolidin-5-ylidene)methyl]-2-furyl}benzenesulfonamide |
| 96 | 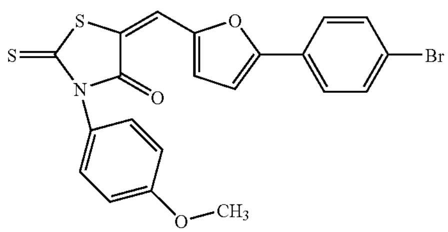 | (5E)-5-{[5-(4-bromophenyl)-2-furyl]methylene}-3-(4-methoxyphenyl)-2-thioxo-1,3-thiazolidin-4-one |
| 97 | 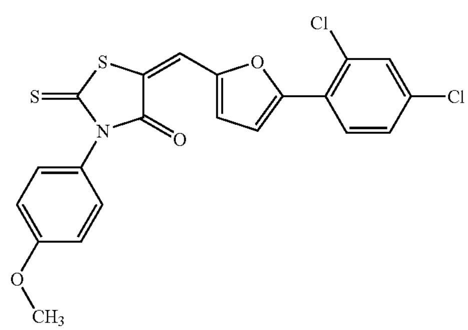 | (5E)-5-{[5-(2,4-dichlorophenyl)-2-furyl]methylene}-3-(4-methoxyphenyl)-2-thioxo-1,3-thiazolidin-4-one |
| 98 | 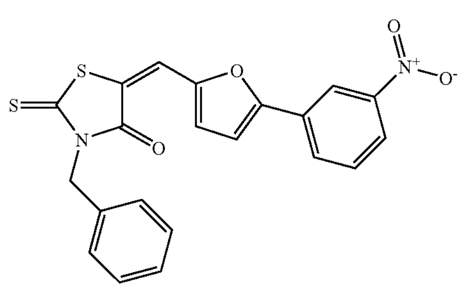 | (5E)-3-benzyl-5-{[5-(3-nitrophenyl)-2-furyl]methylene}-2-thioxo-1,3-thiazolidin-4-one |

TABLE 1-continued

| Cpd | Structure | Name |
|---|---|---|
| 99 | 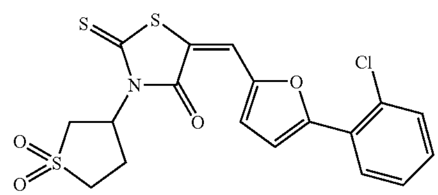 | (5E)-5-{[5-(2-chlorophenyl)-2-furyl]methylene}-3-(1,1-dioxidotetrahydro-3-thienyl)-2-thioxo-1,3-thiazolidin-4-one |
| 100 | 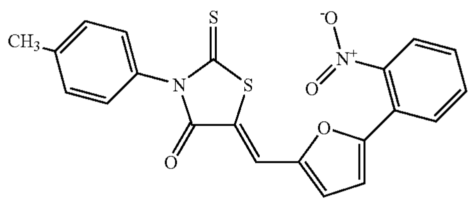 | (5Z)-3-(4-methylphenyl)-5-{[5-(2-nitrophenyl)-2-furyl]methylene}-2-thioxo-1,3-thiazolidin-4-one |
| 101 | 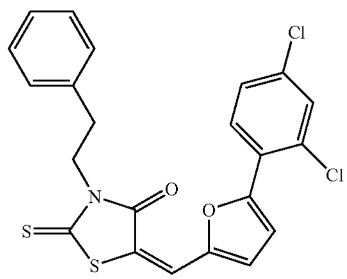 | (5E)-5-{[5-(2,4-dichlorophenyl)-2-furyl]methylenel-3-(2-phenylethyl)-2-thioxo-1,3-thiazolidin-4-one |
| 102 | 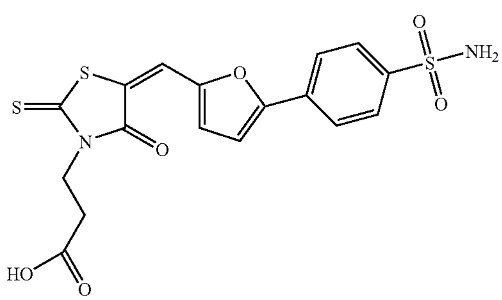 | 3-[(5E)-5-({5-[4-(aminosulfonyl)phenyl]-2-furyl}methylene)-4-oxo-2-thioxo-1,3-thiazolidin-3-yl]propanoic acid |
| 103 | 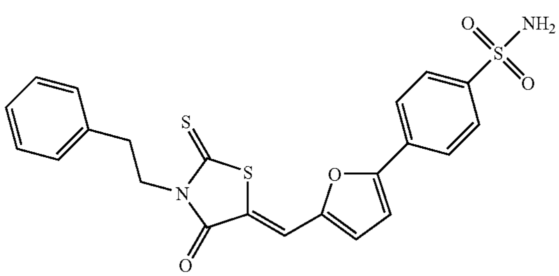 | 4-(5-{(Z)-[4-oxo-3-(2-phenylethyl)-2-thioxo-1,3-thiazolidin-5-ylidene]methyl}-2-furyl)benzenesulfonamide |
| 104 | 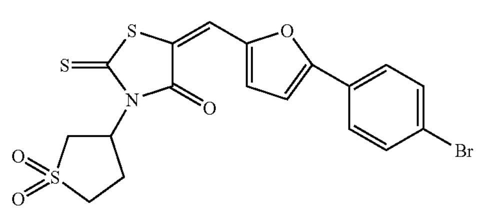 | (5E)-5-{[5-(4-bromophenyl)-2-furyl]methylene}-3-(1,1-dioxidotetrahydro-3-thienyl)-2-thioxo-1,3-thiazolidin-4-one |

TABLE 1-continued

| Cpd | Structure | Name |
|---|---|---|
| 105 | 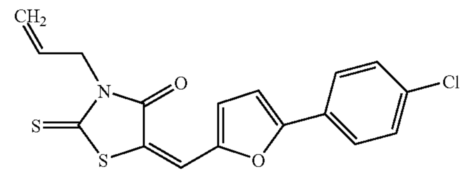 | (5E)-3-allyl-5-{[5-(4-chlorophenyl)-2-furyl]methylene}-2-thioxo-1,3-thiazolidin-4-one |
| 106 | 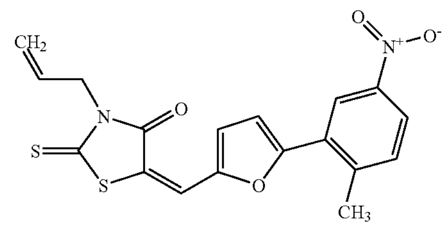 | (5E)-3-allyl-5-{[5-(2-methyl-5-nitrophenyl)-2-furyl]methylene}-2-thioxo-1,3-thiazolidin-4-one |
| 107 | 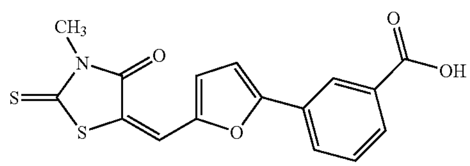 | 3-{5-[(E)-(3-methyl-4-oxo-2-thioxo-1,3-thiazolidin-5-ylidene)methyl]-2-furyl}benzoic acid |
| 108 | 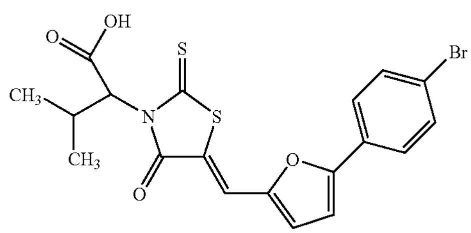 | 2-((5Z)-5-{[5-(4-bromophenyl)-2-furyl]methylene}-4-oxo-2-thioxo-1,3-thiazolidin-3-yl)-3-methylbutanoic acid |
| 109 | 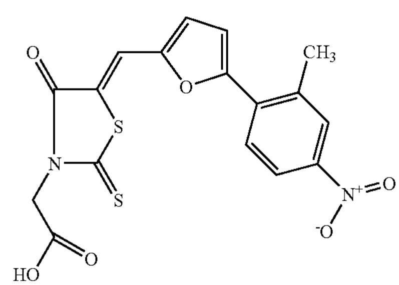 | ((5Z)-5-{[5-(2-methyl-4-nitrophenyl)-2-furyl]methylene}-4-oxo-2-thioxo-1,3-thiazolidin-3-yl)acetic acid |
| 110 | 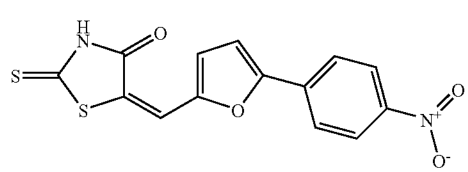 | (5E)-5-{[5-(4-nitrophenyl)-2-furyl]methylene}-2-thioxo-1,3-thiazolidin-4-one |
| 111 | 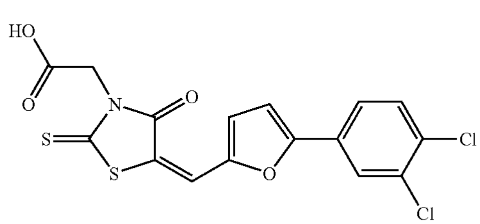 | ((5E)-5-{[5-(3,4-dichlorophenyl)-2-furyl]methylene}-4-oxo-2-thioxo-1,3-thiazolidin-3-yl)acetic acid |

TABLE 1-continued

| Cpd | Structure | Name |
|---|---|---|
| 112 | 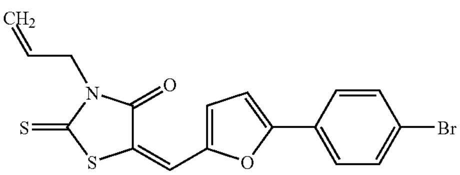 | (5E)-3-allyl-5-{[5-(4-bromophenyl)-2-furyl]methylene}-2-thioxo-1,3-thiazolidin-4-one |
| 113 | 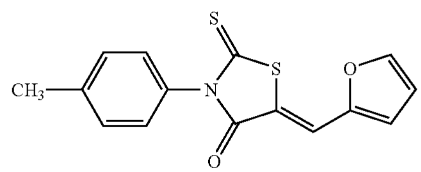 | (5Z)-5-(2-furylmethylene)-3-(4-methylphenyl)-2-thioxo-1,3-thiazolidin-4-one |
| 114 | 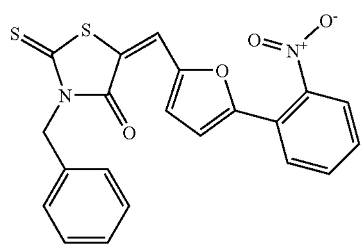 | (5E)-3-benzyl-5-{[5-(2-nitrophenyl)-2-furyl]methylene}-2-thioxo-1,3-thiazolidin-4-one |
| 115 | 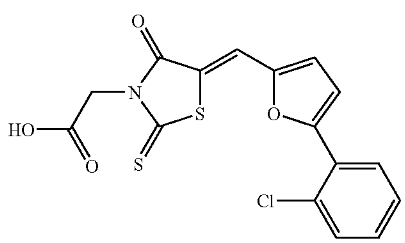 | ((5Z)-5-{[5-(2-chlorophenyl)-2-furyl]methylene}-4-oxo-2-thioxo-1,3-thiazolidin-3-yl)acetic acid |
| 116 | 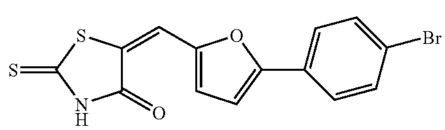 | (5E)-5-{[5-(4-bromophenyl)-2-furyl]methylene}-2-thioxo-1,3-thiazolidin-4-one |
| 117 | 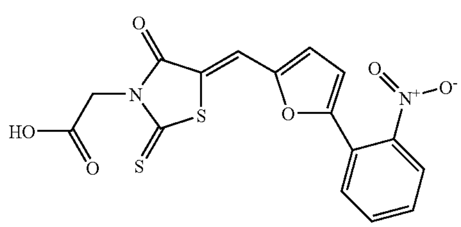 | ((5Z)-5-{[5-(2-nitrophenyl)-2-furyl]methylene}-4-oxo-2-thioxo-1,3-thiazolidin-3-yl)acetic acid |
| 118 | 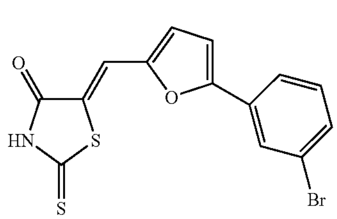 | (5Z)-5-{[5-(3-bromophenyl)-2-furyl]methylene}-2-thioxo-1,3-thiazolidin-4-one |

TABLE 1-continued

| Cpd | Structure | Name |
|---|---|---|
| 119 | 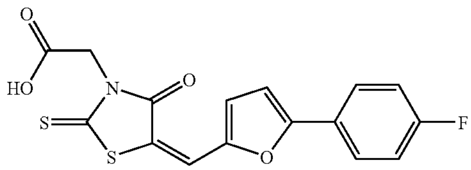 | ((5E)-5-{[5-(4-fluorophenyl)-2-furyl]methylene}-4-oxo-2-thioxo-1,3-thiazolidin-3-yl)acetic acid |
| 120 | 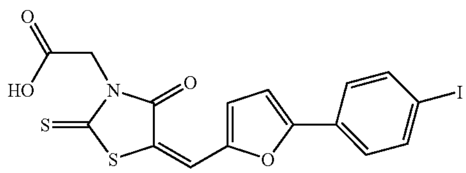 | ((5E)-5-{[5-(4-iodophenyl)-2-furyl]methylene}-4-oxo-2-thioxo-1,3-thiazolidin-3-yl)acetic acid |
| 121 | 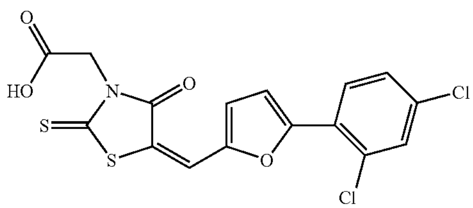 | ((5E)-5-{[5-(2,4-dichlorophenyl)-2-furyl]methylene}-4-oxo-2-thioxo-1,3-thiazolidin-3-yl)acetic acid |
| 122 | 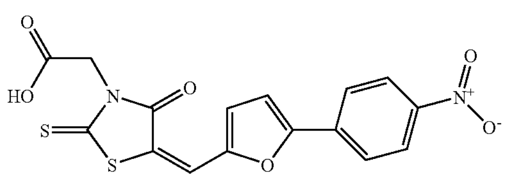 | ((5E)-5-{[5-(4-nitrophenyl)-2-furyl]methylene}-4-oxo-2-thioxo-1,3-thiazolidin-3-yl)acetic acid |
| 123 | 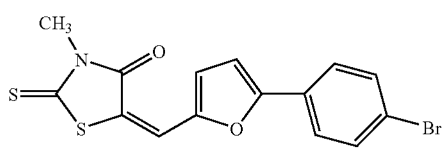 | (5E)-5-{[5-(4-bromophenyl)-2-furyl]methylene}-3-methyl-2-thioxo-1,3-thiazolidin-4-one |
| 124 | 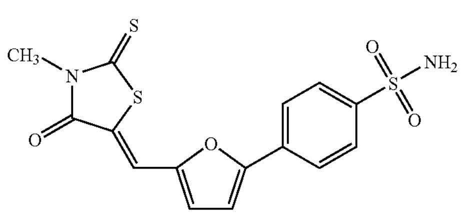 | 4-{5-[(Z)-(3-methyl-4-oxo-2-thioxo-1,3-thiazolidin-5-ylidene)methyl]-2-furyl}benzenesulfonamide |
| 125 | 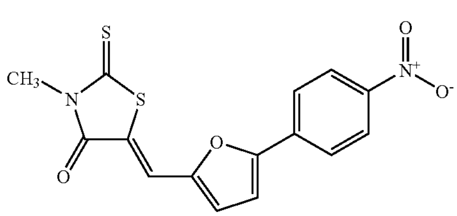 | (5Z)-3-methyl-5-{[5-(4-nitrophenyl-2-furyl]methylene}-2-thioxo-1,3-thiazolidin-4-one |

TABLE 1-continued

| Cpd | Structure | Name |
|---|---|---|
| 126 | 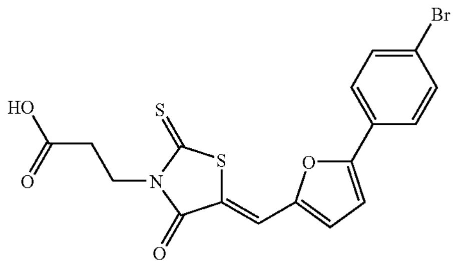 | 3-((5Z)-5-{[5-(4-bromophenyl)-2-furyl]methylene}-4-oxo-2-thioxo-1,3-thiazolidin-3-yl)propanoic acid |
| 127 | 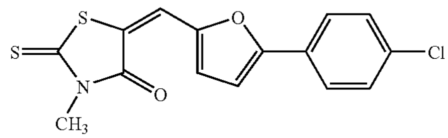 | (5E)-5-{[5-(4-chlorophenyl)-2-furyl]methylene}-3-methyl-2-thioxo-1,3-thiazolidin-4-one |
| 128 | 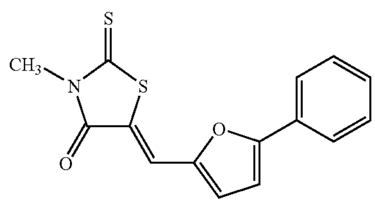 | (5Z)-3-methyl-5-[(5-phenyl-2-furyl)methylene]-2-thioxo-1,3-thiazolidin-4-one |
| 129 | 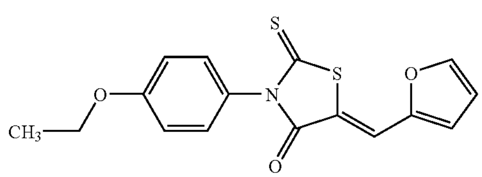 | (5Z)-3-(4-ethoxyphenyl)-5-(2-furylmethylene)-2-thioxo-1,3-thiazolidin-4-one |
| 130 | 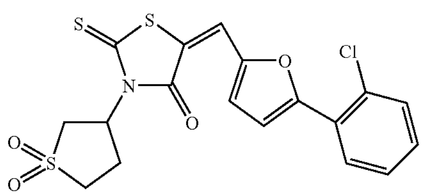 | (5E)-5-{[5-(2-chlorophenyl)-2-furyl]methylene}-3-(1,1-dioxidotetrahydro-3-thienyl)-2-thioxo-1,3-thiazolidin-4-one |
| 131 | 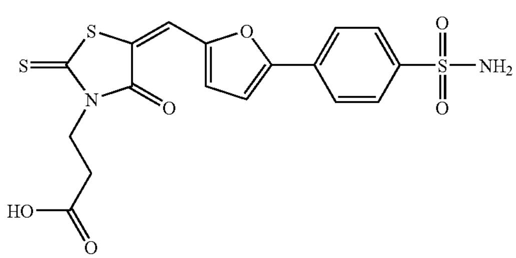 | 3-[(5E)-5-({5-[4-(aminosulfonyl)phenyl]-2-furyl}methylene)-4-oxo-2-thioxo-1,3-thiazolidin-3-yl]propanoic acid |
| 132 | 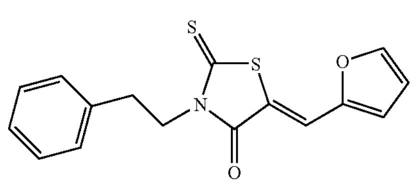 | (5Z)-5-(2-furylmethylene)-3-(2-phenylethyl)-2-thioxo-1,3-thiazolidin-4-one |

TABLE 1-continued

| Cpd | Structure | Name |
|---|---|---|
| 133 | 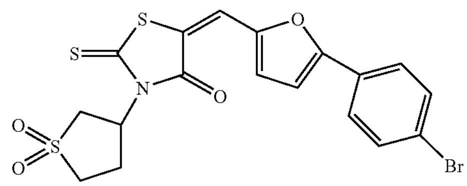 | (5E)-5-{[5-(4-bromophenyl)-2-furyl]methylene}-3-(1,1-dioxidotetrahydro-3-thienyl)-2-thioxo-1,3-thiazolidin-4-one |
| 134 | 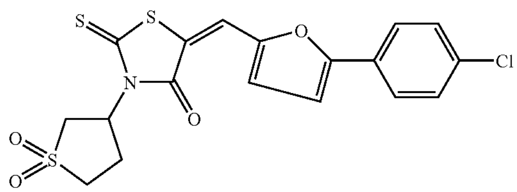 | (5E)-5-{[5-(4-chlorophenyl)-2-furyl]methylene}-3-(1,1-dioxidotetrahydro-3-thienyl)-2-thioxo-1,3-thiazolidin-4-one |
| 135 | 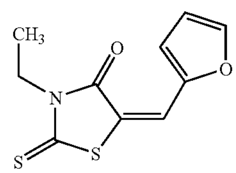 | (5E)-3-ethyl-5-(2-furylmethylene)-2-thioxo-1,3-thiazolidin-4-one |
| 136 | 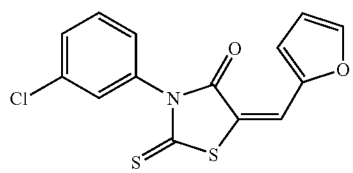 | (5E)-3-(3-chlorophenyl)-5-(2-furylmethylene)-2-thioxo-1,3-thiazolidin-4-one |
| 137 | 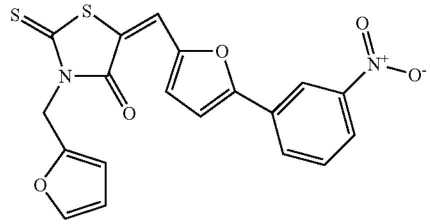 | (5E)-3-(2-furylmethyl)-5-([5-(3-nitrophenyl)-2-furyl]methylene}-2-thioxo-1,3-thiazolidin-4-one |
| 138 | 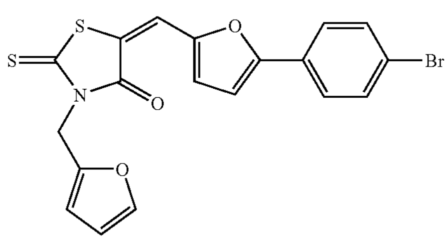 | (5E)-5-{[5-(4-bromophenyl)-2-furyl]methylene}-3-(2-furylmethyl)-2-thioxo-1,3-thiazolidin-4-one |
| 139 | 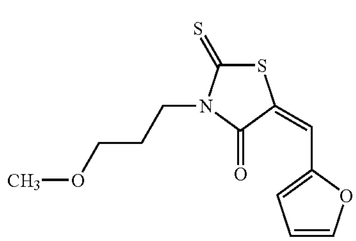 | (5E)-5-(2-furylmethylene)-3-(3-methoxypropyl)-2-thioxo-1,3-thiazolidin-4-one |

TABLE 1-continued

| Cpd | Structure | Name |
| --- | --- | --- |
| 140 | 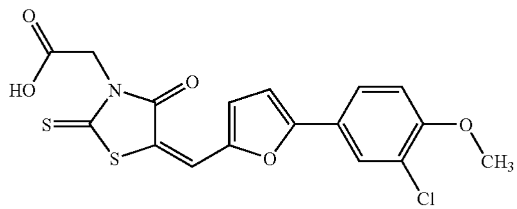 | ((5E)-5-{[5-(3-chloro-4-methoxyphenyl)-2-furyl]methylene}-4-oxo-2-thioxo-1,3-thiazolidin-3-yl)acetic acid |
| 141 | 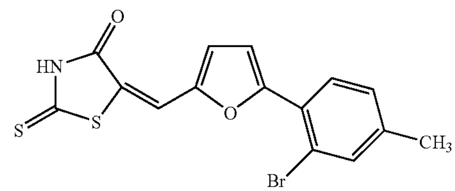 | (5E)-5-{[5-(2-bromo-4-methylphenyl)-2-furyl]methylene}-2-thioxo-1,3-thiazolidin-4-one |
| 142 | 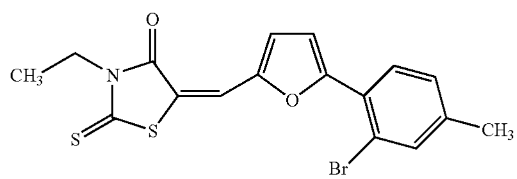 | (5E)-5-{[5-(2-bromo-4-methylphenyl)-2-furyl)methylene}-3-ethyl-2-thioxo-1,3-thiazolidin-4-one |
| 143 | 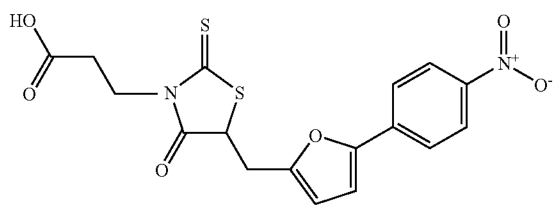 | 3-((5Z)-5-{[5-(4-nitrophenyl)-2-furyl]methylene)-4-oxo-2-thioxo-1,3-thiazolidin-3-yl)propanoic acid |
| 144 | 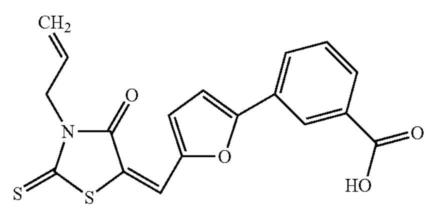 | 3-{5-[(E)-(3-allyl-4-oxo-2-thioxo-1,3-thiazolidin-5-ylidene)methyl]-2-furyl}benzoic acid |
| 145 | 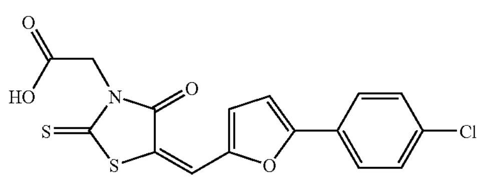 | ((5E)-5-{[5-(4-chlorophenyl)-2-furyl]methylene}-4-oxo-2-thioxo-1,3-thiazolidin-3-yl)acetic acid |
| 146 | 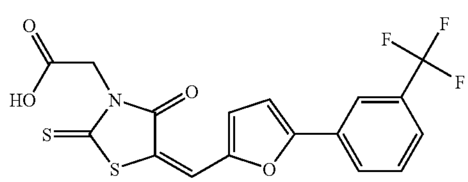 | [(5E)-4-oxo-2-thioxo-5-({5-[3-(trifluoromethyl)phenyl]-2-furyl}methylene)-1,3-thiazolidin-3-yl]acetic acid |
| 147 | 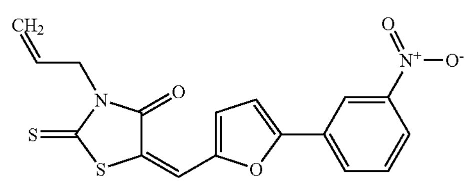 | (5E)-3-allyl-5-{[5-(3-nitrophenyl)-2-furyl]methylene}-2-thioxo-1,3-thiazolidin-4-one |

TABLE 1-continued

| Cpd | Structure | Name |
|---|---|---|
| 148 | 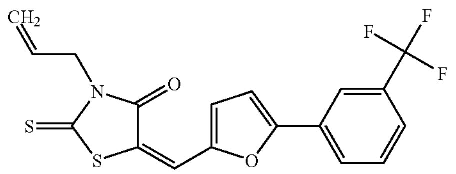 | (5E)-3-allyl-2-thioxo-5-({5-[3-(trifluoromethyl)phenyl]-2-furyl}methylene)-1,3-thiazolidin-4-one |
| 149 | 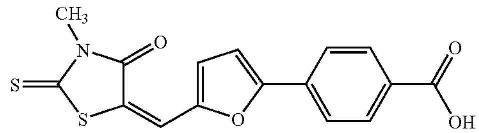 | 4-{5-[(E)-(3-methyl-4-oxo-2-thioxo-1,3-thiazolidin-5-ylidene)methyl]-2-furyl}benzoic acid |
| 150 | 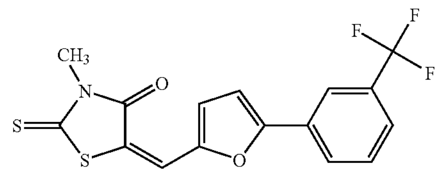 | (5E)-3-methyl-2-thioxo-5-({5-[3-(trifluoromethyl)phenyl]-2-furyl}methylene)-1,3-thiazolidin-4-one |
| 151 | 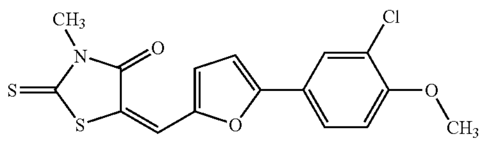 | (5E)-5-{[5-(3-chloro-4-methoxyphenyl)-2-furyl]methylene}-3-methyl-2-thioxo-1,3-thiazolidin-4-one |
| 152 | 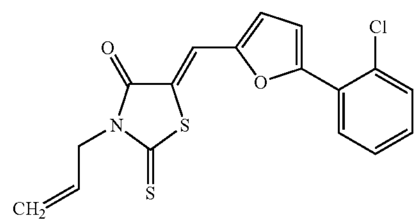 | (5Z)-5-{[5-(2-chlorophenyl)-2-furyl]methylene}-3-propyl-2-thioxo-1,3-thiazolidin-4-one |
| 153 | 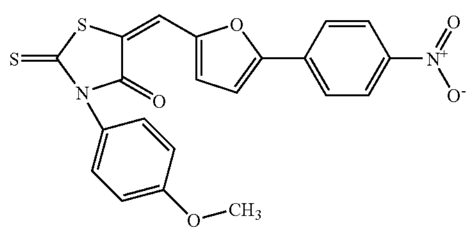 | (5E)-3-(4-methoxyphenyl)-5-{[5-(4-nitrophenyl)-2-furyl]methylene}-2-thioxo-1,3-thiazolidin-4-one |
| 154 | 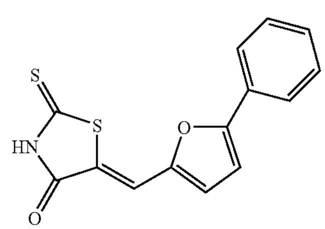 | (5Z)-5-[(5-phenyl-2-furyl)methylene]-2-thioxo-1,3-thiazolidin-4-one |
| 155 | 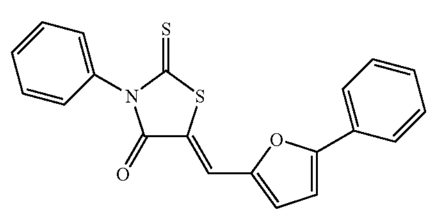 | (5Z)-3-phenyl-5-[(5-phenyl-2-furyl)methylene]-2-thioxo-1,3-thiazolidin-4-one |

| Cpd | Structure | Name |
|---|---|---|
| 156 | 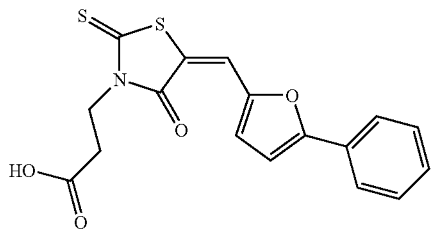 | 3-{(5E)-4-oxo-5-[(5-phenyl-2-furyl)methylene]-2-thioxo-1,3-thiazolidin-3-yl}propanoic acid |
| 157 | 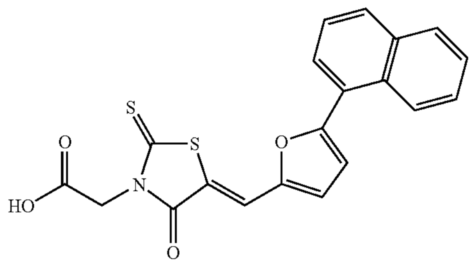 | ((5Z)-5-{[5-(1-naphthyl)-2-furyl]methylene}-4-oxo-2-thioxo-1,3-thiazolidin-3-yl)acetic acid |
| 158 | 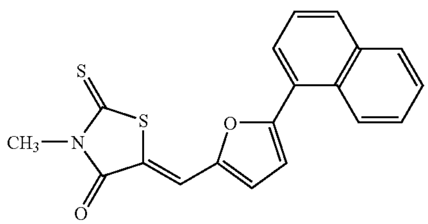 | (5Z)-3-methyl-5-{[5-(1-naphthyl)-2-furyl]methylene}-2-thioxo-1,3-thiazolidin-4-one |
| 159 | 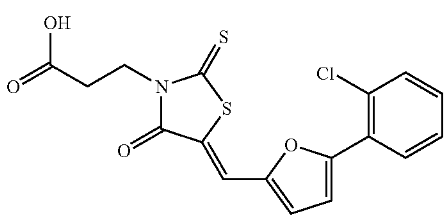 | 3-((5Z)-5-{[5-(2-chlorophenyl)-2-furyl]methylene}-4-oxo-2-thioxo-1,3-thiazolidin-3-yl)propanoic acid |
| 160 | 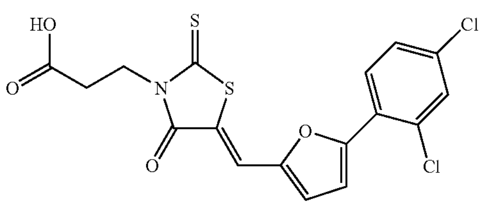 | 3-((5Z)-5-{[5-(2,4-dichlorophenyl)-2-furyl]methylene}-4-oxo-2-thioxo-1,3-thiazolidin-3-yl)propanoic acid |
| 161 | 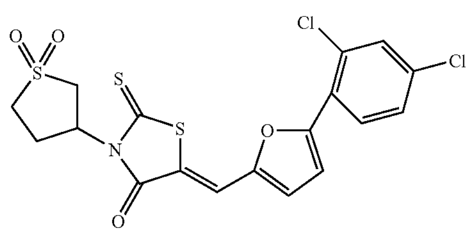 | (5Z)-5-{[5-(2,4-dichlorophenyl)-2-furyl]methylene}-3-(1,1-dioxidotetrahydro-3-thienyl)-2-thioxo-1,3-thiazolidin-4-one |
| 162 | 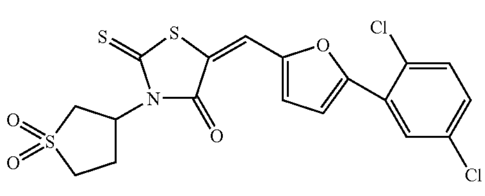 | (5E)-5-{[5-(2,5-dichlorophenyl)-2-furyl]methylene}-3-(1,1-dioxidotetrahydro-3-thienyl)-2-thioxo-1,3-thiazolidin-4-one |

TABLE 1-continued

| Cpd | Structure | Name |
| --- | --- | --- |
| 163 | 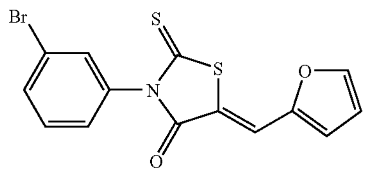 | (5Z)-3-(3-bromophenyl)-5-(2-furylmethylene)-2-thioxo-1,3-thiazolidin-4-one |
| 164 | 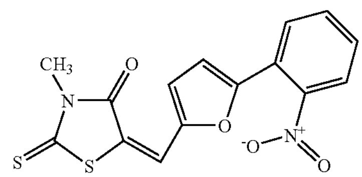 | (5E)-3-methyl-5-{[5-(2-nitrophenyl)-2-furyl]methylene}-2-thioxo-1,3-thiazolidin-4-one |
| 165 | 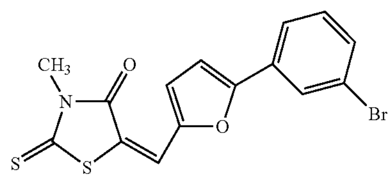 | (5E)-5-{[5-(3-bromophenyl)-2-furyl]methylene}-3-methyl-2-thioxo-1,3-thiazolidin-4-one |
| 166 | 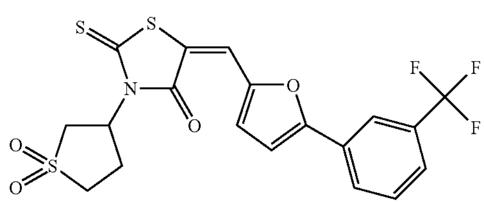 | (5E)-3-(1,1-dioxidotetrahydro-3-thienyl)-2-thioxo-5-({5-[3-(trifluoromethyl)phenyl]-2-furyl}methylene)-1,3-thiazolidin-4-one |
| 167 | 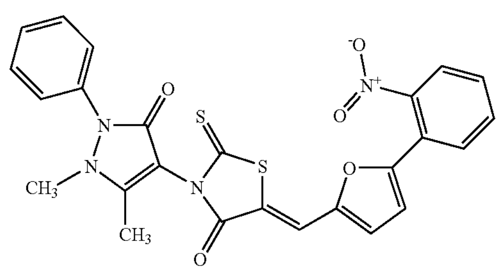 | (5Z)-3-(1,5-dimethyl-3-oxo-2-phenyl-2,3-dihydro-1H-pyrazol-4-yl)-5-{[5-(2-nitrophenyl)-2-furyl]methylene}-2-thioxo-1,3-thiazolidin-4-one |
| 168 | 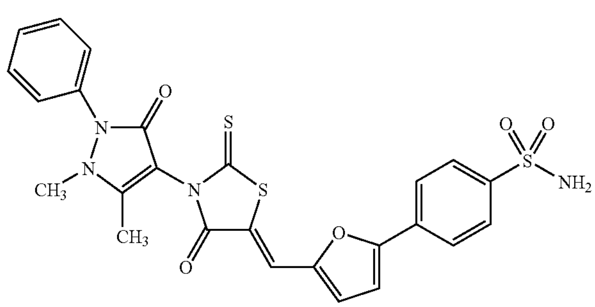 | 4-(5-((Z)-[3-(1,5-dimethyl-3-oxo-2-phenyl-2,3-dihydro-1H-pyrazol-4-yl)-4-oxo-2-thioxo-1,3-thiazolidin-5-ylidene]methyl}-2-furyl)benzenesulfonamide |

TABLE 1-continued

| Cpd | Structure | Name |
|-----|-----------|------|
| 169 | 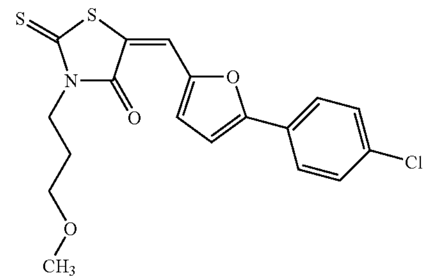 | (5E)-5-{[5-(4-chlorophenyl)-2-furyl]methylene}-3-(3-methoxypropyl-2-thioxo-1,3-thiazolidin-4-one |
| 170 | 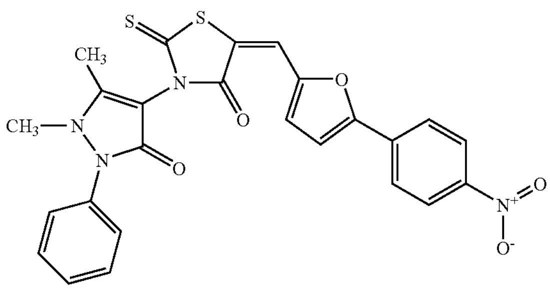 | (5E)-3-(1,5-dimethyl-3-oxo-2-phenyl-2,3-dihydro-1H-pyrazol-4-yl)-5-{[5-(4-nitrophenyl)-2-furyl]methylene}-2-thioxo-1,3-thiazolidin-4-one |
| 171 | 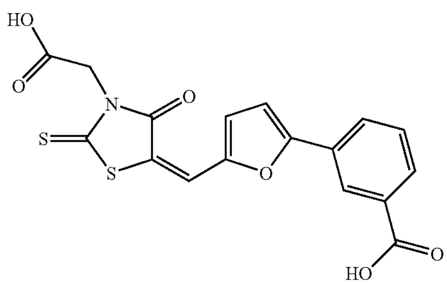 | 3-(5-{(E)-[3-(carboxymethyl)-4-oxo-2-thioxo-1,3-thiazolidin-5-ylidene]methyl}-2-furyl)benzoic acid |
| 172 | 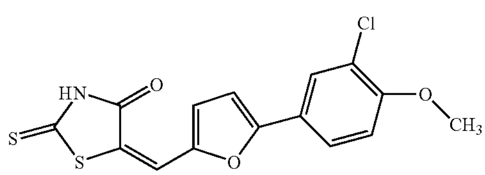 | (5E)-5-{[5-(3-chloro-4-methoxyphenyl)-2-furyl]methylene}-2-thioxo-1,3-thiazolidin-4-one |
| 173 | 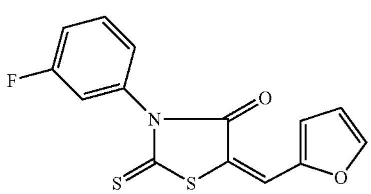 | (5E)-3-(3-fluorophenyl)-5-(2-furylmethylene)-2-thioxo-1,3-thiazolidin-4-one |
| 174 | 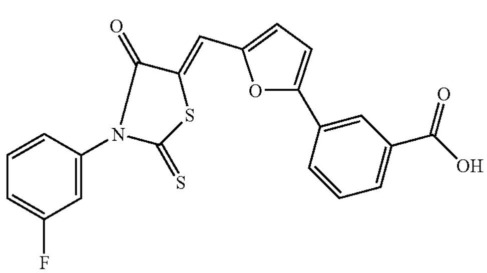 | 3-(5-{(Z)-[3-(3-fluorophenyl)-4-oxo-2-thioxo-1,3-thiazolidin-5-ylidene]methyl}-2-furyl)benzoic acid |

TABLE 1-continued

| Cpd | Structure | Name |
|---|---|---|
| 175 | 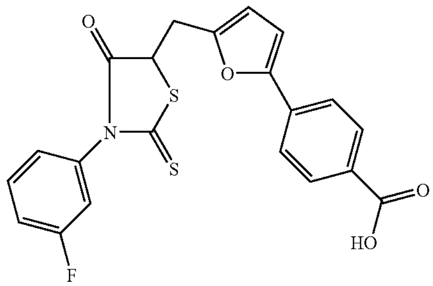 | 4-(5-{(Z)-[3-(3-fluorophenyl)-4-oxo-2-thioxo-1,3-thiazolidin-5-ylidene]methyl}-2-furyl)benzoic acid |
| 176 | 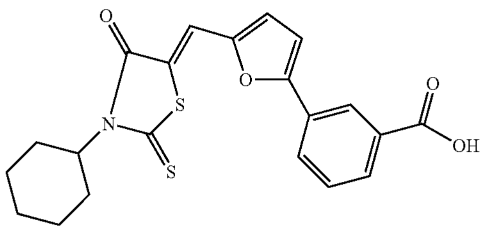 | 3-{5-[(Z)-(3-cyclohexyl-4-oxo-2-thioxo-1,3-thiazolidin-5-ylidene)methyl]-2-furyl}benzoic acid |
| 177 | 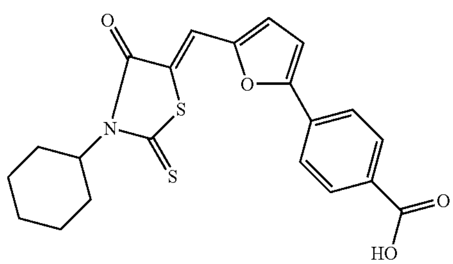 | 4-{5-[(Z)-(3-cyclohexyl-4-oxo-2-thioxo-1,3-thiazolidin-5-ylidene)methyl]-2-furyl}benzoic acid |
| 178 | 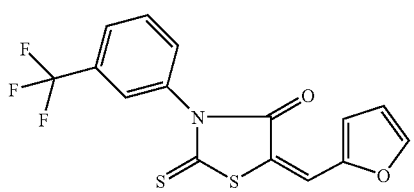 | (5E)-5-(2-furylmethylene)-2-thioxo-3-[3-(trifluoromethyl)phenyl]-1,3-thiazolidin-4-one |
| 179 | 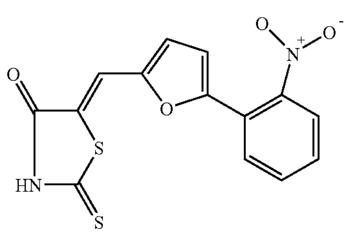 | (5Z)-5-{[5-(2-nitrophenyl)-2-furyl]methylene}-2-thioxo-1,3-thiazolidin-4-one |
| 180 | 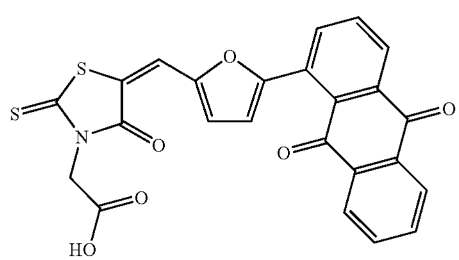 | ((5E)-5-{[5-(9,10-dioxo-9,10-dihydroanthracen-1-yl)-2-furyl]methylene}-4-oxo-2-thioxo-1,3-thiazolidin-3-yl)acetic acid |

TABLE 1-continued

| Cpd | Structure | Name |
|---|---|---|
| 181 | 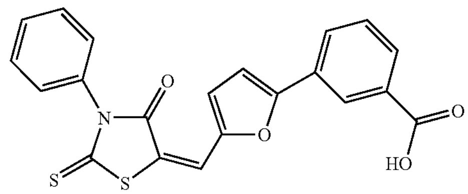 | 3-{5-[(E)-(4-oxo-3-phenyl-2-thioxo-1,3-thiazolidin-5-ylidene)methyl]-2-furyl}benzoic acid |
| 182 | 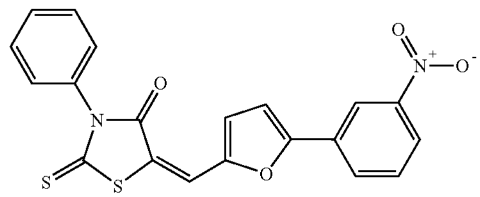 | (5E)-5-{[5-(3-nitrophenyl)-2-furyl]methylene}-3-phenyl-2-thioxo-1,3-thiazolidin-4-one |
| 183 | 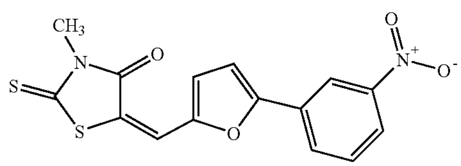 | (5E)-3-methyl-5-{[5-(3-nitrophenyl)-2-furyl]methylene}-2-thioxo-1,3-thiazolidin-4-one |
| 184 | 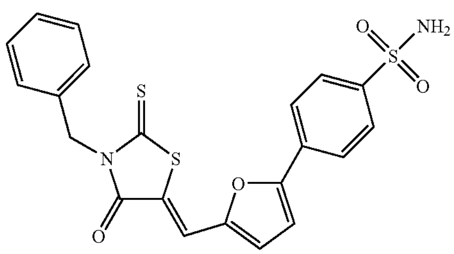 | 4-{5-[(Z)-(3-benzyl-4-oxo-2-thioxo-1,3-thiazolidin-5-ylidene)methyl]-2-furyl}benzenesulfonamide |
| 185 | 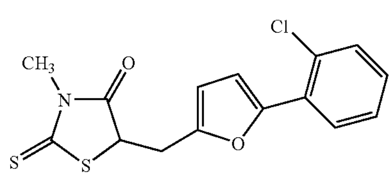 | (5E)-5-{[5-(2-chlorophenyl)-2-furyl]methylene}-3-methyl-2-thioxo-1,3-thiazolidin-4-one |
| 186 | 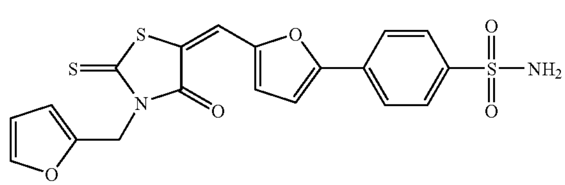 | 4-(5-{(E)-[3-(2-furylmethyl)-4-oxo-2-thioxo-1,3-thiazolidin-5-ylidene]methyl}-2-furyl)benzenesulfonamide |
| 187 | 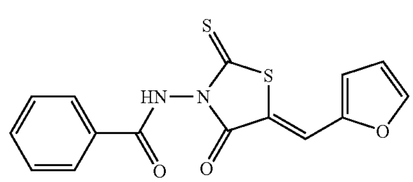 | N-[(5Z)-5-(2-furylmethelene)-4-oxo-2-thioxo-1,3-thiazolidin-3-yl]benzamide |
| 188 | 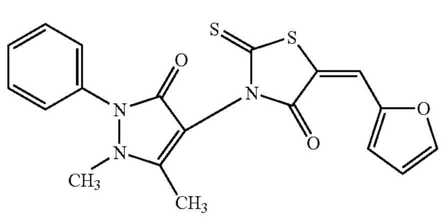 | (5E)-3-(1,5-dimethyl-3-oxo-2-phenyl-2,3-dihydro-1H-pyrazol-4-yl)-5-(2-furylmethylene)-2-thioxo-1,3-thiazolidin-4-one |

TABLE 1-continued

| Cpd | Structure | Name |
| --- | --- | --- |
| 189 | 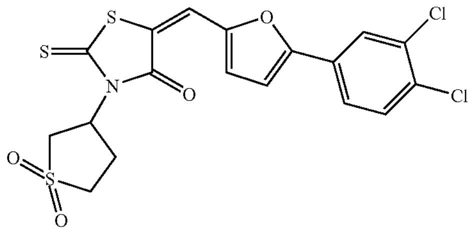 | (5E)-5-{[5-(3,4-dichlorophenyl)-2-furyl]methylene}-3-(1,1-dioxidotetrahydro-3-thienyl)-2-thioxo-1,3-thiazolidin-4-one |
| 190 | 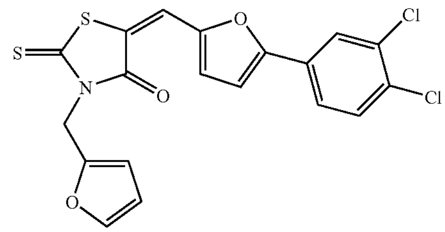 | (5E)-5-{[5-(3,4-dichlorophenyl)-2-furyl]methylene}-3-(2-furylmethyl)-2-thioxo-1,3-thiazolidin-4-one |
| 191 | 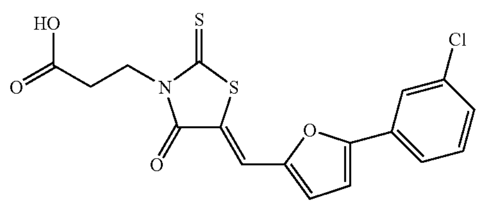 | 3-((5Z)-5-{[5-(3-chlorophenyl)-2-furyl]methylene}-4-oxo-2-thioxo-1,3-thiazolidin-3-yl)propanoic acid |
| 192 | 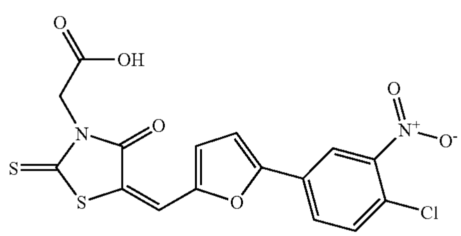 | ((5E)-5-{[5-(4-chloro-3-nitrophenyl)-2-furyl]methylene}-4-oxo-2-thioxo-1,3-thiazolidin-3-yl)acetic acid |
| 193 | 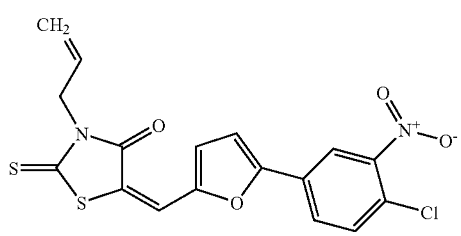 | (5E)-3-allyl-5-{[5-(4-chloro-3-nitrophenyl)-2-furyl]methylene}-2-thioxo-1,3-thiazolidin-4-one |
| 194 | 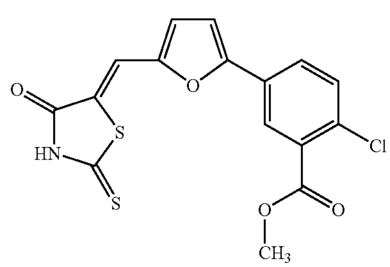 | methyl 2-chloro-5-{5-[(Z)-(4-oxo-2-thioxo-1,3-thiazolidin-5-ylidene)methyl]-2-furyl}benzoate |

TABLE 1-continued

| Cpd | Structure | Name |
|---|---|---|
| 195 | 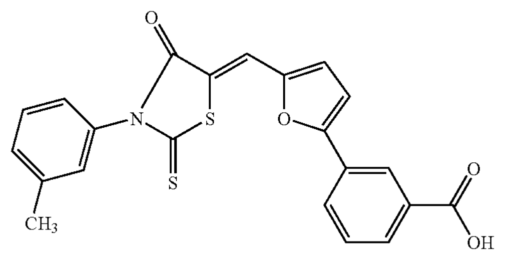 | 3-(5-{(Z)-[3-(3-methylphenyl)-4-oxo-2-thioxo-1,3-thiazolidin-5-ylidene]methyl}-2-furyl)benzoic acid |
| 196 | 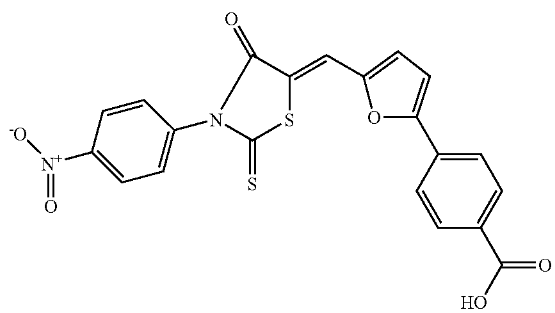 | 4-(5-{(Z)-[3-(4-nitrophenyl)-4-oxo-2-thioxo-1,3-thiazolidin-5-ylidene]methyl}-2-furyl)benzoic acid |
| 197 | 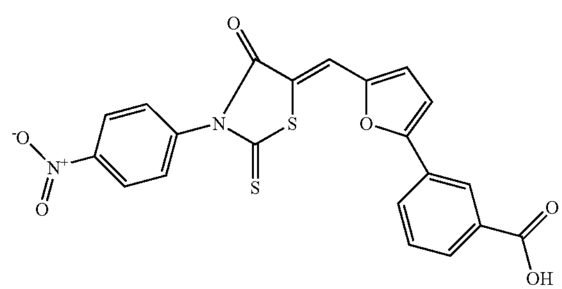 | 3-(5-{(Z)-[3-(4-nitrophenyl)-4-oxo-2-thioxo-1,3-thiazolidin-5-ylidene]methyl}-2-furyl)benzoic acid |
| 198 | 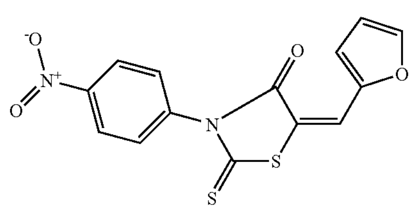 | (5E)-5-(2-furylmethylene)-3-(4-nitrophenyl)-2-thioxo-1,3-thiazolidin-4-one |
| 199 | 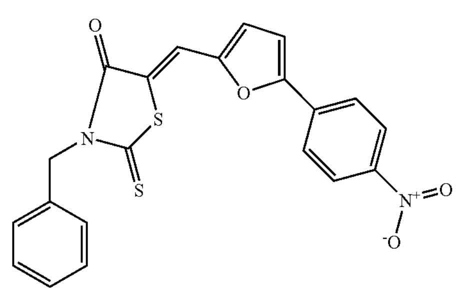 | (5Z)-3-benzyl-5-{[5-(4-nitrophenyl)-2-furyl]methylene}-2-thioxo-1,3-thiazolidin-4-one |

TABLE 1-continued

| Cpd | Structure | Name |
|---|---|---|
| 200 | 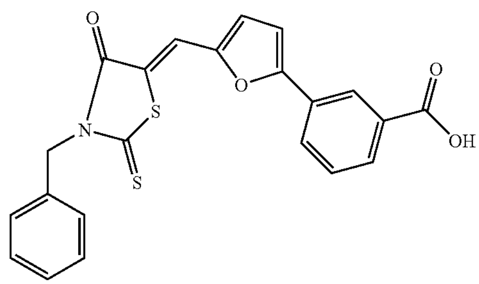 | 3-{5-[(Z)-(3-benzyl-4-oxo-2-thioxo-1,3-thiazolidin-5-ylidene)methyl]-2-furyl}benzoic acid |
| 201 | 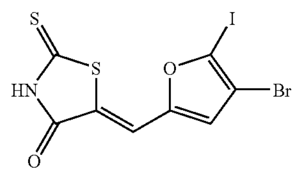 | (5Z)-5-[(4-bromo-5-iodo-2-furyl)methylene]-2-thioxo-1,3-thiazolidin-4-one |
| 202 | 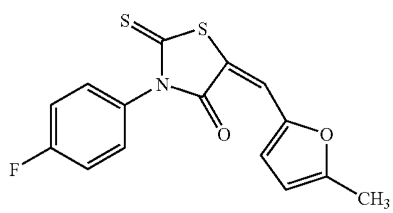 | (5E)-3-(4-fluorophenyl)-5-[(5-methyl-2-furyl)methylene]-2-thioxo-1,3-thiazolidin-4-one |
| 203 | 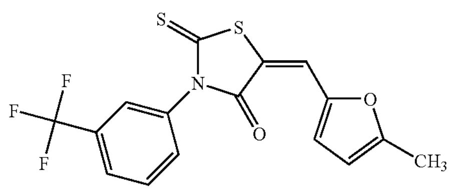 | (5E)-5-[(5-methyl-2-furyl)methylene]-2-thioxo-3-[3-(trifluoromethyl)phenyl]-1,3-thiazolidin-4-one |
| 204 | 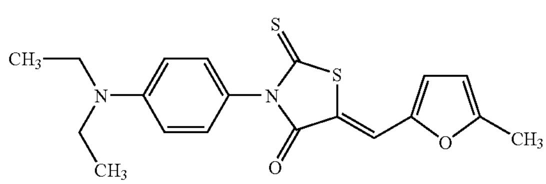 | (5Z)-3-[4-(diethylamino)phenyl]-5-[(5-methyl-2-furyl)methylene]-2-thioxo-1,3-thiazolidin-4-one |
| 205 | 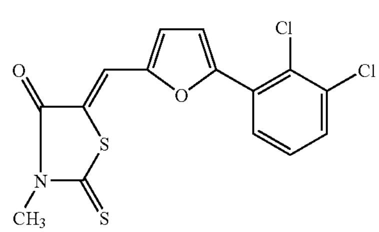 | (5Z)-5-{[5-(2,3-dichlorophenyl)-2-furyl]methylene}-3-methyl-2-thioxo-1,3-thiazolidin-4-one |
| 206 | 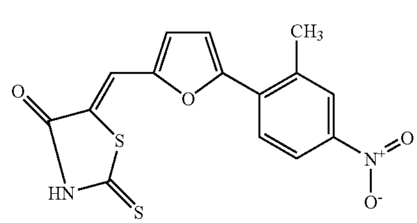 | (5Z)-5-{[5-(2-methyl-4-nitrophenyl)-2-furyl]methylene}-2-thioxo-1,3-thiazolidin-4-one |

TABLE 1-continued

| Cpd | Structure | Name |
|---|---|---|
| 207 | 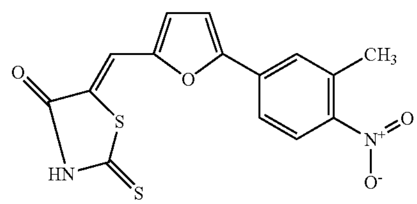 | (5Z)-5-{[5-(3-methyl-4-nitrophenyl)-2-furyl]methylene}-2-thioxo-1,3-thiazolidin-4-one |
| 208 | 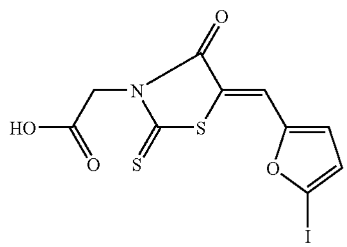 | {(5Z)-5-[(5-iodo-2-furyl)methylene]-4-oxo-2-thioxo-1,3-thiazolidin-3-yl}acetic acid |
| 209 | 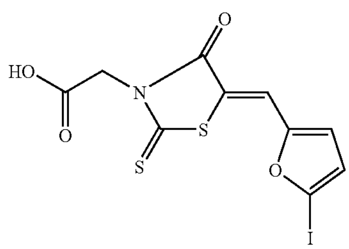 | {(5Z)-5-[(5-bromo-2-furyl)methylene]4-oxo-2-thioxo-1,3-thiazolidin-3-yl}acetic acid |
| 210 | 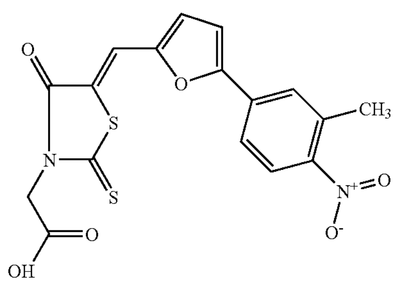 | ((5Z)-5-{[5-(3-methyl-4-nitrophenyl)-2-furyl]methylene}-4-oxo-2-thioxo-1,3-thiazolidin-3-yl)acetic acid |
| 211 | 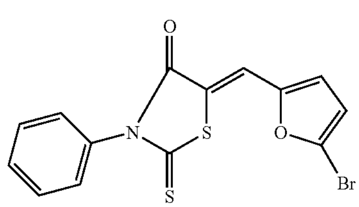 | (5Z)-5-[(5-bromo-2-furyl)methylene]-3-phenyl-2-thioxo-1,3-thiazolidin-4-one |
| 212 | 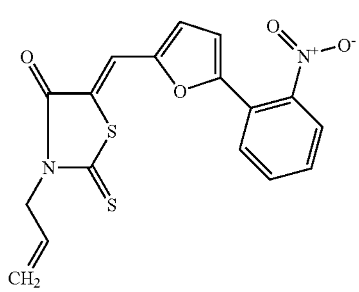 | (5Z)-3-allyl-5-{[5-(2-nitrophenyl)-2-furyl]methylene}-2-thioxo-1,3-thiazolidin-4-one |

TABLE 1-continued

| Cpd | Structure | Name |
|---|---|---|
| 213 | 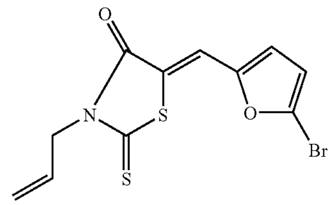 | (5Z)-3-allyl-5-[(5-bromo-2-furyl)methylene]-2-thioxo-1,3-thiazolidin-4-one |
| 214 | 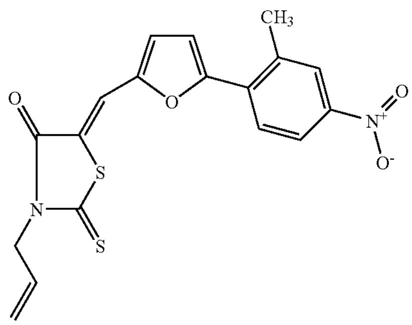 | (5Z)-3-allyl-5-{[5-(2-methyl-4-nitrophenyl)-2-furyl]methylene}-2-thioxo-1,3-thiazolidin-4-one |
| 215 | 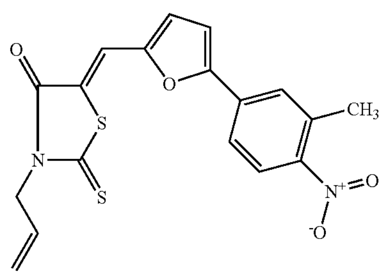 | (5Z)-3-allyl-5-{[5-(3-methyl-4-nitrophenyl)-2-furyl]methylene}-2-thioxo-1,3-thiazolidin-4-one |
| 216 | 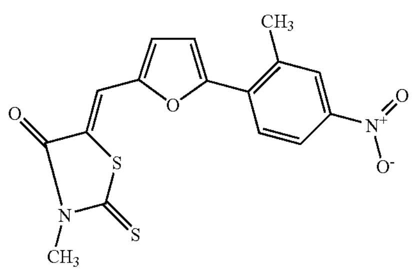 | (5Z)-3-methyl-5-{[5-(2-methyl-4-nitrophenyl)-2-furyl]methylene}-2-thioxo-1,3-thiazolidin-4-one |
| 217 | 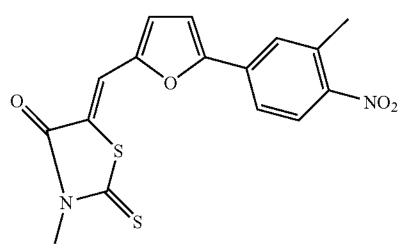 | (5Z)-3-methyl-5-{[5-(3-methyl-4-nitrophenyl)-2-furyl]methylene}-2-thioxo-1,3-thiazolidin-4-one |
| 218 | 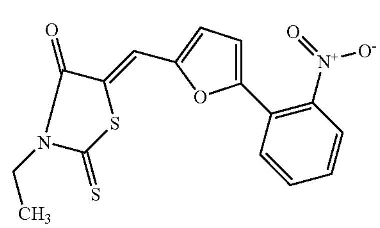 | (5Z)-3-ethyl-5-{[5-(2-nitrophenyl)-2-furyl]methylene}-2-thioxo-1,3-thiazolidin-4-one |

TABLE 1-continued

| Cpd | Structure | Name |
|---|---|---|
| 219 | 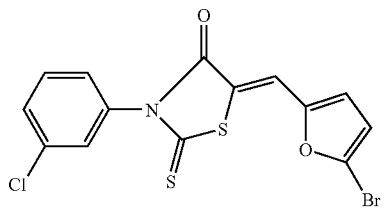 | (5Z)-5-[(5-bromo-2-furyl)methylene]-3-(3-chlorophenyl)-2-thioxo-1,3-thiazolidin-4-one |
| 220 | 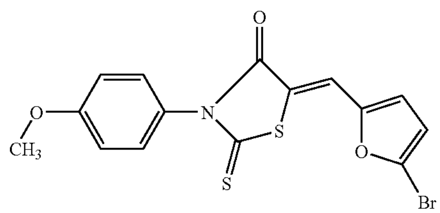 | (5Z)-5-[(5-bromo-2-furyl)methylene]-3-(4-methoxyphenyl)-2-thioxo-1,3-thiazolidin-4-one |
| 221 | 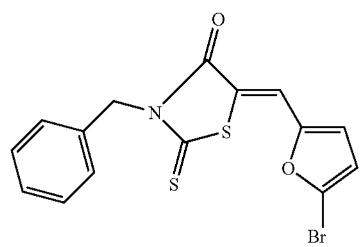 | (5Z)-3-benzyl-5-[(5-bromo-2-furyl)methylene]-2-thioxo-1,3-thiazolidin-4-one |
| 222 | 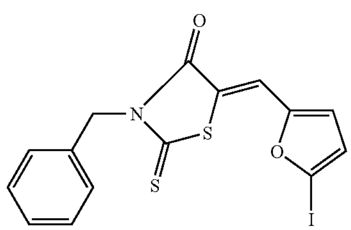 | (5Z)-3-benzyl-5-[(5-iodo-2-furyl)methylene]-2-thioxo-1,3-thiazolidin-4-one |
| 223 | 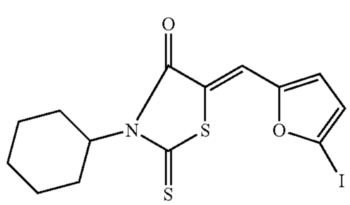 | (5Z)-3-cyclohexyl-5-[(5-iodo-2-furyl)methylene]-2-thioxo-1,3-thiazolidin-4-one |
| 224 | 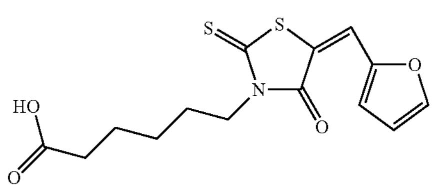 | 6-[(5E)-5-(2-furylmethylene)-4-oxo-2-thioxo-1,3-thiazolidin-3-yl]hexanoic acid |
| 225 | 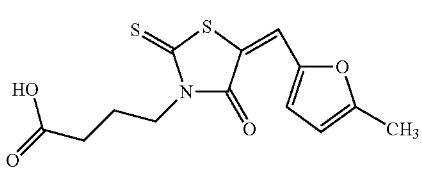 | 4-[(5E)-5-[(5-methyl-2-furyl)methylene]-4-oxo-2-thioxo-1,3-thiazolidin-3-yl}butanoic acid |

TABLE 1-continued

| Cpd | Structure | Name |
|---|---|---|
| 226 | 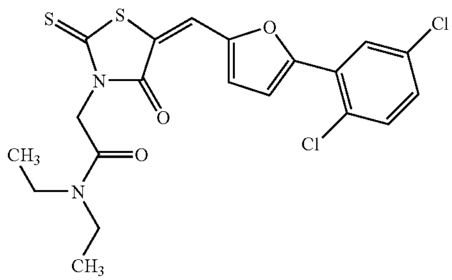 | 2-((5E)-5-{[5-(2,5-dichlorophenyl)-2-furyl]methylene}-4-oxo-2-thioxo-1,3-thiazolidin-3-yl)-N,N-diethylacetamide |
| 227 | 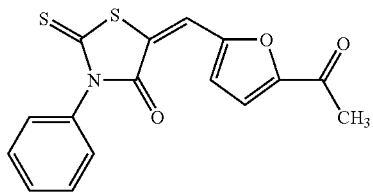 | (5E)-5-[(5-acetyl-2-furyl)methylene]-3-phenyl-2-thioxo-1,3-thiazolidin-4-one |
| 228 | 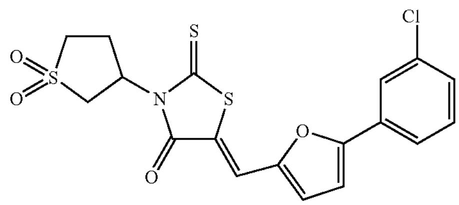 | (5Z)-5-{[5-(3-chlorophenyl)-2-furyl]methylene}-3-(1,1-dioxidotetrahydro-3-thienyl)-2-thioxo-1,3-thiazolidin-4-one |
| 229 | 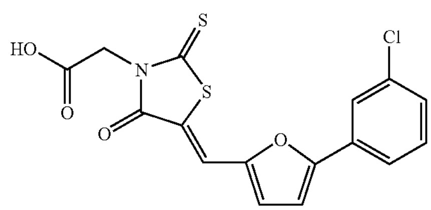 | ((5Z)-5-{[5-(3-chlorophenyl)-2-furyl]methylene}-4-oxo-2-thioxo-1,3-thiazolidin-3-yl)acetic acid |
| 230 | 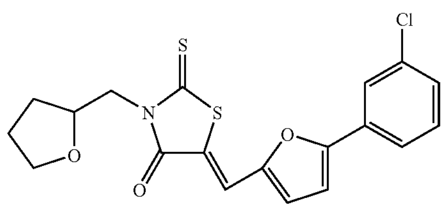 | (5Z)-5-{[5-(3-chlorophenyl)-2-furyl]methylene}-3-(tetrahydrofuran-2-ylmethyl)-2-thioxo-1,3-thiazolidin-4-one |
| 231 | 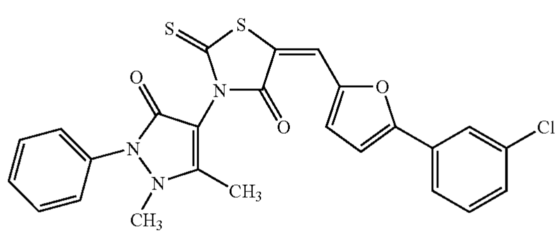 | (5E)-5-{[5-(3-chlorophenyl)-2-furyl]methylene}-3-(1,5-dimethyl-3-oxo-2-phenyl-2,3-dihydro-1H-pyrazol-4-yl)-2-thioxo-1,3-thiazolidin-4-one |

TABLE 1-continued

| Cpd | Structure | Name |
|---|---|---|
| 232 | 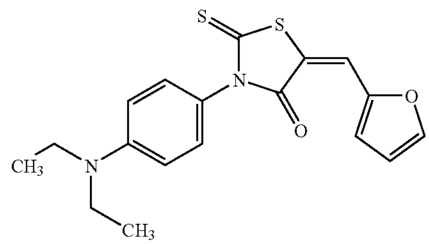 | (5E)-3-[4-(diethylamino)phenyl]-5-(2-furylmethylene)-2-thioxo-1,3-thiazolidin-4-one |
| 233 | 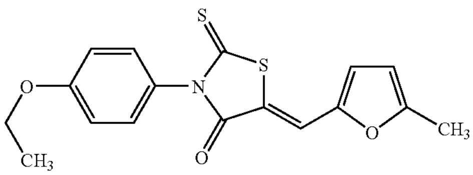 | (5Z)-3-(4-ethoxyphenyl)-5-[(5-methyl-2-furyl)methylene]-2-thioxo-1,3-thiazolidin-4-one |
| 234 | 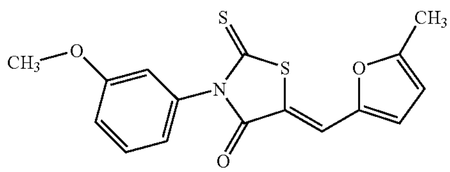 | (5Z)-3-(3-methoxyphenyl)-5-[(5-methyl-2-furyl)methylene]-2-thioxo-1,3-thiazolidin-4-one |
| 235 | 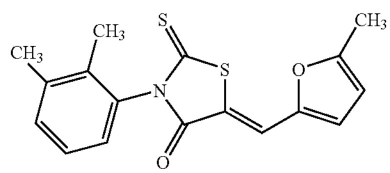 | (5Z)-3-(2,3-dimethylphenyl)-5-[(5-methyl-2-furyl)methylene]-2-thioxo-1,3-thiazolidin-4-one |
| 236 | 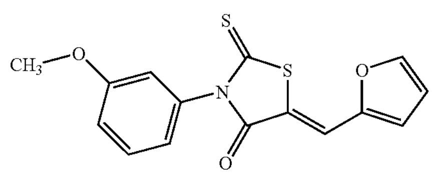 | (5Z)-5-(2-furylmethylene)-3-(3-methoxyphenyl)-2-thioxo-1,3-thiazolidin-4-one |
| 237 | 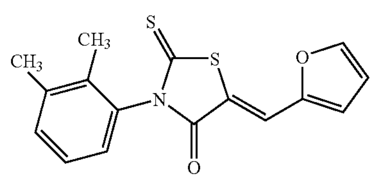 | (5Z)-3-(2,3-dimethylphenyl)-5-(2-furylmethylene)-2-thioxo-1,3-thiazolidin-4-one |
| 238 | 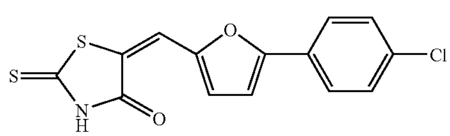 | (5E)-5-{[5-(4-chlorophenyl)-2-furyl]methylene}-2-thioxo-1,3-thiazolidin-4-one |
| 239 | 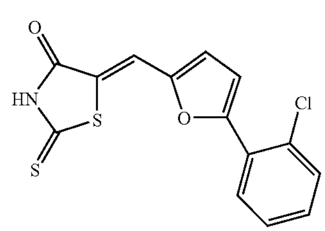 | (5Z)-5-{[5-(2-chlorophenyl)-2-furyl]methylene}-2-thioxo-1,3-thiazolidin-4-one |

TABLE 1-continued

| Cpd | Structure | Name |
|---|---|---|
| 240 | 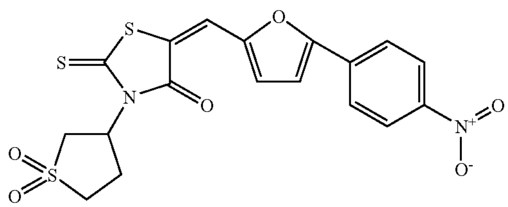 | (5E)-3-(1,1-dioxidotetrahydro-3-thienyl)-5-{[5-(4-nitrophenyl)-2-furyl]methylene}-2-thioxo-1,3-thiazolidin-4-one |
| 241 | 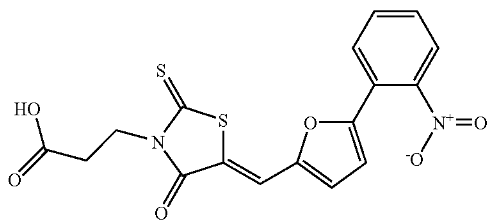 | 3-((5Z)-5-{[5-(2-nitrophenyl)-2-furyl]methylene}-4-oxo-2-thioxo-1,3-thiazolidin-3-yl)propanoic acid |
| 242 | 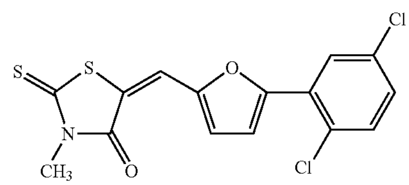 | (5E)-5-{[5-(2,5-dichlorophenyl)-2-furyl]methylene}-3-methyl-2-thioxo-1,3-thiazolidin-4-one |
| 243 | 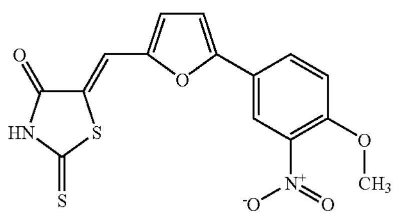 | (5Z)-5-{[5-(4-methoxy-3-nitrophenyl)-2-furyl]methylene}-2-thioxo-1,3-thiazolidin-4-one |
| 244 | 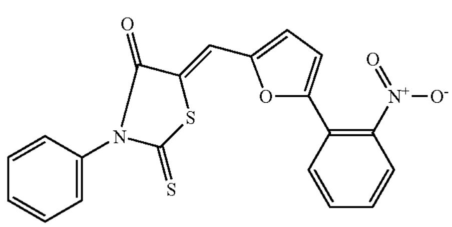 | (5Z)-5-{[5-(2-nitrophenyl)-2-furyl]methylene}-3-phenyl-2-thioxo-1,3-thiazolidin-4-one |
| 245 | 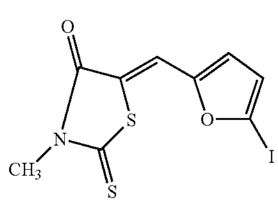 | (5Z)-5-[(5-iodo-2-furyl)methylene]-3-methyl-2-thioxo-1,3-thiazolidin-4-one |
| 246 | 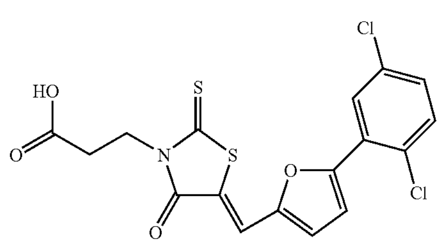 | 3-((5Z)-5-{[5-(2, 5-dichlorophenyl)-2-furyl]methylene}-4-oxo-2-thioxo-1,3-thiazolidin-3-yl)propanoic acid |

TABLE 1-continued

| Cpd | Structure | Name |
| --- | --- | --- |
| 247 | 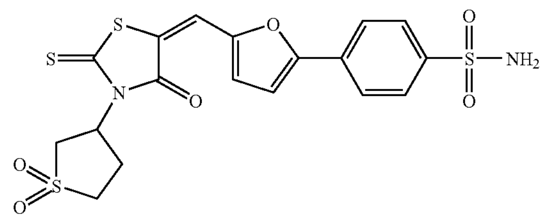 | 4-(5-{(E)-[3-(1,1-dioxidotetrahydro-3-thienyl)-4-oxo-2-thioxo-1,3-thiazolidin-5-ylidene]methyl}-2-furyl)benzenesulfonamide |
| 248 | 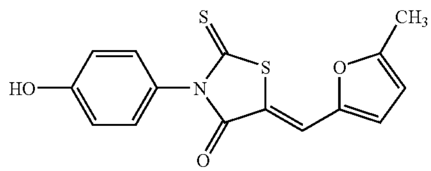 | (5Z)-3-(4-hydroxyphenyl)-5-[(5-methyl-2-furyl)methylene]-2-thioxo-1,3-thiazolidin-4-one |
| 249 | 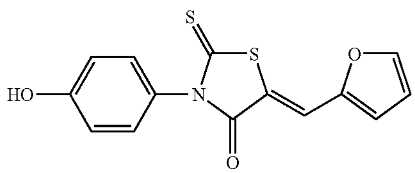 | (5Z)-5-(2-furylmethylene)-3-(4-hydroxyphenyl)-2-thioxo-1,3-thiazolidin-4-one |
| 250 | 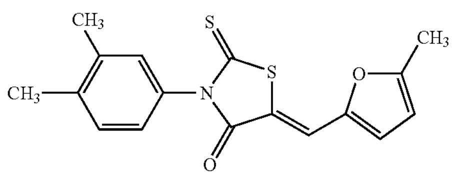 | (5Z)-3-(3,4-dimethylphenyl)-5-[(5-methyl-2-furyl)methylene]-2-thioxo-1,3-thiazolidin-4-one |
| 251 | 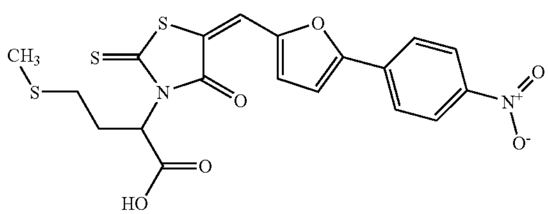 | 4-(methylthio)-2-((5E)-5-{[5-(4-nitrophenyl)-2-furyl]methylene}-4-oxo-2-thioxo-1,3-thiazolidin-3-yl)butanoic acid |
| 252 | 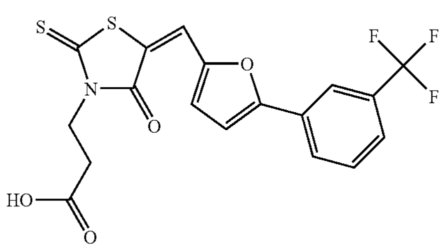 | 3-[(5E)-4-oxo-2-thioxo-5-({5-[3-(trifluoromethyl)phenyl]-2-furyl}methylene)-1,3-thiazolidin-3-yl]propanoic acid |
| 253 | 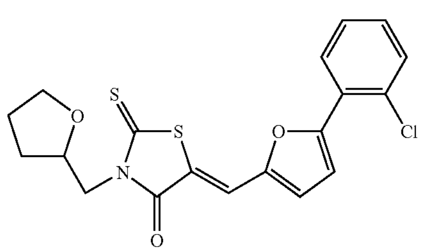 | (5Z)-5-{[5-(2-chlorophenyl)-2-furyl]methylene}-3-(tetrahydrofuran-2-ylmethyl)-2-thioxo-1,3-thiazolidin-4-one |

TABLE 1-continued

| Cpd | Structure | Name |
|---|---|---|
| 254 | 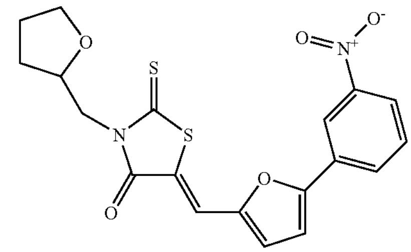 | (5Z)-5-{[5-(3-nitrophenyl)-2-furyl]methylene}-3-(tetrahydrofuran-2-ylmethyl)-2-thioxo-1,3-thiazolidin-4-one |
| 255 | 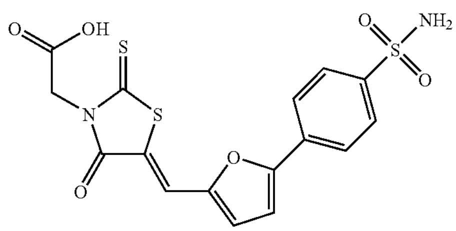 | [(5Z)-5-({5-[4-(aminosulfonyl)phenyl]-2-furyl}methylene)-4-oxo-2-thioxo-1,3-thiazolidin-3-yl]acetic acid |
| 256 | 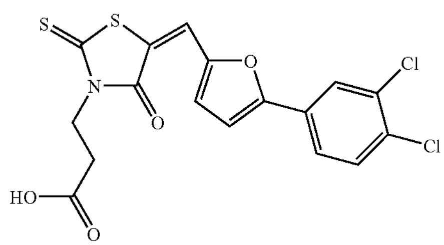 | 3-((5E)-5-{[5-(3,4-dichlorophenyl)-2-furyl]methylene}-4-oxo-2-thioxo-1,3-thiazolidin-3-yl)propanoic acid |
| 257 | 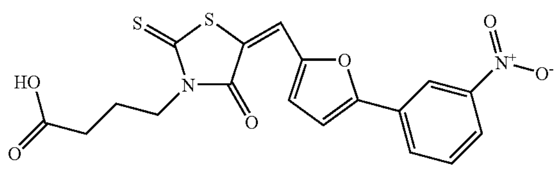 | 4-((5E)-5-{[5-(3-nitrophenyl)-2-furyl]methylene}-4-oxo-2-thioxo-1,3-thiazolidin-3-yl)butanoic acid |
| 258 | 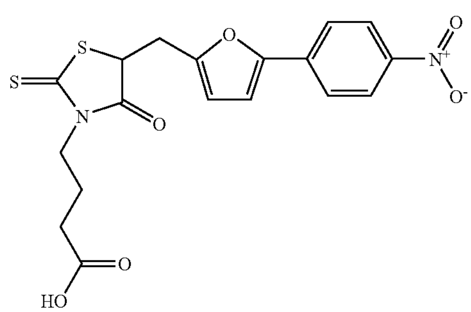 | 4-((5E)-5-{[5-(4-nitrophenyl)-2-furyl]methylene}-4-oxo-2-thioxo-1,3-thiazolidin-3-yl)butanoic acid |
| 259 | 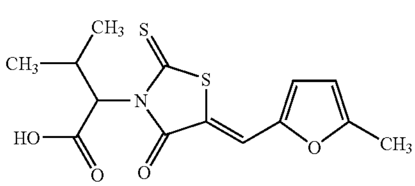 | 3-methyl-2-((5Z)-5-[(5-methyl-2-furyl)methylene]-4-oxo-2-thioxo-1,3-thiazolidin-3-yl}butanoic acid |
| 260 | 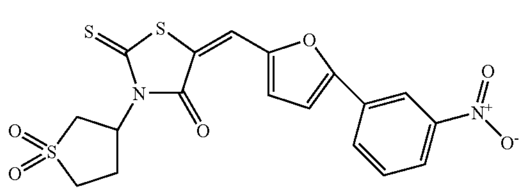 | (5E)-3-(1,1-dioxidotetrahydro-3-thienyl)-5-{[5-(3-nitrophenyl)-2-furyl]methylene}-2-thioxo-1,3-thiazolidin-4-one |

TABLE 1-continued

| Cpd | Structure | Name |
| --- | --- | --- |
| 261 | 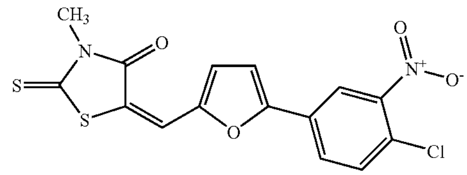 | (5E)-5-{[5-(4-chloro-3-nitrophenyl)-2-furyl]methylene}-3-methyl-2-thioxo-1,3-thiazolidin-4-one |
| 262 | 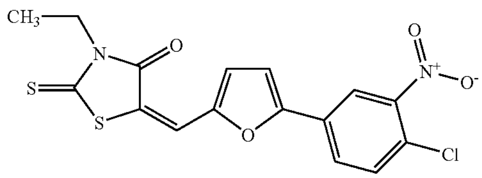 | (5E)-5-{[5-(4-chloro-3-nitrophenyl)-2-furyl]methylene}-3-ethyl-2-thioxo-1,3-thiazolidin-4-one |
| 263 | 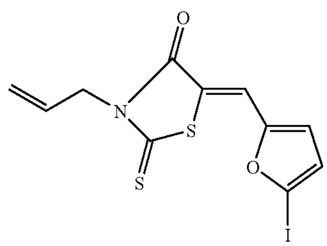 | (5Z)-3-allyl-5-[(5-iodo-2-furyl)methylene]-2-thioxo-1,3-thiazolidin-4-one |
| 264 | 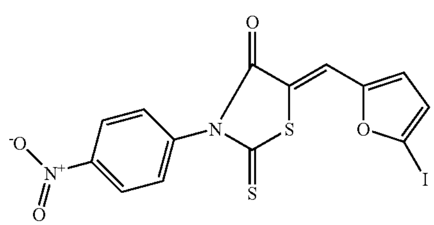 | (5Z)-5-[(5-iodo-2-furyl)methylene]-3-(4-nitrophenyl)-2-thioxo-1,3-thiazolidin-4-one |
| 265 | 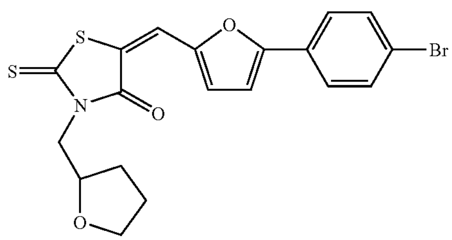 | (5E)-5-{[5-(4-bromophenyl)-2-furyl]methylene}-3-(tetrahydrofuran-2-ylmethyl)-2-thioxo-1,3-thiazolidin-4-one |
| 266 | 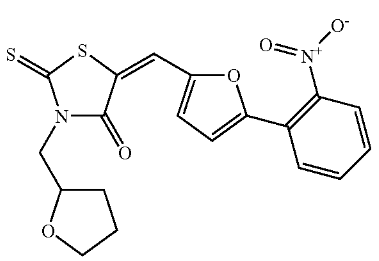 | (5E)-5-{[5-(2-nitrophenyl)-2-furyl]methylene}-3-(tetrahydrofuran-2-ylmethyl)-2-thioxo-1,3-thiazolidin-4-one |

TABLE 1-continued

| Cpd | Structure | Name |
| --- | --- | --- |
| 267 | 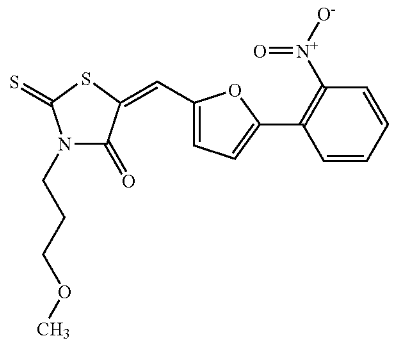 | (5E)-3-(3-methoxypropyl)-5-{[5-(2-nitrophenyl)-2-furyl]methylene}-2-thioxo-1,3-thiazolidin-4-one |
| 268 | 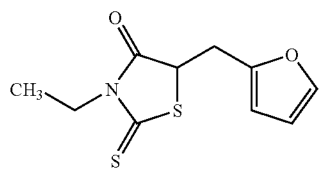 | (5Z)-3-ethyl-5-(2-furylmethylene)-2-thioxo-1,3-thiazolidin-4-one |
| 269 | 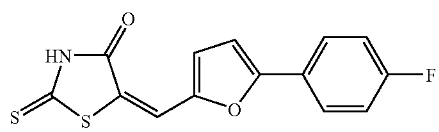 | (5E)-5-{[5-(4-fluorophenyl)-2-furyl]methylene}-2-thioxo-1,3-thiazolidin-4-one |
| 270 | 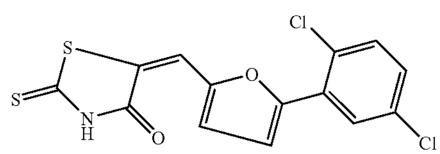 | (5E)-5-{[5-(2,5-dichlorophenyl)-2-furyl]methylene}-2-thioxo-1,3-thiazolidin-4-one |
| 271 | 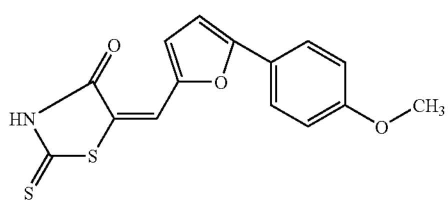 | (5E)-5-{[5-(4-methoxyphenyl)-2-furyl]methylene}-2-thioxo-1,3-thiazolidin-4-one |
| 272 | 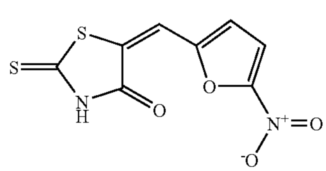 | (5E)-5-[(5-nitro-2-furyl)methylene]-2-thioxo-1,3-thiazolidin-4-one |
| 273 | 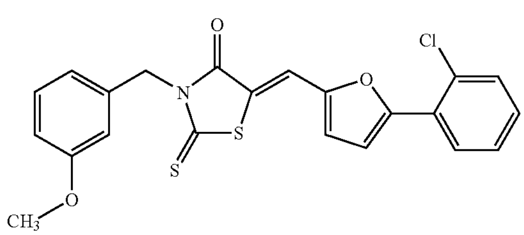 | (5Z)-5-{[5-(2-chlorophenyl)-2-furyl]methylene}-3-(3-methoxybenzyl)-2-thioxo-1,3-thiazolidin-4-one |

TABLE 1-continued

| Cpd | Structure | Name |
|---|---|---|
| 274 | 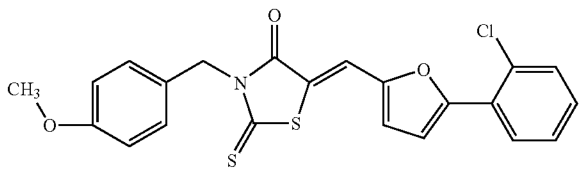 | (5Z)-5-{[5-(2-chlorophenyl)-2-furyl]methylene}-3-(4-methoxybenzyl-2-thioxo-1,3-thiazolidin-4-one |
| 275 | 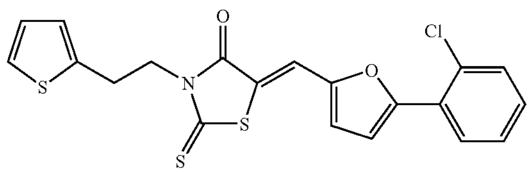 | (5Z)-5-{[5-(2-chlorophenyl)-2-furyl]methylene}-3-[2-(2-thienyl)ethyl]-2-thioxo-1,3-thiazolidin-4-one |
| 276 | 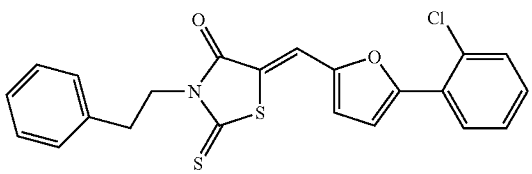 | (5Z)-5-{[5-(2-chlorophenyl)-2-furyl]methylene}-3-(2-phenylethyl)-2-thioxo-1,3-thiazolidin-4-one |
| 277 | 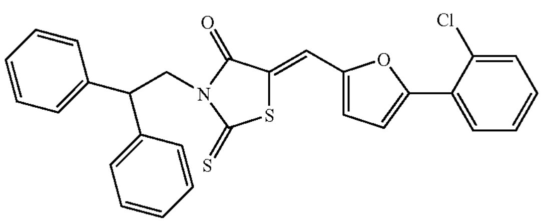 | (5Z)-5-{[5-(2-chlorophenyl)-2-furyl]methylene}-3-(2,2-diphenylethyl)-2-thioxo-1,3-thiazolidin-4-one |
| 278 | 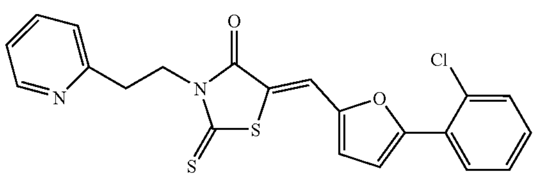 | (5Z)-5-{[5-(2-chlorophenyl)-2-furyl]methylene}-3-(2-pyridin-2-ylethyl)-2-thioxo-1,3-thiazolidin-4-one |
| 279 | 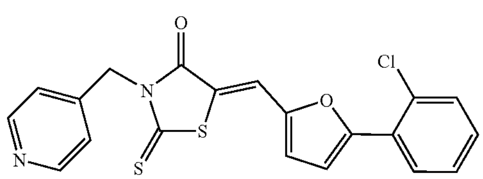 | (5Z)-5-{[5-(2-chlorophenyl)-2-furyl]methylene}-3-(pyridin-4-ylmethyl)-2-thioxo-1,3-thiazolidin-4-one |
| 280 | 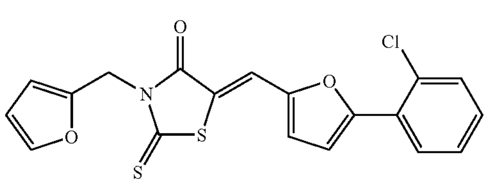 | (5Z)-5-{[5-(2-chlorophenyl)-2-furyl]methylene}-3-(2-furylmethyl)-2-thioxo-1,3-thiazolidin-4-one |
| 281 | 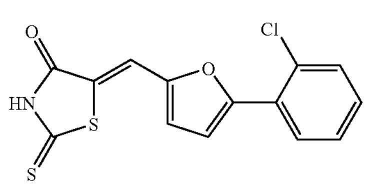 | (5Z)-5-{[5-(2-chlorophenyl)-2-furyl]methylene}-2-thioxo-1,3-thiazolidin-4-one |

TABLE 1-continued

| Cpd | Structure | Name |
|---|---|---|
| 282 | 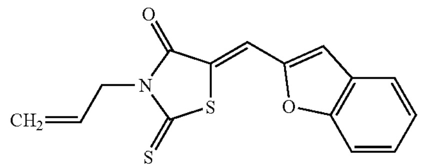 | (5Z)-5-(1-benzofuran-2-ylmethylene)-3-propyl-2-thioxo-1,3-thiazolidin-4-one |
| 283 | 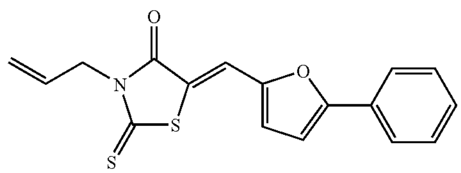 | (5Z)-3-allyl-5-[(5-phenyl-2-furyl)methylene]-2-thioxo-1,3-thiazolidin-4-one |
| 284 | 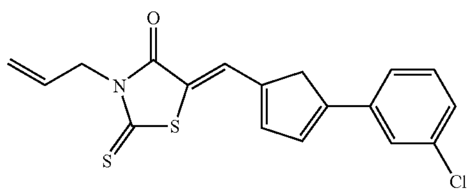 | (5Z)-3-allyl-5-{[5-(3-chlorophenyl)-2-furyl]methylene}-2-thioxo-1,3-thiazolidin-4-one |
| 285 | 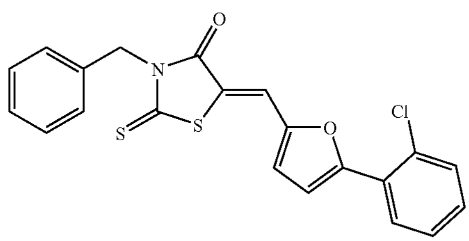 | (5Z)-3-benzyl-5-{[5-(2-chlorophenyl)-2-furyl]methylene}-2-thioxo-1,3-thiazolidin-4-one |
| 286 | 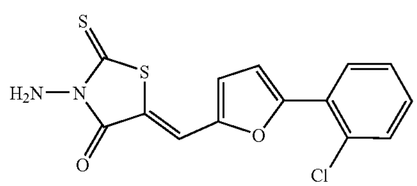 | (5Z)-3-amino-5-{[5-(2-chlorophenyl)-2-furyl]methylene}-2-thioxo-1,3-thiazolidin-4-one |
| 287 | 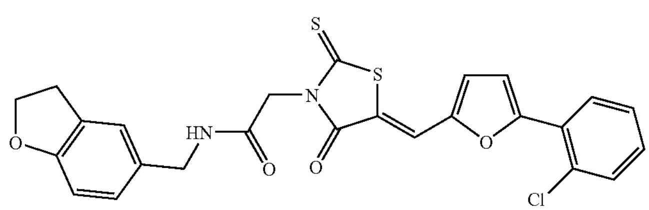 | N-(1,3-benzodioxol-5-ylmethyl)-2-((5Z)-5-{[5-(2-chlorophenyl)-2-furyl]methylene}-4-oxo-2-thioxo-1,3-thiazolidin-3-yl)acetamide |
| 288 | 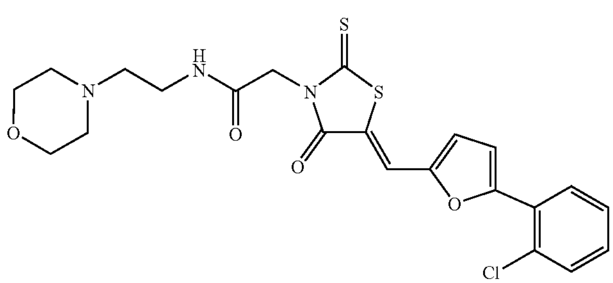 | 2-((5Z)-5-{[5-(2-chlorophenyl)-2-furyl]methylene}-4-oxo-2-thioxo-1,3-thiazolidin-3-yl)-N-(2-morpholin-4-ylethyl)acetamide |

TABLE 1-continued

| Cpd | Structure | Name |
|---|---|---|
| 289 | 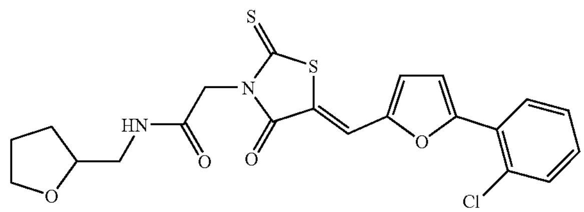 | 2-((5Z)-5-{[5-(2-chlorophenyl)-2-furyl]methylene}-4-oxo-2-thioxo-1,3-thiazolidin-3-yl)-N-(tetrahydrofuran-2-ylmethyl)acetamide |
| 290 | 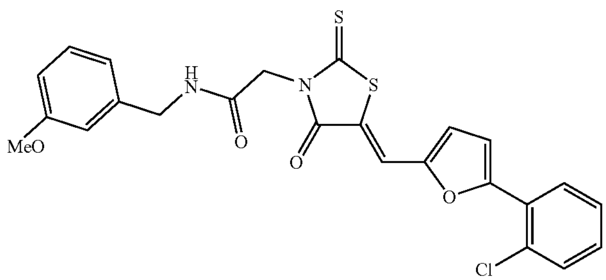 | 2-((5Z)-5-{[5-(2-chlorophenyl)-2-furyl]methylene}-4-oxo-2-thioxo-1,3-thiazolidin-3-yi)-N-(3-methoxybenzyl)acetamide |
| 291 | 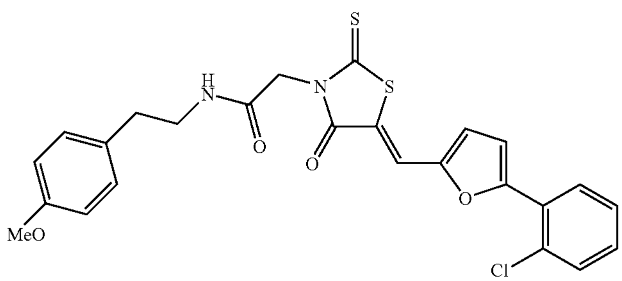 | 2-((5Z)-5-{[5-(2-chlorophenyl)-2-furyl]methylene}-4-oxo-2-thioxo-1,3-thiazolidin-3-yl)-N-[2-(4-methoxyphenyl)ethyl]acetamide |
| 292 | 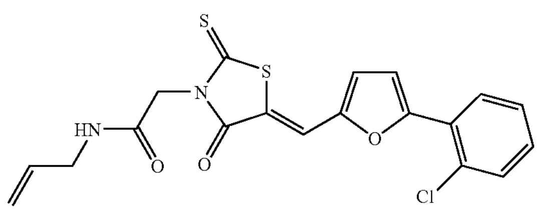 | N-allyl-2-((5Z)-5-{[5-(2-chlorophenyl)-2-furyl]methylene}-4-oxo-2-thioxo-1,3-thiazolidin-3-yl)acetamide |
| 293 | 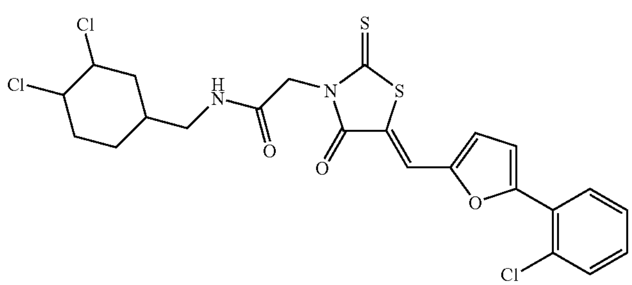 | 2-((5Z)-5-{[5-(2-chlorophenyl)-2-furyl]methylene}-4-oxo-2-thioxo-1,3-thiazolidin-3-yl)-N-(3,4-dichlorobenzyl)acetamide |
| 294 | 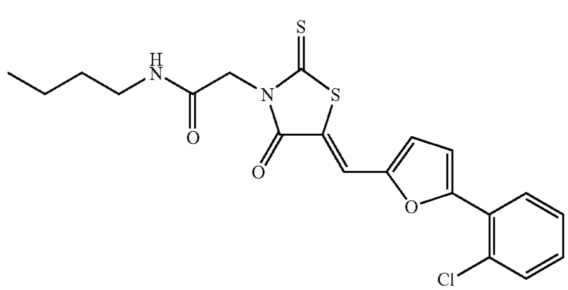 | N-butyl-2-((5Z)-5-{[5-(2-chlorophenyl)-2-furyl]methylene}-4-oxo-2-thioxo-1,3-thiazolidin-3-yl)acetamide |

TABLE 1-continued

| Cpd | Structure | Name |
|---|---|---|
| 295 | 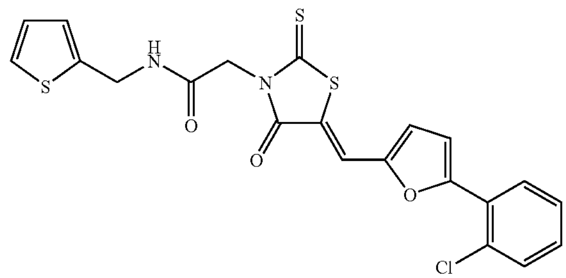 | 2-((5Z)-5-{[5-(2-chlorophenyl)-2-furyl]methylene}-4-oxo-2-thioxo-1,3-thiazolidin-3-yl)-N-(2-thienylmethyl)acetamide |
| 296 | 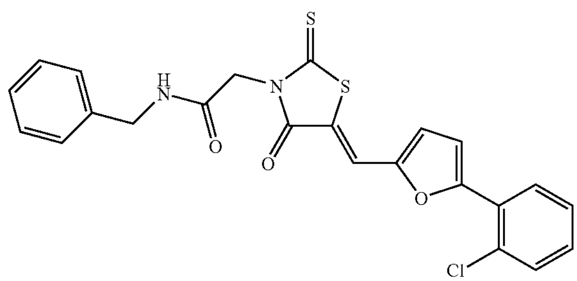 | N-benzyl-2-((5Z)-5-{[5-(2-chlorophenyl)-2-furyl]methylene}-4-oxo-2-thioxo-1,3-thiazolidin-3-yl)acetamide |
| 297 | 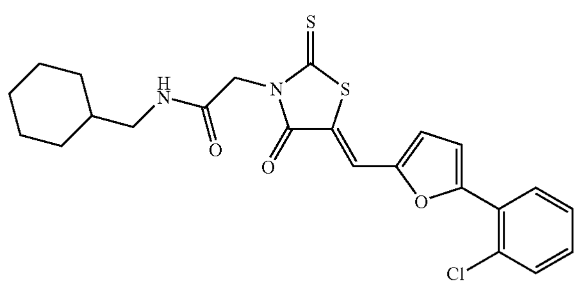 | 2-((5Z)-5-{[5-(2-chlorophenyl)-2-furyl]methylene}-4-oxo-2-thioxo-1,3-thiazolidin-3-yl)-N-(cyclohexylmethyl)acetamide |
| 298 | 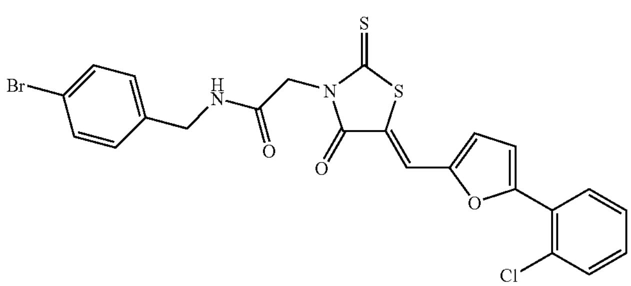 | N-(4-bromobenzyl)-2-((5Z)-5-{[5-(2-chlorophenyl)-2-furyl]methylene}-4-oxo-2-thioxo-1,3-thiazolidin-3-yl)acetamide |
| 299 | 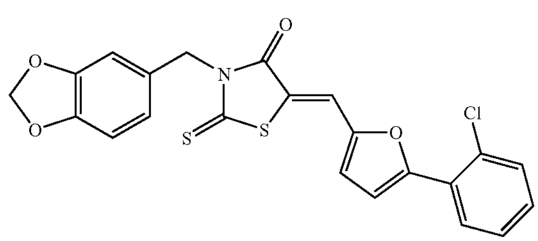 | (5Z)-3-(1,3-benzodioxol-5-ylmethyl)-5-{[5-(2-chlorophenyl)-2-furyl]methylene}-2-thioxo-1,3-thiazolidin-4-one |

TABLE 1-continued

| Cpd | Structure | Name |
| --- | --- | --- |
| 300 | 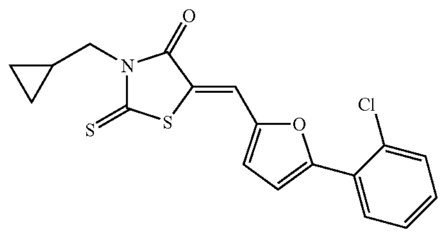 | (5Z)-5-{[5-(2-chlorophenyl)-2-furyl)methylene}-3-(cyclopropylmethyl)-2-thioxo-1,3-thiazolidin-4-one |
| 301 | 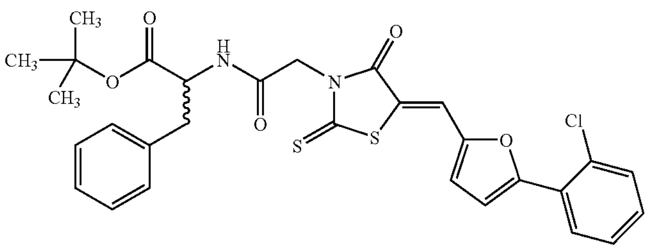 | tert-butyl N-[((5Z)-5-{[5-(2-chlorophenyl)-2-furyl]methylene}-4-oxo-2-thioxo-1,3-thiazolidin-3-yl)acetyl]phenylalaninate |
| 302 | 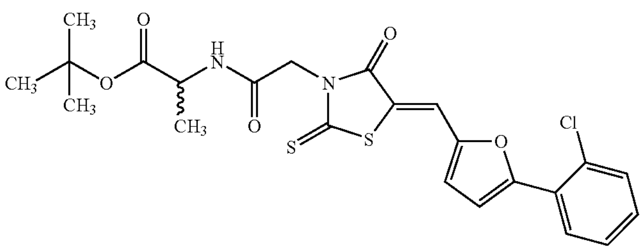 | tert-butyl N-[((5Z)-5-{[5-(2-chlorophenyl)-2-furyl]methylene}-4-oxo-2-thioxo-1,3-thiazolidin-3-yl)acetyl]alaninate |
| 303 | 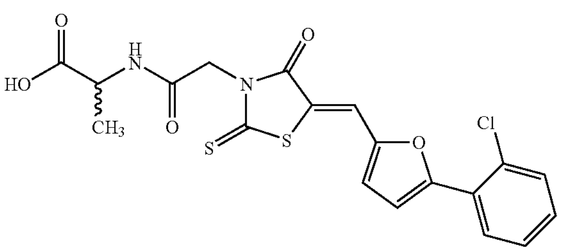 | N-[((5Z)-5-{[5-(2-chlorophenyl)-2-furyl]methylene}-4-oxo-2-thioxo-1,3-thiazolidin-3-yl)acetyl]alanine |
| 304 | 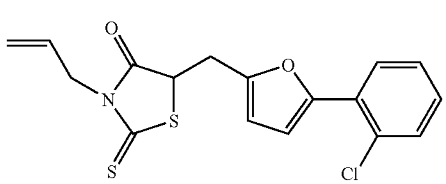 | 3-allyl-5-{[5-(2-ohlorophenyl)-2-furyl]methyl}-2-thioxo-1,3-thiazolidin-4-one |
| 305 | 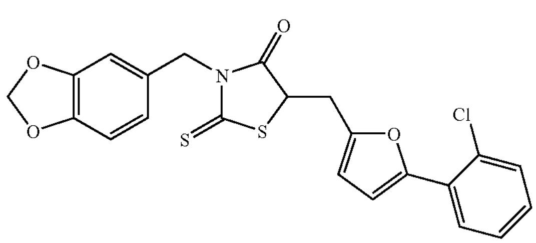 | 3-(1,3-benzodioxol-5-ylmethyl)-5-{[5-(2-chlorophenyl)-2-furyl]methyl}-2-thioxo-1,3-thiazolidin-4-one |

The compounds Table 1 can be prepared using art recognized methods. All of the compounds in this application were named using Chemdraw Ultra version 6.0.2, which is available through Cambridgesoft.com, 100 Cambridge Park Drive, Cambridge, Mass. 02140, Namepro version 5.09, which is available from ACD labs, 90 Adelaide Street West, Toronto, Ontario, M5H, 3V9, Canada, or were derived therefrom.

While particular geometric isomers (i.e., E or Z) are displayed throughout this specification, the invention also comprises the E or Z geometric isomers and mixtures thereof of all of the compounds of the invention, including compounds of formula I and compounds according to embodiments 1 to 9, as well as the compounds disclosed in the Table 1. The E and Z geometric isomers can be interconverted by photolysis, photo irradiation or exposure to free radicals. See, e.g., Ishida et al., *Tetrahedron Lett.* 30, 959 (1989). Exposure to certain solvents, e.g., DMSO, will facilitate conversion of an E isomer to the Z form.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3CH_2-$), in certain circumstances a bivalent linking moiety can be "alkyl," in which case those skilled in the art will understand the alkyl to be a divalent radical (e.g., $-CH_2CH_2-$), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_aB$, wherein a is 0 or 1. In such instances, when a is 0 the moiety is B and when a is 1 the moiety is AB. Also, a number of moieties disclosed herein exist in multiple tautomeric forms, all of which are intended to be encompassed by any given tautomeric structure. Other stereochemical forms of the compounds of the invention are also encompassed including but not limited to enantiomers, diastereomers, and other isomers such as rotamers.

For simplicity, when a substituent can be of a particular chemical class differing by the number of atoms or groups of the same kind in the moiety (e.g., alky, which can be $C_1$, $C_2$, $C_3$, etc.), the number of repeated atoms or groups is represented by a range (e.g., $C_1$-$C_6$ alkyl). In such instances each and every number in that range and all sub ranges are specifically contemplated. Thus, $C_1$-$C_3$ alkyl means $C_1$, $C_2$, $C_3$, $C_{1 2}$, $C_{1-3}$, and $C_{2-3}$ alkyl.

In addition to individual preferred embodiments of each substituent defined herein, the invention also comprises all combinations of preferred substituents.

The term "alkyl" as employed herein refers to straight and branched chain aliphatic groups having from 1 to 30 carbon atoms, preferably 1 to 15 carbon atoms, more preferably 1 to 6 carbon atoms, which is optionally substituted with one, two or three substituents. Unless otherwise specified, the alkyl group may be saturated, unsaturated, or partially unsaturated. As used herein, therefore, the term "alkyl" is specifically intended to include alkenyl and alkynyl groups, as well as saturated alkyl groups, unless expressly stated otherwise. Preferred alkyl groups include, without limitation, methyl, ethyl, propyl, isopropyl, butyl, tert butyl, isobutyl, pentyl, hexyl, vinyl, allyl, isobutenyl, ethynyl, and propynyl.

As employed herein, a "substituted" alkyl, cycloalkyl, aryl, or heterocyclic group is one having between one and about four, preferably between one and about three, more preferably one or two, non hydrogen substituents. Suitable substituents include, without limitation, halo, hydroxy, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

The term "cycloalkyl" as employed herein includes saturated and partially unsaturated cyclic hydrocarbon groups having 3 to 12, preferably 3 to 8 carbons, wherein the cycloalkyl group additionally is optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "hydrocarbyl" as employed herein includes all alkyl moieties and all cycloalkyl moieties (both as defined above), each alone or in combination. Thus, for example, hydrocarbyl includes methyl, ethyl, propyl, n-butyl, isobutyl, cyclopropyl, cyclohexyl, cyclopropyl-$CH_2$, cyclohexyl-$(CH_2)_3$, etc.

An "aryl" group is an optionally substituted $C_6$-$C_{14}$ aromatic moiety comprising one to three aromatic rings. Preferably, the aryl group is a $C_6$-$C_{10}$ aryl group. Preferred aryl groups include, without limitation, phenyl, naphthyl, anthracenyl, and fluorenyl. An "aralkyl" or "arylalkyl" group comprises an aryl group covalently linked to an alkyl group, either of which may independently be optionally substituted or unsubstituted. Preferably, the aralkyl group is $C_1$-$C_6$ alkyl ($C_6$-$C_{10}$)aryl, including, without limitation, benzyl, phenethyl, and naphthylmethyl. An "alkaryl" or "alkylaryl" group is an aryl group having one or more alkyl substituents. Examples of alkaryl groups include, without limitation, tolyl, xylyl, mesityl, ethylphenyl, tert butylphenyl, and methylnaphthyl.

A "heterocyclic" group (or "heterocyclyl") is an optionally substituted non-aromatic mono-, bi-, or tricyclic structure having from about 3 to about 14 atoms, wherein one or more atoms are selected from the group consisting of N, O, and S. One ring of a bicyclic heterocycle or two rings of a tricyclic heterocycle may be aromatic, as in indan and 9,10-dihydro anthracene. The heterocyclic group is optionally substituted on carbon with oxo or with one of the substituents listed above. The heterocyclic group may also independently be substituted on nitrogen with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino.

As used herein, the term "heteroaryl" refers to optionally substituted groups having 5 to 14 ring atoms, preferably 5, 6, 9, or 10 ring atoms; having 6, 10, or 14 pi electrons shared in a cyclic array; and having, in addition to carbon atoms, between one or more heteroatoms selected from the group consisting of N, O, and S. Preferred heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl.

In certain other preferred embodiments, the heterocyclic group is fused to an aryl or heteroaryl group. Examples of such fused heterocycles include, without limitation, tetrahydroquinolinyl and dihydrobenzofuranyl.

Additional preferred heterocyclyls and heteroaryls include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, 1H-indazolyl, indolenyl, indolinyl, indolizinyl, 3H-indolyl, isobenzofuranyl, isochromanyl, isoindazolyl, isoindolinyl, isoindolyl, isothiazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazolidinyl, pyrazolinyl, pyridazinyl, pyridooxazole, pyridoimidazole, pyridothiazole, pyridinyl, pyrrolidinyl, pyrrolinyl, 2H-pyrrolyl, quinazolinyl, 4H-quinolizinyl, quinuclidinyl, tetrahydroisoquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

A moiety that is substituted is one in which one or more hydrogens have been independently replaced with another chemical substituent. As a non limiting example, substituted phenyls include 2-fluorophenyl, 3,4-dichlorophenyl, 3-chloro-4-fluorophenyl, 2-fluoro-3-propylphenyl. As another non limiting example, substituted n octyls include 2,4-dimethyl-5-ethyloctyl and 3-cyclopentyloctyl. Included within this definition are methylenes ($-CH_2-$) substituted with oxygen to form carbonyl ($-CO$).

Unless otherwise stated, as employed herein, when a moiety (e.g., cycloalkyl, hydrocarbyl, aryl, heteroaryl, heterocyclic, urea, etc.) is described as "optionally substituted" it is meant that the group optionally has from one to four, preferably from one to three, more preferably one or two, non hydrogen substituents. Suitable substituents include, without limitation, halo, hydroxy, oxo (e.g., an annular $-CH-$ substituted with oxo is $-C(O)-$) nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, (b) $C_1$-$C_5$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$ alkylsulfinyl, arylalkylsulfinyl, arylsulfinyl, $C_1$-$C_8$ alkylsulfonyl, arylalkylsulfonyl, arylsulfonyl, $C_0$-$C_6$ N-alkyl carbamoyl, $C_2$-$C_{15}$ N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, or any of these rings fused or spiro fused to a cycloalkyl, heterocyclyl, or aryl, wherein each of the foregoing is further optionally substituted with one more moieties listed in (a), above; and (c) $-(CH_2)_s NR_{30}R_{31}$, wherein s is from 0 (in which case the nitrogen is directly bonded to the moiety that is substituted) to 6, and $R_{30}$ and $R_{31}$ are each independently hydrogen, cyano, oxo, carboxamido, amidino, $C_1$-$C_8$ hydroxyalkyl, $C_1$-$C_3$ alkylaryl, aryl $C_1$-$C_3$ alkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, aryl $C_1$-$C_3$ alkoxycarbonyl, $C_2$-$C_8$ acyl, $C_1$-$C_8$ alkylsulfonyl, arylalkylsulfonyl, arylsulfonyl, aroyl, aryl, cycloalkyl, heterocyclyl, or heteroaryl, wherein each of the foregoing is further optionally substituted with one more moieties listed in (a), above; or $R_{30}$ and $R_{31}$ taken together with the N to which they are attached form a heterocyclyl or heteroaryl, each of which is optionally substituted with from 1 to 3 substituents from (a), above.

The term "halogen" or "halo" as employed herein refers to chlorine, bromine, fluorine, or iodine.

As herein employed, the term "acyl" refers to an alkylcarbonyl or arylcarbonyl substituent.

The term "acylamino" refers to an amide group attached at the nitrogen atom. The term "carbamoyl" refers to an amide group attached at the carbonyl carbon atom. The nitrogen atom of an acylamino or carbamoyl substituent may be additionally substituted. The term "sulfonamido" refers to a sulfonamide substituent attached by either the sulfur or the nitrogen atom. The term "amino" is meant to include $NH_2$, alkylamino, arylamino, and cyclic amino groups.

General Synthetic Procedure

The compounds of the invention can be prepared using general synthetic procedures. The starting components are readily prepared from carboxylic acids, aldehydes, alkyls, benzene and phenol to a variety of substitutions can be made according to procedures well known to those skilled in the art and commercially available.

Scheme 1

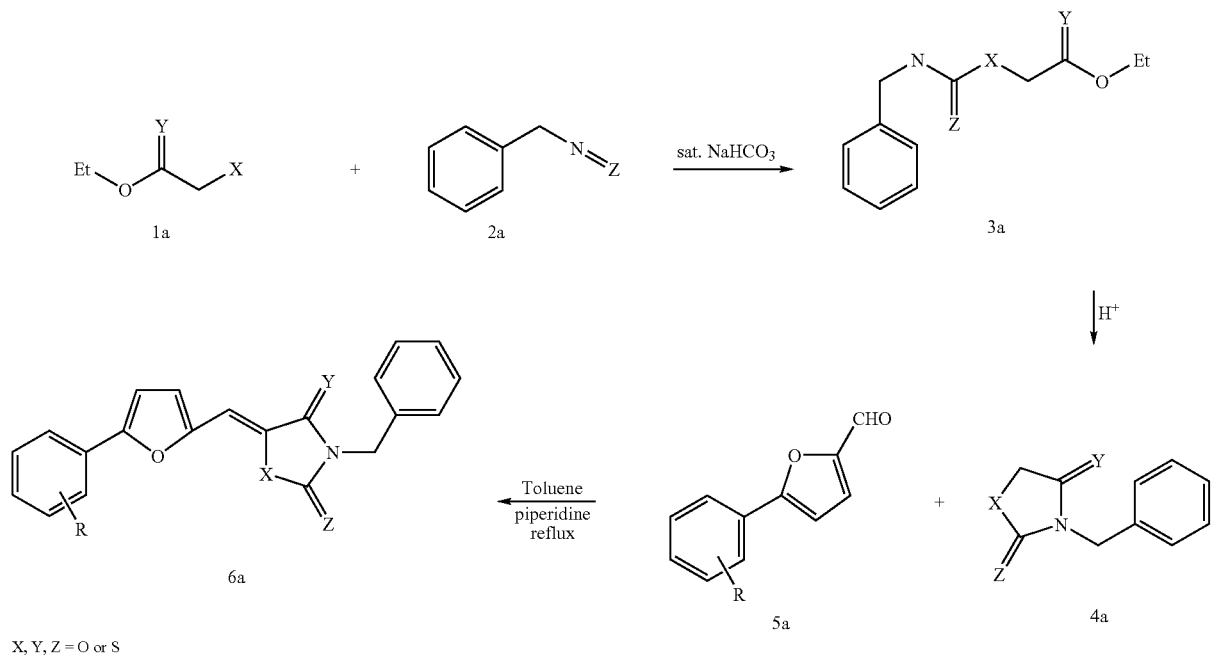

X, Y, Z = O or S

The compounds of the invention can be prepared according to Scheme 1. Scheme 1 illustrates only one way to prepare the compounds of the invention and is not meant to be limiting in any way. One skilled in the art would recognize that to obtain the compounds of the invention, reactant compounds 2a and 5a can be replaced with suitable compounds that have a variety of substituents in the phenyl and furanyl portions. The example below serves to illustrate this point.

EXAMPLE 1

Synthesis (5E)3-benzyl-2-thioxo-5-({5-[3-(trifluoromethyl)phenyl]-2-furyl}methylene)-1,3-thiazolidin-4-one Scheme II

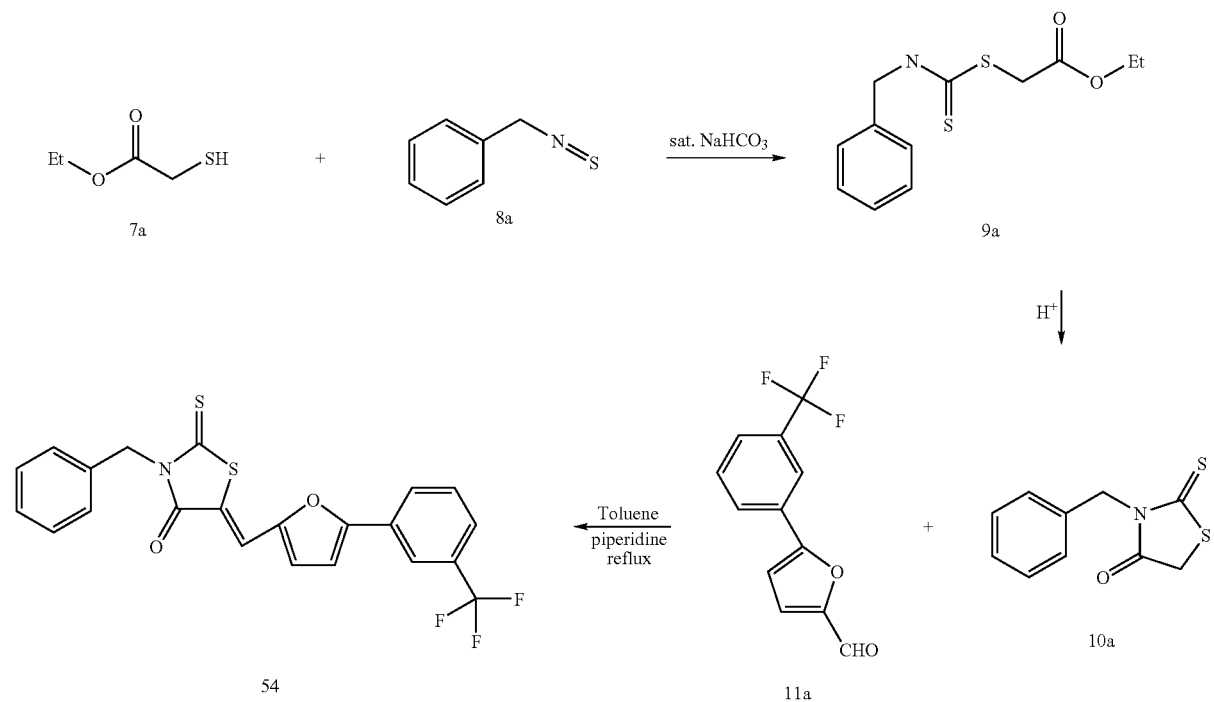

Step 1. Synthesis of Benzyl Rhodanine (10a)

To a mixture of 10 mmol (1.1 mL; 1.2 g) of thioglycolate (7a) and 11 mmole (1.64 g) of benzyl isothiocyanate (8a) was added 26 mL of saturated aqueous sodium bicarbonate. The reaction mixture was stirred at 40° C. for 3 hrs. About 5 mL of methanol was added to enhance solubility. The LC/MS analysis indicated two peaks: the major (85%) corresponded to the desired rhodanine (10a) and the minor peak was that of the uncyclized adduct (9a). The reaction mixture was treated with water and neutralized by addition of acetic acid. The aqueous mixture was extracted with ethyl acetate. The combined organic layers were concentrated to a volume of 10 mL, and 2 mL of acetic acid was added to this. The resulting mixture was heated at 50° C. overnight. Analysis by TLC showed one spot. The product was further purified by column chromatography using silica-gel and 35% ethyl acetate:hexane mixture as the mobile phase. The fractions corresponding to compound 10a were combined to give 2.18 g of pale reddish-yellow needles (yield=98%). $^1$H NMR (CDCl$_3$) δ 3.972 (s, 2H); 5.180 (s, 2H); 7.28 (m, 3H); 7.405 (m, 2H). MS (ES$^-$); 222.03 (M−1).

Step 2. Synthesis of Title Compound

To 1.52 g (0.65 mmole) of benzyl rhodanine (10a) was added 30 mL of toluene, 1.56 g (0.65 mmole) of 543-trifluoromethylphenyl)furan-2-carboxaldehyde (11a), and 0.8 mL of piperidine. The mixture was heated under reflux for 4 hours, and the reaction was monitored by TLC. At the end of the 4 hours, the TLC analysis showed no trace of the starting materials. The reaction mixture was allowed to cool and a bright yellow solid formed which was filtered and washed with hexane. The product was further purified by column chromatography using silica-gel and 40% ethyl acetate:hexane mixture as the mobile phase. Yield was 2.6 g (86%). $^1$H NMR: (CDCl$_3$) δ 5.335 (s, 2 H); 6.928-6.961 (dd, 2H, J=3.4 Hz); 7.265-7.35 (m, 3H); 7.449-7.488 (m, 3H); 7.613-7.633 (m, 2H); 7.934 (br.s, 1H); 9.945-8.15 (m, 1H). MS; ES+446.21 (M+1).

EXAMPLE 2

Synthesis (5E)-5-(1H-benzimidazol-2-ylmethylene)-3-(4-fluorophenyl)-2-thioxo-1,3-thiazolidin-4-one

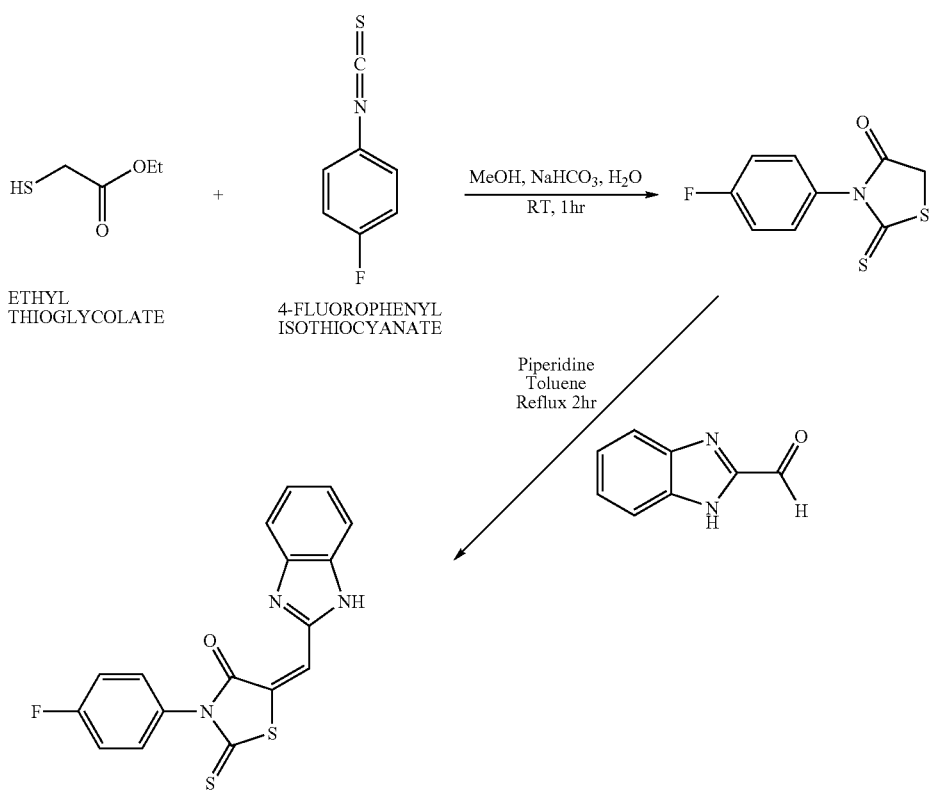

Scheme III

To 2.2 ml of ethyl thio glycolate was added 1.6 g of 4-fluoroisothiocyanate and 15 ml of saturated sodium bicarbonate. The reaction mixture was stirred at room temperature for 2 hrs. The reaction mixture was extracted with dichloromethane, solvent evaporated and the product purified by column chromatography on silica-gel using dichloromethane to elute the rhodanine. The off-white solid was pure by 1H NMR and LC. Yield was near quantitative. $^1$H NMR (CDCl$_3$): (δ) 4.190 (s, 2H); 7.181-7.216 (m, 4H).

To 450 mg of 344-fluorophenyl) rhodanine was added 350 mg of benzimidazole-2-carboxaldehyde and 20 ml of ethanol. The suspension was refluxed for 4 hours. The reaction mixture was cooled and the resulting solid purified by column chromatography on silica gel using 1:2 EtOAc hexane as eluant. The yellow solid obtained was pure by $^1$HNMR and LC. Yield 71%. $^1$HNMR (DMSO-d6) (δ) 7.25-7.317 (overlapping doublets 2H), 7.342-7.401 (overlapping d and dd, 2H); 7.458-7.5 (overlapping doublets, 2H); 7.599-7.621 (overlapping doublet and singlet, 2H); 7.774-7.798 (d, 1H, J=7.2 Hz).

EXAMPLE 3

Synthesis of (5E)-3-allyl-5-[(1-methyl-1H-benzimiazole-2-yl)methylene]-2-thioxo-1,3-thiazolidin-4-one A solution of 40 mg 231 μmol allyl rhodanine and 1 eq 37 mg of 1-methyl-2-formylbenzimidazole and 3.4 μL of piperidine in 1.5 mL toluene was heated in a capped vial at reflux temperature overnight. The reaction was cooled to RT and the product was collected by suction filtration, washed with a small amount of toluene and dried to yield the desired product. 1H CDCl$_3$ 7.82 ppm (m, 1H), 7.62 ppm (s, 1H), 7.37 ppm (m, 3H), 5.86 ppm (m, 1H), 5.36 ppm (m, 1H), 5.24 ppm (m, 1H), 4.78 ppm (d, 1H), purity 100%.

Pharmaceutical Compositions

In a second aspect, the invention provides pharmaceutical compositions comprising an inhibitor of ubiquitination according to the invention and a pharmaceutically acceptable carrier, excipient, or diluent. Suitable excipients are described in "Handbook of Pharmaceutical Excipients," 4$^{th}$ Edition, Rowe, R. C., Sheskey, P. J., and Weller, P. J., editors, American Pharmaceutical Association, Chicago, Ill. (2003), which is incorporated by reference in its entirety. Compounds of the invention may be formulated by any method well known in the art and may be prepared for administration to the patient by any route, including, without limitation, parenteral, oral, sublingual, subcutaneous, intravenous, intraperitoneal, intramuscular, intrapulmonary, vaginal, rectal, intraocular, transdermal, topical, intranasal, intratracheal, or intrarectal. In some instances, the compounds of the invention are administered directly as a solution or spray. In certain preferred embodiments, compounds of the invention are administered intravenously in a hospital setting. In certain other preferred embodiments, administration may preferably be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, pharmaceutical compositions according to the invention may contain, in addition to the inhibitor, carrier proteins (for example, such as serum albumin), diluents, fillers (for example microcrystalline cellulose, lactose, corn and other starches), binding agents, sweetners and flavoring agents, coloring agents, polyethylene glycol, salts, buffers, stabilizers, solubilizers, flavors, dyes and other materials well known in the art. The preparation of pharmaceutically acceptable formulations is described in many well known references to one skilled in the art, for example, Remington's Pharmaceutical Sciences, 18th Edition, ed. A. Gennaro, Mack Publishing Co., Easton, Pa., 1990.

As used herein, the term pharmaceutically acceptable salts refers to salts and complexes that retain the desired biological activity of the compounds of the invention and exhibit minimal or no undesired toxicological effects. Pharmaceutically acceptable salts include both the acid and base addition salts. Examples of acid salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, propionic acid, glycolic acid, pyruvic acid, oxalic acid, maleic acid, malonic acid, fumaric acid, tartaric acid, citric acid, cinnamic acid, mandelic acid, methanesulfonic acid, ethanesulfonic acid, p-toluenesulfonic acid, salicylic acid, succinic acid, malic acid, ascorbic acid, benzoic acid, tannic acid, pamoic acid, alginic acid, polyglutamic acid, naphthalenesulfonic acid, naphthalenedisulfonic acid, polygalacturonic acid and the like. Examples of base salts include those derived from inorganic bases such as potassium, sodium, lithium, ammonium, calcium, magnesium, iron, zinc, copper, manganese, aluminum and the like. Salts from derived from suitable organic non-toxic bases include salts of primary, secondary, and tertiary amines, substituted amines, cyclic amines, and basic ion exchange resins such as isopropylamine, trimethylamine, diethylamine, triethylamine, tripropylamine and ethanolamine.

The compounds can also be administered as pharmaceutically acceptable quaternary salts known by those skilled in the art, which specifically include the quaternary ammonium salt of the formula —NR$^+$ Z$^-$, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate). Moreover, the compounds of the invention can also be administered as prodrugs which can be converted to the active form in vivo.

The active compound is included in the pharmaceutically acceptable carrier or diluent in an amount sufficient to deliver to a patient a therapeutically effective amount without causing serious toxic effects in the patient treated. The compounds can be formulated in a variety of ways depending on the manner of administration. The concentration of the active compounds in these formulations can vary from 0.1 to 100% wt/wt. A preferred dose of the active compound for all of the above-mentioned conditions is in the range from about 0.01 to 550 mg/kg, preferably 300 to 550 mg/kg, more preferably 0.1 to 100 mg/kg per day, and more generally 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

When administered systemically, the ubiquitination inhibitor is preferably administered at a sufficient dosage to attain a blood level of the inhibitor from about 0.01 μM to about 100 μM, more preferably from about 0.05 μM to about 50 μM, still more preferably from about 0.1 μM to about 25 μM, and still yet more preferably from about 0.5 μM to about 20 μM. For localized administration, much lower concentrations than this may be effective, and much higher concentrations may be tolerated. One of skill in the art will appreciate that the dosage of ubiquitination inhibitor necessary to produce a therapeutic effect may vary considerably depending on the tissue, organ, or the particular animal or patient to be treated.

By "administration" is meant administering a therapeutically effective dose to a cell or patient. A therapeutically effective dose is a dose that produces the effects for which it is administered. The exact dose depends on the purpose of the treatment and can be ascertained by one skilled in the art using known techniques.

By "patient" is meant a human or other animal and organisms, for example, experimental animals. Thus, the compounds can be used for both human therapy and veterinary applications. In a preferred embodiment, the patient is human.

Treatment of Viral Disease

The third aspect of the invention provides for methods of treating diseases or conditions caused by viruses, comprising administering to a patient in need thereof a pharmaceutical composition comprising a therapeutically effective amount of a compound according to the invention. The compounds of the invention are inhibitors of ubiquitination and are effective as antiviral agents because they inhibit ubiquitination at critical steps in the life cycles of viruses. For example, the virulence of smallpox virus depends on the p28 polypeptide which has ubiquitin ligase activity. In other instances, viruses manipulate the host cell ubiquitination pathway in order to reproduce and avoid the host's attempts at disrupting the viral life cycle.

Banks et al., *Trends Cell Bio.* 13, 7 (2003), presents a review reporting on the important role that ubiquitin-protein ligases play in a variety processes involved in viral infection, including viruses such as human papillomavirus, HSV, adenovirus, Coxsackie, HCMV, KSHV, EBV, Paramyxovirus, Myxomavirus, Ebola, Retrovirus, and Rhabdovirus.

Coscoy et al., *Trends Cell Bio.* 13, 7 (2003), reports that the zinc-finger sub-family of viral proteins containing plant homeodomain (PHD) domains function as E3 ubiquitin ligases. Several PHD-containing viral proteins have been identified that promote immune evasion by down-regulating proteins involved in immune recognition.

Yasuda et al., *J. Virology* 77, 9987 (2003), reports that the cellular E3 ubiquitin ligase Nedd4 regulates budding mediated of Ebola virus VP40-induced virus-like particles (VLPs) through interaction with the PPxY motif. Yasuda et al. concludes that its findings suggest that viruses containing PPxY as an L-domain motif specifically use E3 in the process of virus budding.

Mansouri et al., *J. Virology* 77, 1427 (2003), shows that Myxomavirus protein M153R, which reduces cell surface expression of MHC-I, is a ubiquitin ligase that induces rapid internalization and lysosomal destruction of CD4, leading to a degradation of the anti-viral immune response.

Lorenzo et al., *J. Virology* 76, 5522 (2002) report that the Kaposi's Sarcoma-associated Herpesivirus $K_3$ (which contains a PHD) acts in a ubiquitin-proteasome-dependent manner in downregulating MHC-I complexes in cells expressing the $K_3$ protein.

Gu et al., *Proc. Nat'l Acad. Sci.* 100, 8963 (2003) report that degradation of promyelocytic leukemia protein and Sp100 (as well as the dispersal of ND10) by HSV-1 is mediated by the ubiquitin-conjugating enzyme $UbCH_5a$ E2 enzyme.

Boutell et al., *J. Biol. Chem.* 278, 36596 (2003), show that HSV-1 regulatory protein ICP0 is a genuine RING finger ubiquitin E3 ligase that can interact with and mediate the ubiquitination of the major oncoprotein p53 both in vitro and in vivo.

Goto et al., *J. Bio. Chem.* 278, 14657 (2003), reports on a novel human E3 ubiquitin ligase, c-MIR, having structural and functional similarity to Kaposi's sarcoma associated-herpes virus proteins, MIR (modulator of immune recognition) 1 and 2, which are involved in the evasion of host immunity and function as an E3 ubiquitin ligase for immune recognition-related molecules (e.g. major histocompatibility complex class I, B7-2, and ICAM-1).

Besnard-Guerin, *J. Bio. Chem.* (Oct. 14, 2003), report on HIV-1 Vpu protein, which acts as an adaptor for the proteasomal degradation of CD4 by recruiting CD4 and βTrCP, the receptor component of the multisubunit SCF-βTrCP E3 ubiquitin ligase complex.

Thus, in view of the foregoing references (each of which is incorporated herein by reference), the compounds of the invention can be used to treat patients suffering from diseases caused by a variety of viruses that use or depend on ubiquitination. Such viruses include, but are not limited to, enveloped and non-enveloped viruses such as retroviruses, poxviruses, influenza viruses, and the viruses referenced above, including those described in Banks et al., Coscoy et al., Yasuda et al., Mansouri et al., Lorenzo et al., Gu et al., Boutell et al., Goto et al., and Besnard-Guerin.

Treatment of HIV and Related Conditions

The fourth aspect of the invention provides a method for treating HIV infection as well as conditions related to HIV infection in a patient, comprising administering to a patient in need thereof a therapeutically effective amount of an inhibitor of ubiquitination of the invention. The preparation, dosage and administration of the inhibitors of ubiquitination of the invention for the treatment of HIV and related conditions can be carried out as described in the section "Pharmaceutical Compositions".

The inhibitors of ubiquitination of the invention are useful for the treatment of HIV infection and related conditions because they can inhibit the replication and spread of HIV. The replication and spread of HIV is decreased by the enzyme APOBEC3G which acts by causing extensive mutations in the cDNA reverse transcribed from the HIV genomic RNA. This has the effect of terminating the life cycle of HIV. To counteract this effect of APOBEC3G, HIV encodes the protein Vif that functions by decreasing the translation of APOBEC3G and increasing the degradation of APOBEC3G. The degradation of APOBEC3G is catalyzed by the 26S proteasome and depends on the polyubiquitination of APOBEC3G. Polyubiquitination serves as a signal for the 26S proteasome to degrade APOBEC3G. Thus, inhibitors of ubiquination of the invention can inhibit the function of the 26S proteasome by prevent the targeting of APOBEC3G to the 26S proteasome so that the intracellular concentration of APOBEC3G, as well as the concentration inside the HIV virions, is increased. This increased concentration of APOBEC3G in turn inhibits the replication and spread of HIV by diminishing the effect of Vif. The role of APOBEC3G in decreasing HIV replication and spread as well as methods for measuring the activity of the 26S proteasome, APOBEC3G and Vif are described in Stopak et al., "HIV-1 Vif Blocks the Antiviral Activity of APOBEC3G by Impairing Both Its Translation and Intracellular Stability," Mol. Cell. (2003), 12:pp 591-601, which is incorporated by reference in its entirety.

Treatment of Poxvirus

The compounds and compositions of the invention are also useful for the inhibition of poxvirus because they disrupt the function of poxvirus p28 polypeptide. The p28 polypeptide (28 kDa) is expressed by variola viruses, particularly smallpox virus, and plays important roles in virulence of poxviruses. The p28 polypeptide is an important determinant of poxvirus pathogenicity, and positively or negatively regulate expression of host or viral gene(s) involved in virus-host interaction. It also protects host cells from virus-induced apoptosis and UV light-induced apoptosis. It may achieve this function by acting upstream of caspase-3, blocking activation of the protease in response to UV irradiation. Its role in the life cycle of poxvirus may be to substitute for an unknown cellular factor(s) that may be required for the viral DNA replication or for a stage of virus reproduction between the expression of early genes and the onset of DNA synthesis. Disruption of p28 inhibits pathogenicity and the spread of virus from infected cells to uninfected cells.

The p28 polypeptide also exhibits ubiquitin ligase activity and this activity is critical for the replication and spread of poxvirus in target organs of infected animals and humans. The effects of p28 polypeptide also dependent on the ubiquitin ligase activity and may be the primary way by which p28 polypeptide exerts its biological functions. Through the action of the p28 polypeptide, poxviruses are able take advantage of the cellular biochemical machinery to replicate, spread, and cause lethal effects on the host. Inhibiting the p28 polypeptide ubiquitin ligase activity reduces the pathogenicity of poxvirus.

Other targets for inhibiting poxvirus as well as methods for identifying targets and inhibitors for inhibiting poxvirus are described in U.S. patent application 60/515,279 entitled "Methods and Compositions for the Identification of Anti-Poxvirus Agents," filed Oct. 28, 2003, which is incorporated by reference in its entirety.

Biological Assay

The following assay example illustrates the use of the compounds of the invention as inhibitors of ubiquitination. This assay example is intended to further illustrate certain preferred embodiments of the invention, and is not intended to limit the scope of the invention.

ASSAY EXAMPLE 1

Gst-Evp28 Ubiquitin Ligase Assay

The EVp28 was expressed from the cDNA that was cloned by ligation of several pieces of synthesised oligos according to the published sequence for EVp28. The cDNA was then subcloned into a baculovirus expression vector with either a GST or His tag at the N-terminus. The protein was expressed and purified from insect cells.

The wells of a Gst-plate were blocked with 100 ul of 1% casein in PBS for 1 hour at room temperature. The wells were then wash with 200 ul of 3×PBS, and 80 ul of reaction buffer containing Flag-ubiquitin was added to each well. The reaction buffer consisted of 62.5 mM Tris pH 7.6 (Trizma Base-Sigma T-8524), 3 mM $MgCl_2$ (Sigma M-2393), 1 mM DTT (Sigma D-9779), 2 uM ATP (Roche Boehringer Mann Corp.-635-316), and enough Flag-ubiquitin in order to get a final concentration of 100 ng/well of Flag-ubiquitin. After addition of the reaction buffer, to each well was added 10 ul of the compound in DMSO, 10 ul each of E1, E2, and Evp28 in protein buffer (20 mM Tris pH 7.6, 10% glycerol (Sigma G-5516), 1 mM DTT) so that the final concentration is 10 ng/well of E1, 10 ng/well of E2, and 25 ng/well of Evp28. The plate was shaken for 10 minutes and the reaction allowed to proceed for 1 hour at room temperature.

After 1 hour, the wells were wash with 200 ul 3×PBS, and 100 ul of anti-Flag (1:30,000 dilution) and anti-Mouse Ig-HRP (1:150,000 dilution) in PBS containing 0.25% BSA were added to each well. The plate was incubate at room temperature for 1 hour, and after the incubation, the wells were washed with 200 ul 3×PBS followed by the addition of 100 ul of Lumino substrate (1:5 dilution). The luminescence of each well was then measured using a fluorimeter to calculate the amount of the p28-ubiquitin complex.

The $IC_{50}$ value of Compound 54 determined by this assay was 0.016 μM. The $IC_{50}$ for Compound 307 determined by this assay was 0.092 μM.

What is claimed is:

1. A compound of the formula V:

V 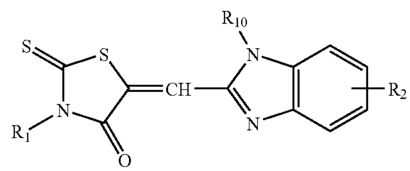 or a pharmaceutically acceptable salt thereof, wherein $R_1$ is —$NH_2$, $C_1$-$C_6$ alkyl, $C_1$-$C_2$ alkenyl, $C_1$-$C_6$ alkyl-S—$C_1$-$C_6$ alkyl, $C_0$-$C_6$ alky-aryl, $C_0$-$C_6$ alkyl-heteroaryl, $C_0$-$C_6$ alkyl-heterocyclyl, $C_0$-$C_6$ alkyl-carbocyclyl, —NH—$SO_2$-aryl, —$C_0$-$C_6$ alkyl-C(S)$NR_6R_7$, $C_0$-$C_6$ alky-heteroaryl-aryl, —NHC(O)-aryl, —$SO_2$—$R_6$, C(O)—$R_6$ or —C(O)—$OR_6$, wherein each one of the alkyl, aryl, heteroaryl, heterocyclic and carbocyclyl are optionally substituted with one or more $R_5$;

$R_2$ is independently —H, halogen, $C_1$-$C_6$ alkyl, $C_0$-$C_6$ alky-aryl, —$NO_2$, $C_0$-$C_6$ alkyl-C(O)—$OR_6$, $C_0$-$C_6$ alkyl-heteroaryl, $C_0$-$C_6$ alkyl-heterocyclyl, $C_0$-$C_6$ alkyl-carbocyclyl, —N($R_6$)—C(O)$NR_6R_7$, —$NHSO_2$-aryl, $C_0$-$C_6$ alky-heteroaryl-aryl or —C(O)—$R_6$, wherein each one of the aryl, heteroaryl, heterocyclic and carbocyclyl are optionally substituted with one or more $R_4$;

$R_4$ is halogen, oxo, —C(O)$OR_6$, —$NO_2$, $C_1$-$C_6$ alkyl optionally substituted with halo, —$C_1$-$C_6$ alkoxy optionally substituted with halo, —$CF_3$, —$SO_2NH_2$ or —C(O)—$OR_6$;

$R_5$ is halogen, oxo, $C_1$-$C_6$ alkoxy, $C_1$-$C_6$ alkyl, $C_0$-$C_6$ alkyl-aryl, —$NO_2$, di($C_1$-$C_6$ alkyl)amino, —$CF_3$, —OH, —$SO_2NH_2$ or —C(O)—$OR_6$;

$R_6$ and $R_7$ are independently —H, halogen, $C_1$-$C_6$ alkoxy, $C_1$-$C_6$ alkyl, $C_2$-$C_6$ alkenyl, aryl, di($C_1$-$C_6$ alkyl)amino, —$CF_3$, —OH or —C(O)—$OR_6$;

$R_{10}$ is —H, halogen, $C_1$-$C_6$ alkyl, $C_0$-$C_6$ alky-aryl, —$NO_2$, $C_0$-$C_6$ alkyl-C(O)—$OR_6$, $C_0$-$C_6$ alkyl-heteroaryl, $C_0$-$C_6$ alkyl-heterocyclyl, $C_0$-$C_6$ alkyl-carbocyclyl, —N($R_6$)—C(O)$NR_6R_7$, —$NHSO_2$-aryl, $C_0$-$C_6$ alky-heteroaryl-aryl, or —C(O)—$R_6$, wherein each one of the aryl, heteroaryl, heterocyclic and carbocyclyl are optionally substituted with one or more $R_4$.

2. The compound according to claim 1 wherein a) $R_{10}$ is selected from —H and $C_1$-$C_6$-alkyl;

b) $R_1$ is (i) aryl optionally substituted with one or more $R_4$ wherein in preferred embodiments $R_1$ is substituted with a single $R_4$ selected from halo and ($C_0$-$C_6$-alkyl)($C_0$-$C_6$-alkyl)N—, more preferably fluoro, chloro, bromo, or di-ethylamino; or (ii) $C_2$-$C_6$ alkenyl, preferably $CH_2$=CH—; and/or c) $R_2$ is —H or $C_1$-$C_6$ alkyl.

3. A composition comprising a compound according to claim 1 together with a pharmaceutically acceptable carrier, excipient, or diluent.

* * * * *